(12) United States Patent
Dudding et al.

(10) Patent No.: US 12,201,115 B2
(45) Date of Patent: Jan. 21, 2025

(54) ANTI-PATHOGEN COMPOSITIONS

(71) Applicant: CLAW Biotech Holdings, LLC, St. Louis, MO (US)

(72) Inventors: Jeffery L. Dudding, Center, MO (US); Amod P. Paranjpe, Augusta, MO (US)

(73) Assignee: CLAW Biotech Holdings, LLC, St. Louis, MO (US)

( * ) Notice: Subject to any disclaimer, the term of this patent is extended or adjusted under 35 U.S.C. 154(b) by 57 days.

(21) Appl. No.: 17/638,368

(22) PCT Filed: Aug. 25, 2020

(86) PCT No.: PCT/US2020/047841
§ 371 (c)(1),
(2) Date: Feb. 25, 2022

(87) PCT Pub. No.: WO2021/041439
PCT Pub. Date: Mar. 4, 2021

(65) Prior Publication Data
US 2022/0322677 A1    Oct. 13, 2022

Related U.S. Application Data

(60) Provisional application No. 63/007,743, filed on Apr. 9, 2020, provisional application No. 62/893,513, filed on Aug. 29, 2019.

(51) Int. Cl.
| | |
|---|---|
| *A61K 9/14* | (2006.01) |
| *A01N 25/10* | (2006.01) |
| *A01N 25/12* | (2006.01) |
| *A01N 25/34* | (2006.01) |
| *A01N 59/16* | (2006.01) |
| *A01N 59/20* | (2006.01) |
| *A01P 1/00* | (2006.01) |
| *A61K 8/19* | (2006.01) |
| *A61K 8/27* | (2006.01) |
| *A61Q 17/00* | (2006.01) |

(52) U.S. Cl.
CPC ............ *A01N 59/20* (2013.01); *A01N 25/10* (2013.01); *A01N 25/12* (2013.01); *A01N 25/34* (2013.01); *A01N 59/16* (2013.01); *A01P 1/00* (2021.08); *A61K 8/19* (2013.01); *A61K 8/27* (2013.01); *A61Q 17/005* (2013.01)

(58) Field of Classification Search
None
See application file for complete search history.

(56) References Cited

U.S. PATENT DOCUMENTS

| | | |
|---|---|---|
| 6,391,253 B1 | 5/2002 | Tochihara et al. |
| 9,162,013 B2 | 10/2015 | Guggenbichler et al. |
| 9,675,079 B1 | 6/2017 | Dudding et al. |
| 10,472,157 B1 | 11/2019 | Dudding et al. |
| 10,959,426 B1 | 3/2021 | Dudding et al. |
| 2005/0182152 A1* | 8/2005 | Nonninger ............ A01N 25/26 523/122 |
| 2010/0057199 A1 | 3/2010 | Guggenbichler et al. |
| 2010/0136073 A1 | 6/2010 | Preuss et al. |
| 2012/0171271 A1 | 7/2012 | Loontjens et al. |
| 2013/0168279 A1 | 7/2013 | Sandford |
| 2014/0158625 A1 | 6/2014 | Pradhan et al. |
| 2016/0106108 A1 | 4/2016 | Lunk et al. |
| 2019/0029259 A1 | 1/2019 | Guggenbichler |
| 2019/0099719 A1 | 4/2019 | Al-Ahmed et al. |
| 2019/0246635 A1 | 8/2019 | Zhang et al. |

FOREIGN PATENT DOCUMENTS

| | | |
|---|---|---|
| CA | 3075783 A1 | 3/2019 |
| CN | 112209445 A | 1/2021 |
| CN | 113896242 A | 1/2022 |
| EA | 029830 B1 | 5/2018 |
| JP | H9-256116 A | 9/1997 |
| JP | H11-35412 A | 2/1999 |
| JP | H11-256279 A | 9/1999 |
| JP | H11-264057 A | 9/1999 |
| JP | 2000-154320 A | 6/2000 |
| JP | 2001-040489 A | 2/2001 |
| JP | 2007-51158 A | 3/2007 |
| JP | 2010-509385 A | 3/2010 |

(Continued)

OTHER PUBLICATIONS

Shafaei et al. "Cellulose acetate-based composites with antimicrobial properties from embedded molybdenum trioxide particles". Letter in Applied Microbiology ISSN 0266-8254 (Year: 2016).*
Bajpai, S.K. et al., Novel Strategy for Synthesis of ZnO Microparticles Loaded Cotton Fabrics and Investigation of their Antibacterial Properties, Journal of Engineered Fibers and Fabrics, 9 pages, (2011).
Shafaei, S. et al., Polymorphs of molybdenum trioxide as innovative antimicrobial materials, Surface Innovations, 1(4):202-208 (2016).
U.S. Appl. No. 17/175,893, filed Jun. 3, 2021, Claw Biotech Holdings, LLC.
Center for Disease Control, Antibiotic Resistance Threats in the United States, 114 pages, (2013).
Chen, F. et al., Two-Dimensional Molybdenum Sulfide-Based Materials for Photo-Excited Antibacterial Application, Adv. Healthc. Mater., e2200360, (2022).

(Continued)

*Primary Examiner* — Susan T Tran
(74) *Attorney, Agent, or Firm* — Choate, Hall & Stewart LLP; Michael A. Shinall

(57) ABSTRACT

Compositions comprising an activated metal or metal oxide useful for neutralizing pathogens. In some embodiments, the present disclosure provides a solid anti-pathogen composition comprising an active component, wherein the active component comprises particles of at least one activated metal. In some embodiments, the present disclosure provides an anti-pathogen liquid composition comprising particles of an active component and in a water or saline solution, wherein the active component comprises particles of at least one activated metal. Also described herein are methods for neutralizing microbes and pathogens on surfaces and in water.

8 Claims, 11 Drawing Sheets

(56) References Cited

FOREIGN PATENT DOCUMENTS

| JP | 2010-525091 A | 7/2010 |
|---|---|---|
| JP | 2013-501018 A | 1/2013 |
| JP | 2014-1190 A | 1/2014 |
| JP | 2015-218159 A | 12/2015 |
| WO | WO-2014/141812 A1 | 9/2014 |
| WO | WO-2017/218238 A1 | 12/2017 |
| WO | WO-2021/041439 A1 | 3/2021 |

OTHER PUBLICATIONS

Fasim, F., et. al., Solubilization of zinc salts by a bacterium isolated from the air environment of a tannery, FEMS Microbiology Letters, 213:1-6 (2002). <https://academic.oup.com/femsle/article/213/1/1/516142>. Retrieved Nov. 1, 2020.

Gautam, H., Researchers from IIT Mandi develop reusable virus killing masks from discarded ones, (2021), <https://www.theoptimistcitizen.com/iit-mandi/>. Retrieved on May 14, 2021.

Guo, J. et al., Coating CoCrMo Alloy with Graphene Oxide and ε-Poly-L-Lysine Enhances Its Antibacterial and Antibiofilm Properties, International Journal of Nanomedicine, 2021(16):7249-7268, (2021).

International Preliminary Report on Patentability with accompanying Annexes, PCT/US2020/047841, 9 pages, Dec. 14, 2021.

International Preliminary Report on Patentability, PCT/US2020/047841, 3 pages, Sep. 15, 2021.

International Search Report for PCT/2020/047841, filed Aug. 25, 2020, 4 pages, (Nov. 13, 2020).

Kampf, G. et al., Persistence of coronaviruses on inanimate surfaces and their inactivation with biocidal agents, J. Hosp. Infect., 104(3):246-251, (2020).

Kramer, A. et al., How long do nosocomial pathogens persist on inanimate surfaces? A systematic review, BMC Infect. Dis., 6:130, (2006).

Kumar, P., et. al., Reusable $MoS_2$-Modified Antibacterial fabrics with photothermal disinfection properties for repurposing of personal protective masks, (2021).

Lam, Nadia, New anti-Covid steel developed in Hong Kong expected to hit market in 6 months, The Star, Aseanplus News, 4 pages, (Dec. 10, 2021).

Liberatore, S., New Covid-killing steel reduces presence of the virus by 99.75% within three hours, dailymail.com, 11 pages, (Dec. 7, 2021).

Lopes, E. et al., Bactericidal efficacy of molybdenum oxide nanoparticles against antimicrobial-resistant pathogens, J. Med. Microbiol., 67(8):1042-1046, (2018).

marketwatch.com, Global Molybdenum Oxide Market Competitive Landscape and Analysis by Recent Trends 2022 to 2028, 5 pages, (2022).

Molybdenum Blue, PubChem CID 1700447, created Aug. 8, 2022, modified May 28, 2022, 14 pages, (2022).

Pinon, A. and Vialette, M., Survival of Viruses in Water, Intervirology, 61(5):214-222, (2018).

Shafaei, S. et. al., Cellulose acetate-based composites with antimicrobial properties from embedded molybdenum trioxide particles, Letters in Applied Microbiology, 64: 43-50, (2016). <https://sfamjournals.onlinelibrary.wiley.com/doi/epdf/10.1111/lam.12670>. Retrieved Oct. 27, 2020.

Sun, D. et. al., An Investigation of the antibacterial ability and cytotoxicity of a novel Cu-bearing 317L stainless steel, 6, (2016). <https://ww.ncbo.nlm.nih.gov/pmc/articles/PMC4935851/pdf/srep29244.pdf>. Retrieved on Oct. 27, 2020.

Tokyo Institute of Technology, A materials science approach to combating coronavirus, <https://phys.org/news/2021-03-materials-science-approach-combating-coronavirus.html> retrieved Mar. 16, 2021.

Turner, R. J., Metal-based antimicrobial strategies, Microb. Biotechnol., 10(5):1062-1065, (2017).

Van Doremalen, N. et al., Aerosol and Surface Stability of SARS-CoV-2 as Compared with SARS-CoV-1, N. Engl. J. Med., 382(16):1564-1567, (2020).

Written Opinion for PCT/2020/047841, filed Aug. 25, 2020, 7 pages, (Nov. 13, 2020).

Written Opinion of the International Preliminary Examining Authority, PCT/US2020/047841, 3 pages, Sep. 15, 2021.

Sunada, K. et al., Examination for antivirus activity of metal oxide under visible light, Kanagawa Institute of Industrial Science and Technology Annual Research Report (Web) (KISTEC Annual Research Report), 2019:153-155 (2019).

* cited by examiner

ANTI-PATHOGEN COMPOSITIONS

CROSS-REFERENCE TO RELATED APPLICATIONS

The present application is a 371 national phase entry of PCT/US2020/047841, filed Aug. 25, 2020, which claims priority to U.S. Provisional Application Nos. 62/893,513, filed Aug. 29, 2019, and 63/007,743, filed Apr. 9, 2020, the entirety of each of which is incorporated by reference herein in its entirety.

BACKGROUND

Pathogens, such as bacteria, fungi, viruses, and algae can stably exist on a dry surface or in water for hours, days, or even months. See Kramer, et al., *BMC Infect. Dis.*, 6:130 (2016) (reviewing varying survival rates of bacteria on dry surfaces); Pinon, et al., *Intervirology*, 61:214-222 (2018) (reviewing survival rates for viruses in water). SARS-CoV-2, the virus that causes coronavirus disease 2019 (COVID-19), which to date has infected close to a million people worldwide and has already killed thousands, is currently understood to exist for hours or even days in aerosols and on various surfaces. See van Doremalen, et al., *New England J. of Med.*, DOI: 10.1056/NEJMc2004973 (Mar. 17, 2020), and G. Kampf, et al., *J. of Hospital Infection*, 104:246e251 (2020). Moreover, some pathogens can live for more than a month in water. These pathogens can cause serious infection or death.

SUMMARY

There is a need for anti-pathogen compositions capable of neutralizing pathogens on contact, allowing for control of harmful pathogens. The present disclosure encompasses the recognition that certain metals (e.g., in particular certain transition metals) are useful for neutralizing pathogens. Moreover, the present disclosure encompasses the insight that the ability of certain metals to neutralize pathogens can be increased when subjected to certain conditions. Certain metals, as described herein, after being subjected to certain conditions (i.e., to thereby become "activated"), can further be incorporated into compositions comprising, for example, a polymer, a biopolymer/biocomposite, or a saline solution, and retain the metal's ability to neutralize pathogens on contact. Such compositions are safe for use on every day surfaces in the home, as well as in medical facilities, manufacturing/industrial sites, commercial sites, and even directly on human skin.

In some embodiments, the present disclosure provides a composition comprising an anti-pathogen solid composition comprising an active component, wherein the active component comprises particles (e.g., ionic particles, microparticles or nanoparticles) of at least one activated metal. The present disclosure encompasses the insight that activated metal is particularly useful for neutralizing (i.e., inhibiting growth, replication, or otherwise killing) pathogens (e.g., bacteria, fungi, viruses, algae (e.g., cyanobacteria, dinoflagellates and diatoms), or microorganisms causing disease), in particular those that are capable of harming plants or animals (including humans or other mammals). For example, the present disclosure encompasses the insight that the compositions and suspensions provided herein are capable of neutralizing many common pathogens, including methicillin resistant staphylococcus aureus (MRSA), legionella, *E. coli*, and coronaviruses (e.g., SARS-CoV-2) upon contact. The activation of the metal by the methods described herein provides for an unexpected increase in percentage of pathogens that are neutralized upon contact, at a shorter period of time.

Moreover, anti-pathogen solid compositions described herein can be flexibly formed into a variety of shapes, or alternatively, flexibly cover a surface. Such a surface would have anti-pathogen properties that are critical both in the healthcare industry, as well as in the home, in agriculture, in food (e.g., for safety and storage), in transportation, and the like. For example, in some embodiments, a solid composition comprises about 0.01% to about 5% by weight of an active component, wherein the active component comprises particles (e.g., ionic particles, microparticles or nanoparticles) of an activated transition metal or transition metal oxide; and about 1% to about 99.99% by weight of a polymer.

The present disclosure further encompasses the insight that the active component can also be suspended into a solution, and be used to sterilize water, e.g., drinking water, or further incorporated into an ointment, cream, lotion, or the like, for use in neutralizing pathogens on human skin (i.e., a hand sanitizer).

DETAILED DESCRIPTION

Figure 1A:
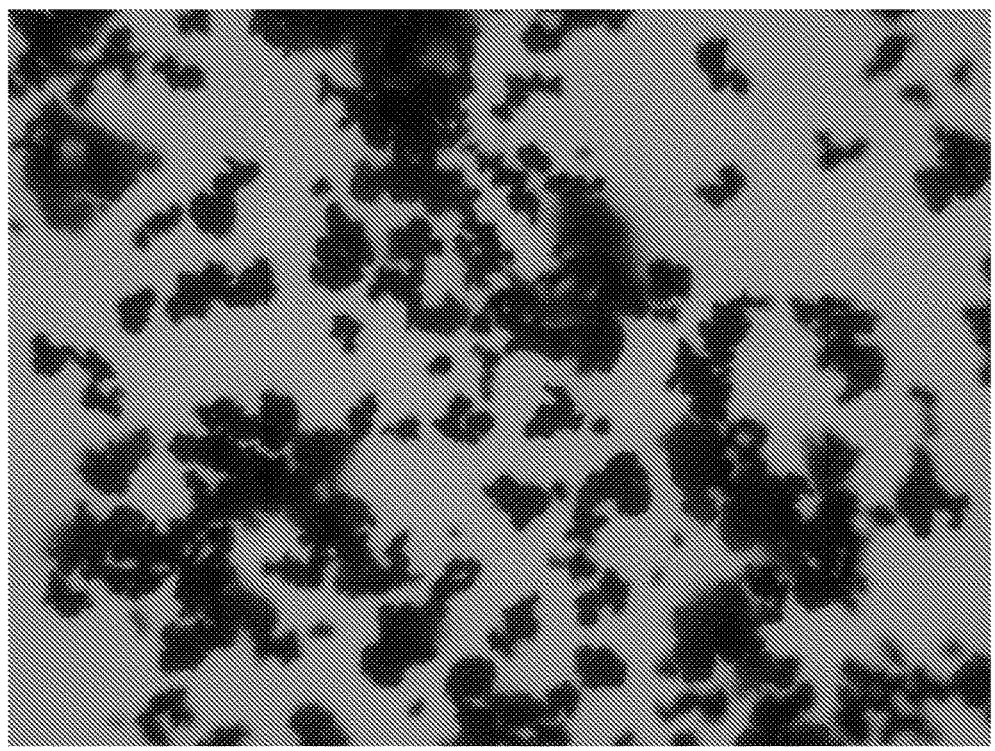
FIG. 1A is an image of unactivated molybdenum particles in saline, taken by an OMAX 40X-2500X LED Digital Trinocular Microscope.

There is a need for anti-pathogen compositions capable of neutralizing pathogens on contact, both on dry surfaces (including human skin), and in water, allowing for control of harmful pathogens. Metal-based materials, e.g., stainless steel, are particularly useful in the medical and food storage industry, as they are, among other things, rust proof, non-magnetic, have high heat resistance, and maintain their shape after formation. The present disclosure encompasses the recognition that solid compositions, e.g., metal compositions (including, for example, stainless steel compositions) comprising metals in an "activated" state (as described in more detail herein), are useful for neutralizing pathogens, making them invaluable for use in the medical and food manufacturing industry.

Moreover, the present disclosure encompasses the insight that the ability of certain metals to neutralize pathogens can be increased when subjected to certain conditions, i.e., are "activated." The present disclosure further encompasses the insight and development of incorporating these activated metals into solid forms (e.g., in plastics, ceramics, polymers, biopolymers/biocomposites, rubbers, fabric, paper, glass, metals, and combinations thereof) and the like such that they can be formed into a number of products for use both in the medical field and in the household, as well as the insight that these metals can be used to purify water. Such compositions are safe for use on every day surfaces in the home, in agriculture, the food industry, and in medical facilities, as well as for use directly on human skin.

As described herein, in some embodiments, the present disclosure provides a solid composition comprising an active component, wherein the active component comprises particles of at least one activated metal. In some embodiments, at least one activated metal is or comprises molybdenum (Mo). In some embodiments, the solid composition is a metal further comprising an active component. In some embodiments, an active component is useful as an anti-pathogenic agent, e.g., has anti-pathogenic properties. For example, the present disclosure encompasses the use of molybdenum (Mo) as an anti-pathogen agent in solid compositions, capable of neutralizing (i.e., de-activating or killing or substantially eliminating) pathogens. In some embodiments, the present disclosure encompasses the insight that certain forms of molybdenum are unexpectedly more efficient at neutralizing pathogens than other forms of molybdenum, such as neutral molybdenum or certain forms of molybdenum (V) or (VI), such as molybdenum trioxide ($MoO_3$).

The need for anti-pathogen products for both in the home and in the medical field is at a critical level. In light of the COVID-19 pandemic, many stores cannot keep anti-pathogen cleaners and sanitizers in stock, and many hospitals and medical offices are struggling to obtain masks and other protective or sterile equipment. Notwithstanding the issues related to COVID-19, many bacteria and other pathogens continue to evolve resistance to typical antibiotics. For example, as noted by the Center for Disease Control and Prevention (CDC) in 2013, "[a]ntimicrobial resistance is one of our most serious health threats, and some pathogens have even become resistant to multiple types or classes of antibiotics. The loss of effective antibiotics will undermine our ability to fight infectious diseases . . . " CDC, *Antimibiotic Resistant Threats*, available at https://www.cdc.gov/drugresistance/pdf/ar-threats-2013-508.pdf. As noted by Lopes, et al., "[a]mong Gram-positive pathogens, methicillin-resistant *S. aureus* (MRSA) and vancomycin-resistant *enterococci* (VRE) pose the biggest threats" as "MRSA is widespread in hospitals worldwide . . . " Medical facilities also suffer from infections caused by *Enterobacteriaceae* (mostly *Klebsiella pneumoniae*), *Pseudomonas aeruginosa*, and *Acinetobacter baumannii*, multidrug-resistant (MR), with "[g]ram-negative pathogens are also becoming increasingly prevalent in the community (mostly *Escherichia coil*)." Lopes, et al., *J. of Medical Microbiology,* 67(8):1042-1046 (2018).

Metal-based anti-pathogen compositions have been used for many years with varying success, but are seeing more use as researchers look for alternatives to traditional anti-pathogens. See R. J. Turner, *Microb. Biotechnol.,* 10(5): 1062-1065 (2017). Generally, the anti-pathogen metals have been those selected from the d-block transition metals (V, Ti, Cr, Co, Ni, Cu, Zn, Tb, W, Ag, Cd, Au, Hg) and other metals and metalloids from groups 13-16 of the periodic table (Al, Ga, Ge, As, Se, Sn, Sb, Te, Pb and Bi). Id. Historically, the most prevalent metals in anti-pathogen compositions have been Zn, Cu, and Ag. Silver, with its high cost and potential for toxicity, has limited applicability.

Others have also examined the viability of molybdenum through transition metal acid molybdenum trioxide ($MoO_3$). For example, Lopes et al. reported the use of $MoO_3$ nanoparticles against a variety of microbes, including "(i) eight *Staphylococcus aureus*, including representatives of methicillin-resistant *S. aureus* epidemic clones; (ii) six *enterococci*, including vancomycin-resistant isolates; and (iii) 25 Gram-negative isolates (*Escherichia coli, Klebsiella pneumoniae, Pseudomonas aeruginosa, Acinetobacter baumannii, Enterobacter cloacae*), including extended spectrum beta-lactamases and carbapenemases producers." Lopes, et al., *J. of Medical Microbiology,* 67(8):1042-1046 (2018).

The present disclosure further encompasses an improvement over previous anti-pathogen preparations using molybdenum and molybdenum trioxide, such as the ones described by Lopes or U.S. Pat. No. 9,162,013. For example, neither of Lopes or U.S. Pat. No. 9,162,013 describe or suggest the activation of the molybdenum trioxide, let alone the unexpected benefit of improved anti-pathogen activity associated with the activation of molybdenum trioxide (or indeed molybdenum itself). The present disclosure further encompasses the recognition that such activated forms, as not taught or suggested by Lopes or U.S. Pat. No. 9,162,013 are stable at ambient conditions for at least 6 months, making them ideal for use in commercial products, which require substantially long periods of storage while maintaining meaningful anti-pathogen activity.

Moreover, the present disclosure encompasses the insight that molybdenum can be used in other forms than its transition metal acid form, and moreover, can be incorporated into solid compositions (e.g., plastics, polymers, rubbers, ceramics, fabrics, biopolymers/biocomposites, paper, glass, metals, etc.) for use in forming a variety of products (e.g., or flexible covers); or into liquid compositions, e.g., for use in sanitizers, including ointments, lotions, creams, aerosols, sprays, and the like. Such products and compositions have a wide variety of uses in both the household and the medical field.

The present disclosure encompasses the insight that molybdenum (and other metals such as zinc, copper, silver, and gold), including in its transition metal acid form(s), can be further manipulated to increase the ability of the metal atom to neutralize pathogens. That is, as described by methods herein, metals can be activated upon subjecting them to certain conditions that increase the anti-pathogen properties, and such activated form(s) (and/or properties thereof) are suitably stable such that they can be meaningfully stored for long periods of time.

Activated Metals

As described above, the present disclosure provides, among other things, an anti-pathogen solid composition comprising an active component, wherein the active component comprises particles (e.g., microparticles or nanoparticles) of at least one activated metal. In some embodiments, an activated metal is any transition metal or oxide thereof. As used herein, an "oxide" of a transition metal refers to a transition metal that has been oxidized, i.e., the metal is in a cationic form and, in some embodiments, has bound to one or more counterions (e.g., chalcogens, such as oxygen or sulfur) to stabilize the cationic form of the metal. Exemplary transition metals that are useful in embodiments described herein include Mo, Zn, Cu, Au, and Ag, as well as their known oxidized forms (e.g., Mo(IV), Mo(V), Mo(VI), Zn(II), Cu(I), Cu(II), Au(I), Au(III), Ag(I), $MoO_2$, $MoO_3$, $Mo_2O_6$, $H_2MoO_5$, ZnO, $Cu_2O$, CuO, $Au_2O$, $Au_2O_3$, and $Ag_2O$).

Figure 1B:
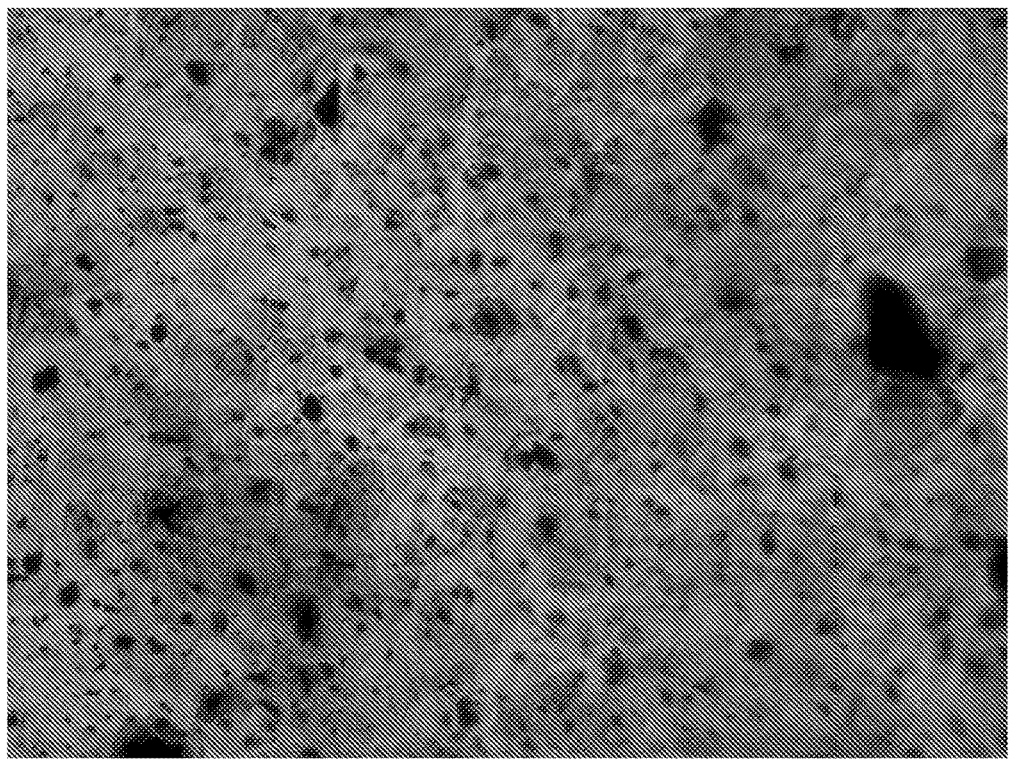
FIG. 1B is an image of unactivated molybdenum particles in polypropylene, taken by an OMAX 40X-2500X LED Digital Trinocular Microscope.
Figure 2A:
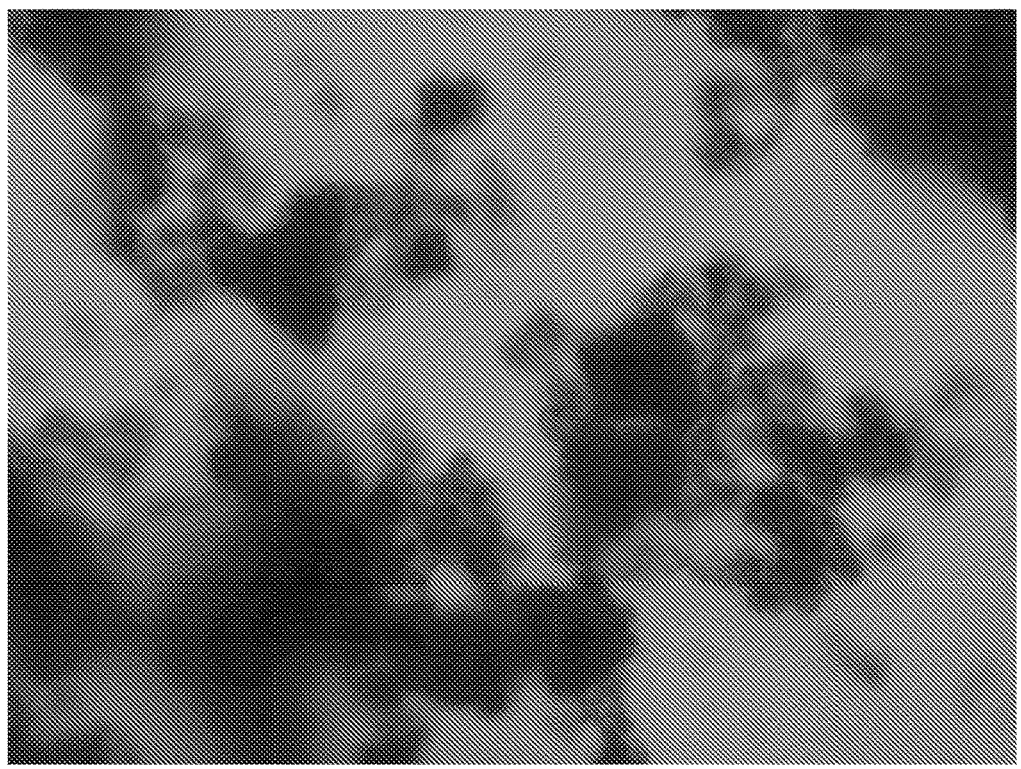
FIG. 2A is an image of activated molybdenum particles in saline, taken by an OMAX 40X-2500X LED Digital Trinocular Microscope.
Figure 2B:
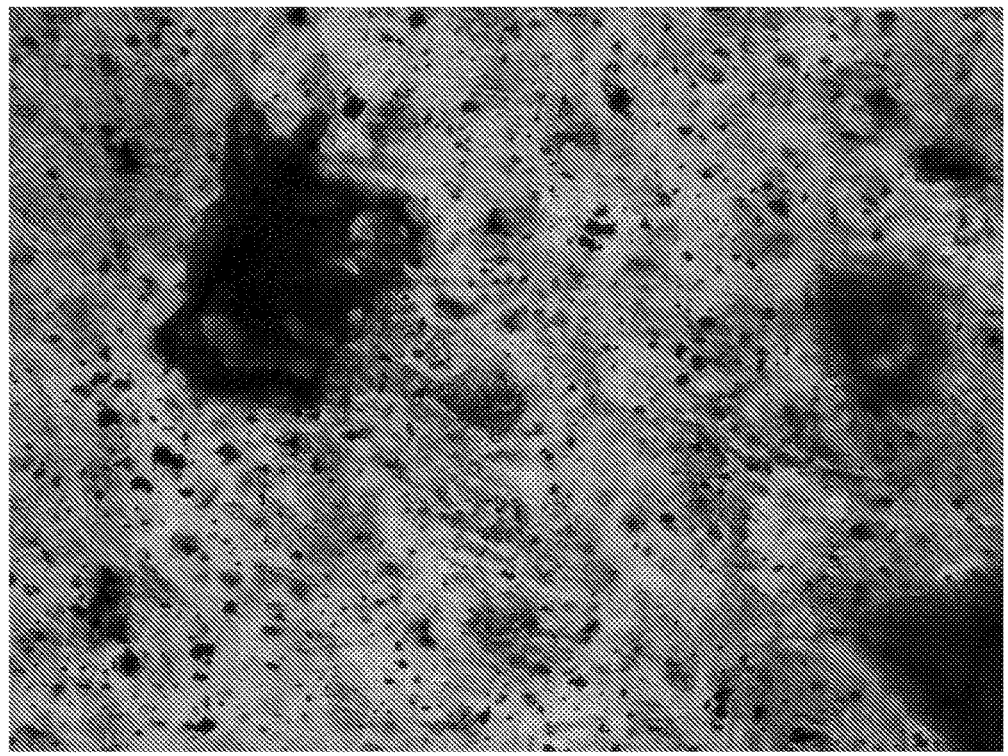
FIG. 2B is an image of activated molybdenum particles in polypropylene, taken by an OMAX 40X-2500X LED Digital Trinocular Microscope.
Figure 2C:
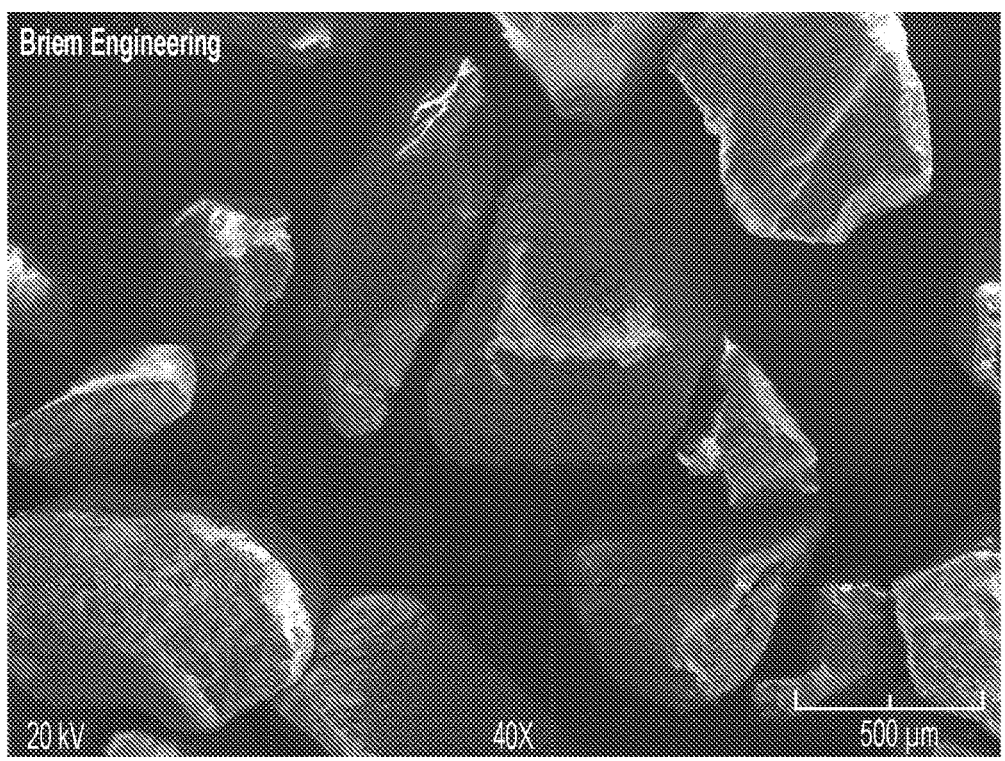
FIG. 2C is an image of activated molybdenum powders, taken by an OMAX 40X-2500X LED Digital Trinocular Microscope.
Figure 2D:
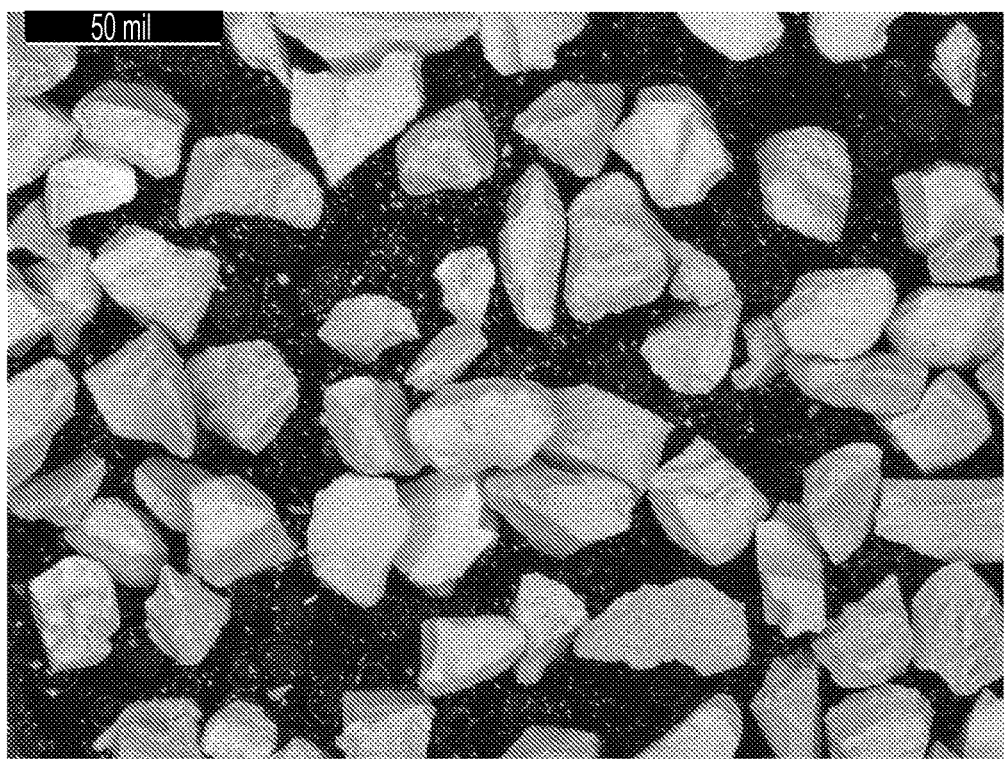
FIG. 2D is an image of activated molybdenum powders, taken by an OMAX 40X-2500X LED Digital Trinocular Microscope.
Figure 2E:
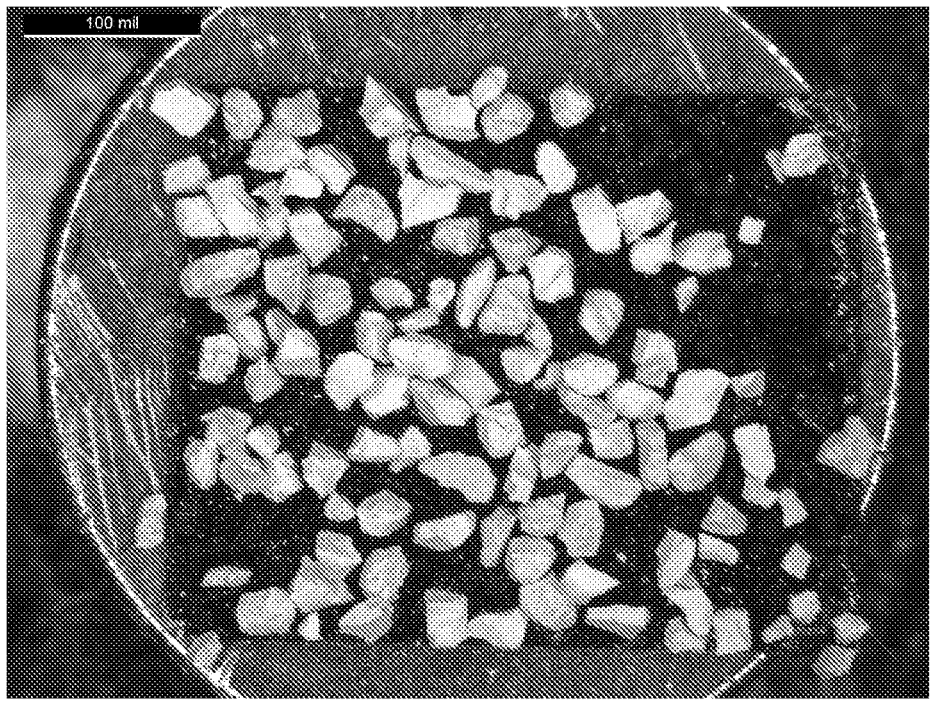
FIG. 2E is an image of activated molybdenum powders, taken by an OMAX 40X-2500X LED Digital Trinocular Microscope.

Compositions provided in the present disclosure utilize an activated form of the metals described herein. An "activated" metal (i.e., a metal that is in an activated state or form), as used herein, refers to a metal that has been subjected to certain conditions and/or otherwise achieves a state demonstrated (in the present disclosure) to increase anti-pathogen activity. Such activated metals have a different conformation than then metal atom prior to activation. For example, as illustrated in the examples below, molybdenum, prior to activation take a shape as seen in FIG. 1A and 1B. After being subjected to activation conditions, however, molybdenum takes a shape as seen in FIG. 2A, 2B, and 2C. Once in the form as seen in FIG. 2A, 2B, and 2C, the activated molybdenum is more effective at neutralizing pathogens when exposed either in solid form (i.e., when the pathogen is exposed to the molybdenum on a dry surface), or when exposed in a liquid form (i.e., when the pathogen is exposed to the molybdenum in a liquid solution or suspension). The activation process described herein further improved the anti-pathogen properties of metals already in oxidized form. For example, as described in the examples below, $MoO_3$, a form of Mo(VI), when subjected to certain activation conditions described herein, demonstrates improved anti-pathogen properties as compared to $MoO_3$ without activation.

As described herein, in some embodiments, the present disclosure provides anti-pathogen compositions (e.g., solid compositions or liquid compositions, including suspensions) comprising an active component, wherein the active component comprises at least one transition metal or transition metal oxide. In some embodiments, at least one transition metal or transition metal oxide is selected from Mo, Zn, Cu, Au, Ag, or an oxide thereof. In some embodiments, at least one transition metal or transition metal oxide is selected from Cu, Au, Ag, or an oxide thereof. In some embodiments, at least one transition metal or transition metal oxide is selected from Mo, Zn, or an oxide thereof. In some embodiments, at least one transition metal or transition metal oxide is Mo or an oxide thereof. In some embodiments, at least one transition metal or transition metal oxide is Zn or an oxide thereof. In some embodiments, at least one transition metal or transition metal oxide is Cu or an oxide thereof. In some embodiments, at least one transition metal or transition metal oxide is Au or an oxide thereof. In some embodiments, at least one transition metal or transition metal oxide is Ag or an oxide thereof.

In some embodiments, at least one transition metal or transition metal oxide is Mo(IV), Mo(V), Mo(VI), Zn(II), Cu(I), Cu(II), Au(I), Au(III), or Ag(I). In some embodiments, at least one transition metal or transition metal oxide is Cu(I), Cu(II), Au(I), Au(III), or Ag(I). In some embodiments, at least one transition metal or transition metal oxide is Mo (IV), Mo(V), Mo(VI), or Zn(II). In some embodiments, at least one transition metal or transition metal oxide is Mo (IV), Mo(V), or Mo(VI). In some embodiments, at least one transition metal or transition metal oxide is Mo(IV). In some embodiments, at least one transition metal or transition metal oxide is Mo(V). In some embodiments, at least one transition metal or transition metal oxide is Mo(VI). In some embodiments, at least one transition metal or transition metal oxide is Zn(II). In some embodiments, at least one transition metal or transition metal oxide is Cu(I) or Cu(II). In some embodiments, at least one transition metal or transition metal oxide is Cu(I). In some embodiments, at least one transition metal or transition metal oxide is Cu(II). In some embodiments, at least one transition metal or transition metal oxide is Au(I) or Au(III). In some embodiments, at least one transition metal or transition metal oxide is Au(I). In some embodiments, at least one transition metal or transition metal oxide is Au(III). In some embodiments, at least one transition metal or transition metal oxide is Ag(I).

In some embodiments, at least one transition metal or transition metal oxide is Mo, $MoO_2$, $MoO_3$, $Mo_2O_6$, $H_2MoO_5$, Zn, ZnO, Cu, $Cu_2O$, CuO, Au, $Au_2O$, $Au_2O_3$, Ag, or $Ag_2O$. In some embodiments, at least one transition metal or transition metal oxide is Cu, $Cu_2O$, CuO, Au, $Au_2O$, $Au_2O_3$, Ag, or $Ag_2O$. In some embodiments, at least one transition metal or transition metal oxide is Mo, $MoO_2$, $MoO_3$, $Mo_2O_6$, $H_2MoO_5$, Zn, or ZnO. In some embodiments, at least one transition metal or transition metal oxide is Mo, $MoO_2$, or $MoO_3$. In some embodiments, at least one transition metal or transition metal oxide is Mo or $MoO_3$. In some embodiments, at least one transition metal or transition metal oxide is Mo. In some embodiments, at least one transition metal or transition metal oxide is $MoO_2$. In some embodiments, at least one transition metal or transition metal oxide is $MoO_3$. In some embodiments, at least one transition metal or transition metal oxide is Zn or ZnO. In some embodiments, at least one transition metal or transition metal oxide is Zn. In some embodiments, at least one transition metal or transition metal oxide is ZnO. In some embodiments, at least one transition metal or transition metal oxide is Cu, $Cu_2O$, or CuO. In some embodiments, at least one transition metal or transition metal oxide is Cu or CuO. In some embodiments, at least one transition metal or transition metal oxide is Cu. In some embodiments, at least one transition metal or transition metal oxide is $Cu_2O$. In some embodiments, at least one transition metal or transition metal oxide is CuO. In some embodiments, at least one transition metal or transition metal oxide is Au, $Au_2O$, or $Au_2O_3$. In some embodiments, at least one transition metal or transition metal oxide is Au or $Au_2O_3$. In some embodiments, at least one transition metal or transition metal oxide is Au. In some embodiments, at least one transition metal or transition metal oxide is $Au_2O$. In some embodiments, at least one transition metal or transition metal oxide is $Au_2O_3$. In some embodiments, at least one transition metal or transition metal oxide is Ag or $Ag_2O$. In some embodiments, at least one transition metal or transition metal oxide is Ag. In some embodiments, at least one transition metal or transition metal oxide is $Ag_2O$.

As described herein, a transition metal or transition metal oxide, once activated, can change crystal structure as compared to the unactivated form. For example, in some embodiments, a transition metal oxide can have an orthorhombic crystal structure. In some embodiments, at least one activated metal is Mo, or an oxide thereof, having an orthorhombic crystal structure.

The activated metals described herein can be in the form of a solid metal (e.g., a plate) or in particle form (e.g., a microparticle or a nanoparticle). As used herein, a "microparticle" is a particle that is between 1 and 1000 μm in size. As used herein, a "nanoparticle" is a particle that is between 1 and 1000 nm in size. The particles of a transition metal or transition metal oxide can be used in solid compositions or liquid suspensions, as described herein.

In some embodiments, particles of at least one active metal are microparticles having a size of about 1 μm to about 1000 μm. In some embodiments, particles of at least one active metal are microparticles having a size of about 45 μm to about 1000 μm. In some embodiments, particles of at least one active metal are microparticles having a size of about 50 μm to about 1000 μm. In some embodiments, particles of at least one active metal are microparticles having a size of about 75 μm to about 1000 μm. In some embodiments, particles of at least one active metal are microparticles having a size of about 100 μm to about 1000 μm. In some embodiments, particles of at least one active metal are microparticles having a size of about 1 μm to about 100 μm. In some embodiments, particles of at least one active metal are microparticles having a size of about 10 μm to about 85 μm. In some embodiments, particles of at least one active metal are microparticles having a size of about 10 μm to about 50 μm. In some embodiments, particles of at least one active metal are microparticles having a size of about 20 μm to about 50 μm. In some embodiments, particles of at least one active metal are microparticles having a size of about 30 μm to about 50 μm. In some embodiments, particles of at least one active metal are microparticles having a size of about 40 μm to about 50 μm. In some embodiments, particles of at least one active metal are microparticles having a size of about 40 μm to about 45 μm. In some embodiments, particles of at least one active metal are microparticles having a size of about 30 μm, about 31 μm, about 32 μm, about 33 μm, about 34 μm, about 35 μm, about 36 μm, about 37 μm, about 38 μm, about 39 μm, about 40 μm, about 41 μm, about 42 μm, about 43 μm, about 44 μm, about 45 μm, about 46 μm, about 47 μm, about 48 μm, about 49 μm, or about 50 μm.

In some embodiments, particles of at least one active metal are nanoparticles having a size of about 1 nm to about 1000 nm. In some embodiments, particles of at least one active metal are nanoparticles having a size of about 500 nm to about 1000 nm. In some embodiments, particles of at least one active metal are nanoparticles having a size of about 1 nm to about 500 nm. In some embodiments, particles of at least one active metal are nanoparticles having a size of about 1 nm to about 100 nm. In some embodiments, particles of at least one active metal are nanoparticles having a size of about 10 nm to about 85 nm. In some embodiments, particles of at least one active metal are nanoparticles having a size of about 10 nm to about 50 nm. In some embodiments, particles of at least one active metal are nanoparticles having a size of about 20 nm to about 50 nm. In some embodiments, particles of at least one active metal are nanoparticles having a size of about 30 nm to about 50 nm. In some embodiments, particles of at least one active metal are nanoparticles having a size of about 40 nm to about 50 nm. In some embodiments, particles of at least one active metal are nanoparticles having a size of about 40 nm to about 45 nm. In some embodiments, particles of at least one active metal are nanoparticles having a size of about 30 nm, about 31 nm, about 32 nm, about 33 nm, about 34 nm, about 35 nm, about 36 nm, about 37 nm, about 38 nm, about 39 nm, about 40 nm, about 41 nm, about 42 nm, about 43 nm, about 44 nm, about 45 nm, about 46 nm, about 47 nm, about 48 nm, about 49 nm, or about 50 nm.

In some embodiments, at least one active metal (e.g., molybdenum) is or comprises an ionic form of the metal (e.g., ionic molybdenum). For example, in some embodiments, Mo loses electron(s) (e.g., becomes positively charged, for example, is a cationic molybdenum ion) or oxidizes once active and thereby becomes ionic, which makes Mo a cation in the formation of an ionic bond with a negatively charged anion (for example, with a non-metal anion). In some embodiments, an active metal has a charge state (i.e., an oxidation state) that is +1, +2, +3, +4, +5, or +6. In some embodiments, at least one active metal is molybdenum having a charge state that is +2, +3, +4, +5, or +6. In some embodiments, at least one active metal is molybdenum having a charge state that is +2, +4, or +6. In some embodiments, at least one active metal is molybdenum having a charge state that is +2. In some embodiments, at least one active metal is molybdenum having a charge state that is +4. In some embodiments, at least one active metal is molybdenum having a charge state that is +6.

It is understood that, as described herein, an active metal having a charge state can either be dissociated (e.g., be ionic in a solution), or associated with one or more suitable counterions. For example, molybdenum having a +4 charge state useful in embodiments described herein can be in the form of $Mo^{+4}$ as a dissociated ion, or, when associated with one or more counterions, could be in the form of $MoO_2$, $H_2MoO_5$, including hydrates thereof. A person of skill in the art would understand suitable counterions useful for creating a chemically stable active metal for various charge states of metals reported herein.

The activated metals of the present disclosure are sufficiently anti-pathogenic such that they can have sufficiently anti-pathogenic properties with small amounts of activated metal. For example, in some embodiments, an anti-pathogen composition comprises from about 1 mg to about 1 g of activated metal. In some embodiments, an anti-pathogen composition comprises from about 1 mg to about 50 mg of activated metal. In some embodiments, an anti-pathogen composition comprises from about 1 mg to about 25 mg of activated metal. In some embodiments, an anti-pathogen composition comprises from about 1 mg to about 5 mg of activated metal. In some embodiments, an anti-pathogen composition comprises about 1 mg of activated metal.

Solid Compositions

As described above, the present disclosure provides, among other things, an anti-pathogen solid composition comprising an active component, wherein the active component comprises particles (e.g., ionic particles, microparticles or nanoparticles) of at least one activated metal. In some embodiments, the present disclosure provides anti-pathogen solid compositions comprising an active component, wherein the active components comprises particles (e.g., ionic particles, microparticles or nanoparticles) of an active metal evenly dispersed throughout the solid composition. In some embodiments, an anti-pathogen solid composition comprises an active component, wherein the active component comprises particles (e.g., ionic particles, microparticles or nanoparticles) of at least one activated metal evenly dispersed throughout the solid composition.

As described herein, a solid composition is or comprises a metal composition. In some embodiments, a metal composition is or comprises a stainless steel composition. For example, in some embodiments, a stainless steel can be in austenitic, ferritic, martensitic, and duplex forms. Different types of stainless steel are determined by their metallurgic phases present in their microscopic structures.

In some embodiments, a stainless steel composition is an austenitic stainless steel. In some embodiments, an austenitic stainless steel comprises chromium, nickel, and iron. In some embodiments, a stainless steel is an austenitic stainless steel comprising about 16% to about 26% by weight of chromium, about 0% to about 35% by weight of nickel, and iron (for the weight of the stainless steel component of the solid composition). In some embodiments, an austenitic stainless steel further comprises alloying elements (e.g. molybdenum).

In some embodiments, a stainless steel composition is a ferritic stainless steel. In some embodiments, a ferritic stainless steel comprises chromium and iron. In some embodiments, a ferritic stainless steel comprises about 10% to about 30% by weight of chromium, and iron. In some embodiments, a ferritic stainless steel may be essentially nickel-free.

In some embodiments, a stainless steel composition is a martensitic stainless steel. In some embodiments, a martensitic stainless comprises carbon, chromium, and iron. In some embodiments, a martensitic stainless steel comprises about 0.1% to about 2% by weight of carbon, about 10% to about 18% by weight of chromium, and iron.

In some embodiments, a stainless steel composition is a duplex stainless steel. In some embodiments, a duplex stainless steel comprises chromium, nickel, molybdenum, copper, and iron. In some embodiments, a duplex stainless steel comprises about 18% to about 30% by weight of chromium, about 0% to about 10% by weight of nickel, about 0% to about 5% by weight of molybdenum, copper, and iron.

In some embodiments, a stainless steel composition is or comprises a metal alloy comprising iron and chromium. In some embodiments, a stainless steel composition is or comprises a metal alloy comprising chromium. In some embodiments, a stainless steel composition comprises about 10.5% to about 50% by weight of chromium. In some embodiments, a stainless steel composition comprises about 10.5%, about 11%, about 11.5%, about 12%, about 12.5%, about 13%, about 13.5%, about 14%, about 14.5%, about 15%, about 15.5%, about 16%, about 16.5%, about 17%, about 17.5%, about 18%, about 18.5%, about 19%, about 19.5%, about 20%, about 21%, about 22%, about 23%, about 24%, about 25%, about 26%, about 27%, about 28%, about 29%, about 30%, about 31%, about 32%, about 33%, about 34%, about 35%, about 36%, about 40%, about 45%, or about 50% by weight of chromium. In some embodiments, a stainless steel composition is or comprises a metal alloy comprising iron. In some embodiments, a stainless steel composition comprises about 50% to about 90% by weight of iron. In some embodiments, a stainless steel comprises about 90%, about 85%, about 80%, about 75%, about 70%, about 65%, about 60%, about 55%, or about 50% by weight of iron.

In some embodiments, a stainless steel composition comprises additional elements. In some embodiments, a stainless steel composition comprises additional elements selected from nickel, molybdenum, nitrogen, copper, carbon, titanium, niobium, zirconium, sulfur, cerium, manganese, silicon, or some combination thereof In some embodiments, a stainless steel composition comprises about 0% to about 40% by weight of additional elements (e.g., nickel, molybdenum, nitrogen, copper, carbon, titanium, niobium, zirconium, sulphur, cerium, manganese, silicon, or combinations thereof). In some embodiments, a stainless steel comprises about 0%, about 0.5%, about 1%, about 1.5%, about 2%, about 2.5%, about 3%, about 3.5%, about 4%, about 4.5%, about 5%, about 6%, about 7%, about 8%, about 9%, about 10%, about 15%, about 20%, about 25%, about 30%, about 35%, or about 40% by weight of additional elements (e.g., nickel, molybdenum, nitrogen, copper, carbon, titanium, niobium, zirconium, sulphur, cerium, manganese, silicon, or combinations thereof).

In some embodiments, a solid composition is or comprises a stainless steel composition and an active component, wherein the active component is or comprises particles (e.g., ionic particles, microparticles, nanoparticles) of an activated metal (e.g., molybdenum), and wherein the stainless steel composition comprises about 0.1% to about 15% by weight of the active component. In some embodiments, a solid composition is or comprises a stainless steel composition and an active component, wherein the stainless steel composition comprises about 4% to about 15% by weight of the active component. In some embodiments, a solid composition is or comprises a stainless steel composition and an active component, wherein the stainless steel composition comprises about 5% to about 10% by weight of the active component. In some embodiments, a solid composition is or comprises a stainless steel composition and an active component, wherein the stainless steel composition comprises about 3%, about 4%, about 5%, about 6%, about 7%, about 8%, about 9% or about 10% by weight of the active component.

In some embodiments, a solid composition is or comprises a stainless steel composition and an active component, wherein an active component comprises an activated metal dispersed throughout the solid composition. In some embodiments, an activated metal is evenly distributed throughout the solid composition. In some embodiments, an activated metal is selectively distributed (i.e., only located in specific parts of) in the solid composition.

In some embodiments, the present disclosure provides a solid composition comprising a stainless steel composition and an active component, wherein the active component comprises particles (e.g., ionic particles, microparticles, nanoparticles) of an activated metal. In some embodiments, the solid composition comprises a stainless steel composition and an active component comprising microparticles of an activated metal. In some embodiments, the active component comprises microparticles of an activated metal that are about 10 to about 1000 µm in size (e.g., about 10 µm to about 100 µm in size; about 30 µm to about 100 µm in size; about 40 to about 60 µm in size; about 40 to about 50 µm in size). In some embodiments, the active component comprises microparticles of an activated metal that are about 10 to about 1000 µm in size, and wherein the solid composition comprises 3% or greater by weight of an active component.

In some embodiments, solid compositions described herein are distinct from previously reported stainless steel compositions comprising e.g., molybdenum (e.g., stainless steel 316) at least because previously reported stainless steel compositions do not comprise microparticles (or nanoparticles) of molybdenum. Previously provided solid compositions comprising stainless steel are produced by melting all metals (including molybdenum) together to provide a molten mixture, which is then poured into the mold. In some embodiments of the present disclosure, in contrast, solid compositions comprising stainless steel and an active component comprising an active metal are produced by preparing a molten mixture of all metals except the active metal as part of the active component; then adding the active component such that the active metal does not melt and retains its size (e.g., microparticle or nanoparticle size). Such a process provides, in some embodiments, a solid composition comprising a stainless steel and active component, wherein the active component is dispersed as microparticles or nanoparticles throughout the stainless steel of the solid composition.

In some embodiments, a stainless steel further comprises an antioxidizing agent. In some embodiments, an antioxidizing agent is a silicon antioxidizing agent.

In some embodiments, a solid composition comprises an active component, wherein the active component comprises particles of an active metal that have been sputtered (e.g., sprayed) onto the solid composition, thereby coating either the active component or the solid composition itself with the active metal.

In some embodiments, a solid composition comprises an active component, wherein the active component comprises particles of an active metal that have been selectively applied to the solid composition. For example, in some embodiments, in some embodiments, a solid composition comprises an active component comprising particles (e.g., microparticles, nanoparticles) of an active metal, wherein the active component has been applied (e.g., painted, sprayed, layered, etc.) onto less than all of the solid composition.

An additional benefit of the compositions reported herein in that, in some embodiments, a solid composition or liquid suspension uses less active metal to achieve an anti-pathogen effect as compared to other metals or previous compositions. For example, in some embodiments, an anti-pathogen solid composition comprises about 0.1% to about 99% by weight of an active component. In some embodiments, an anti-pathogen solid composition comprises about 0.1% to about 75% by weight of an active component. In some embodiments, an anti-pathogen solid composition comprises about 0.1% to about 50% by weight of an active component. In some embodiments, an anti-pathogen solid composition comprises about 0.1% to about 25% by weight of an active component. In some embodiments, an anti-pathogen solid composition comprises about 0.1% to about 10% by weight of an active component. In some embodiments, an anti-pathogen solid composition comprises about 0.1% to about 5% by weight of an active component. In some embodiments, an anti-pathogen solid composition comprises about 0.1% to about 3% by weight of an active component. In some embodiments, an anti-pathogen solid composition comprises about 0.1% to about 2% by weight of an active component. In some embodiments, an anti-pathogen solid composition comprises about 0.1% to about 0.5% by weight of an active component. In some embodiments, an anti-pathogen solid composition comprises about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, or 5% by weight of an active component.

As used herein, the term "about", in reference to a number or percentage, is intended to include numbers that fall within a certain range around that number (where the number is real, i.e., does not go below 0% or above 100%). For example, the term about is intended to encompass ±0.2%, ±0.5%, ±1%, ±5%, or ±10% with respect to any indicated number.

The compositions of the present disclosure can further comprise a second metal or metal oxide. For example, in some embodiments, an anti-pathogen solid composition further comprises a second metal selected from Ni, Zn, Mn, Cu, Au, Ag, Sn, and Pd, or oxides thereof. In some embodiments, a second metal is Ni. In some embodiments, a second metal is Pd. In some embodiments, a second metal is Sn. In some embodiments, a second metal is Ag. In some embodiments, a second metal is Au. In some embodiments, a second metal is Cu. In some embodiments, a second metal is Mn. In some embodiments, a second metal is Zn or ZnO. In some embodiments, a second metal is Zn. In some embodiments, a second metal is ZnO.

In some embodiments, an anti-pathogen composition comprises about 0.1% to about 99% by weight of the second metal. In some embodiments, an anti-pathogen solid composition comprises about 0.1% to about 75% by weight of the second metal. In some embodiments, an anti-pathogen solid composition comprises about 0.1% to about 50% by weight of the second metal. In some embodiments, an anti-pathogen solid composition comprises about 0.1% to about 15% by weight of the second metal. In some embodiments, an anti-pathogen solid composition comprises about 0.1% to about 5% by weight of the second metal. In some embodiments, an anti-pathogen solid composition comprises about 0.1% to about 3% by weight of the second metal. In some embodiments, an anti-pathogen solid composition comprises about 0.1% to about 1% by weight of the second metal.

In some embodiments, an anti-pathogen composition (e.g., a solid composition described herein) further comprises an antioxidant. In some embodiments, an antioxidant is selected from pentaerythritol tetrakis[3-[3,5 -di-tert-butyl-4-hydroxyphenyl]propionate (Irganox® 1010) and tris(2,4-di-tert.-butylphenyl)phosphite. (Irgafos® 168). In some embodiments, an antioxidant is selected from those provided in Table 2.1 on pages 15-16 in M. Tolinski, *Additives for Polyolefins*, $2^{nd}$ ed. 2015.

Solid compositions provided herein comprise one or more materials selected from plastics, polymers, biopolymers/biocomposites, ceramics, rubbers, paints, ointments, glasses, silicones, papers, fabric, metal, and combinations thereof, where the active component is evenly distributed as particles throughout the solid composition. As will be understood by those skilled in the art, incorporation of such particles into a solid composition (e.g., by even distribution, by patterned distribution, by random distribution, or otherwise as described herein) can be useful in accordance with the present disclosure, and in particular can achieve anti-pathogen character to such solid composition—e.g., to surfaces (e.g., contact surfaces) thereof.

In some embodiments, said solid compositions can be formed into numerous shapes having suitable hardness and stability such that they can be used for product manufacture, for example as described below. Furthermore, in some embodiments, certain said solid compositions can be shaped into a flexible surface coating, for example to thereby provide an anti-pathogen coating.

In some embodiments, a solid composition described herein comprises a polymer. In some embodiments, the polymer is selected from polypropylenes, polystyrenes, polyethylenes, polyesters, polycarbonates, polyurethanes, polyvinyls (e.g., polyvinylchlorides), and combinations thereof. In some embodiments, the polymer is a polypropylene. In some embodiments, the polymer is a polyethylene. In some embodiments, the polymer is a polycarbonate. In some embodiments, the polymer is a polyester. In some embodiments, the polymer is a polystyrene. In some embodiments, the polymer is a polyurethane.

In some embodiments, a solid composition comprises a biopolymer/biocomposite. In some embodiments, a solid composition comprises an organic biocomposite or inorganic biocomposite. In some embodiments, a solid composition comprises an organic biocomposite. In some embodiment, an organic biocomposite is or comprises sodium alginate/silk fibroin, starch/lignin, poly(lactic acid)/lignocellulosic fiber, starch/polyvinyl acetate/cellulose, chitosan/sisal cellulose or combinations thereof. In some embodiments, a solid composition comprises an inorganic biocomposite. In some embodiments, a solid composition is an inorganic biocomposite. In some embodiments, an inorganic biocomposite is or comprises comprise hydroxyapatite (HAp)/carbon nantobue (CNT)/Ag, HAp/titania rods, or HAp/alumina/zirconia, or combinations thereof.

As described herein, the present disclosure provides solid anti-pathogen compositions comprising about 0.01% to about 5% by weight of an active component, wherein the active component comprises particles (e.g., ionic particles, microparticles or nanoparticles) of an activated transition metal or transition metal oxide; and about 1% to about 99.99% by weight of a polymer. In some embodiments, a solid anti-pathogen composition comprises about 0.01% to about 10% by weight of an active component; and about 50% to about 99.99% by weight of a polymer. In some embodiments, a solid anti-pathogen composition comprises about 0.01% to about 5% by weight of an active component; and about 50% to about 99.99% by weight of a polymer. In some embodiments, a solid anti-pathogen composition comprises about 0.01% to about 5% by weight of an active component; and about 75% to about 99.99% by weight of a polymer. In some embodiments, a solid anti-pathogen composition comprises about 0.01% to about 5% by weight of an active component; and about 90% to about 99.99% by weight of a polymer. In some embodiments, a solid anti-pathogen composition comprises about 0.01% to about 4% by weight of an active component; and about 1% to about 99.99% by weight of a polymer. In some embodiments, a solid anti-pathogen composition comprises about 0.01% to about 3% by weight of an active component; and about 1% to about 99.99% by weight of a polymer. In some embodiments, a solid anti-pathogen composition comprises about 0.01% to about 2% by weight of an active component; and about 1% to about 99.99% by weight of a polymer. In some embodiments, a solid anti-pathogen composition comprises about 0.01% to about 1% by weight of an active component; and about 1% to about 99.99% by weight of a polymer. In some embodiments, a solid anti-pathogen composition comprises about 0.01% to about 3% by weight of an active component; and about 80% to about 99.99% by weight of a polymer. In some embodiments, a solid anti-pathogen composition comprises about 0.01% to about 3% by weight of an active component; and about 90% to about 99.99% by weight of a polymer.

As described herein, the present disclosure provides solid anti-pathogen compositions comprising about 0.01% to about 5% by weight of an active component, wherein the active component comprises particles (e.g., ionic particles, microparticles or nanoparticles) of an activated transition metal or transition metal oxide; and about 1% to about 99.99% by weight of stainless steel. In some embodiments, a solid anti-pathogen composition comprises about 0.01% to about 10% by weight of an active component; and about 50% to about 99.99% by weight of stainless steel. In some embodiments, a solid anti-pathogen composition comprises about 0.01% to about 5% by weight of an active component; and about 50% to about 99.99% by weight of stainless steel. In some embodiments, a solid anti-pathogen composition comprises about 0.01% to about 5% by weight of an active component; and about 75% to about 99.99% by weight of stainless steel. In some embodiments, a solid anti-pathogen composition comprises about 0.01% to about 5% by weight of an active component; and about 90% to about 99.99% by weight of stainless steel. In some embodiments, a solid anti-pathogen composition comprises about 0.01% to about 4% by weight of an active component; and about 1% to about 99.99% by weight of stainless steel. In some embodiments, a solid anti-pathogen composition comprises about 0.01% to about 3% by weight of an active component; and about 1% to about 99.99% by weight of stainless steel. In some embodiments, a solid anti-pathogen composition comprises about 0.01% to about 2% by weight of an active component; and about 1% to about 99.99% by weight of stainless steel. In some embodiments, a solid anti-pathogen composition comprises about 0.01% to about 1% by weight of an active component; and about 1% to about 99.99% by weight of stainless steel. In some embodiments, a solid anti-pathogen composition comprises about 0.01% to about 3% by weight of an active component; and about 80% to about 99.99% by weight of stainless steel. In some embodiments, a solid anti-pathogen composition comprises about 0.01% to about 3% by weight of an active component; and about 90% to about 99.99% by weight of stainless steel.

In some embodiments, a solid composition comprising stainless steel is further subjected to surface preparation and/or finishing (e.g., sanding, polishing, or chemical scrubbing). Without being bound by theory, it is believed that enhancing exposure of an active to a pathogen increases anti-pathogenic activity. Further, without being bound by theory, it is believed that surface finishing may make certain solid compositions, e.g., a stainless steel composition, easier to clean, provide better corrosion resistance, as well as facilitate further manufacturing steps.

In some embodiments, a surface of a solid composition (e.g., a stainless steel composition) is finished by hot rolling, annealing, and descaling, to thereby produce a dull finish. In some embodiments, a surface of a solid composition (e.g., a stainless steel composition) is finished by hot rolling, followed by cold rolling (e.g., on polished rolls), to thereby produce a bright finish. In some embodiments, a surface of a solid composition (e.g., a stainless steel composition) is finished by cold rolling in combination with annealing, grinding (e.g., with abrasives), or buffing (e.g., a finely ground surface), to thereby produce a highly reflective finish. In some embodiments, a surface of a solid composition (e.g., a stainless steel composition) is finished by polishing (e.g., with progressively finer abrasives), followed by buffing, to thereby produce a mirror finish. In some embodiments, a surface of a solid composition (e.g., a stainless steel composition) is finished by tumbling, dry etching, wet etching, and/or surface dulling (e.g., sandblasting, wire brushing, or pickling).

In some embodiments, a solid composition is subjected to post-production finishing. In some embodiments, post-production finishing of a solid composition comprises pickling and/or passivation of the solid composition. For example, in some embodiments, pickling and/or passivation comprises chemical finishing of a solid composition described herein to thereby protect a metal from, e.g., rust. In some embodiments, pickling and/or passivation comprises submerging a solid composition in a bathing liquid that removes imperfections and rust from the surface of metal. In some embodiments, a process of picking and/or passivation comprises contacting a solid composition with an acid (e.g., a nitric acid, a citric acid, sulfuric acid, etc.), or a peroxide (e.g., $H_2O_2$).

Solid anti-pathogen compositions described herein can neutralize microbes or pathogens on contact. For example, in some embodiments, anti-pathogen solid compositions neutralize microbes or pathogens selected from a *micrococcus, staphylococcus, bacillus, pseudomonas, legionella, salmonella, listeria, clostridium perfringens, Escherichia coli*, coronaviruses, rhinoviruses, influenza, adenovirus, parainfluenza, respiratory syncytial virus, and enterovirus. In some embodiments, a microbe or pathogen is a *staphylococcus* (including, e.g., methicillin-*staphylococcus aureus* (MRSA)), *legionella*, an influenza, *E. coli*, or a coronavirus (including SARS-CoV-2).

Liquid Compositions

As described herein, the present disclosure provides anti-pathogen compositions that are suspensions or solutions (e.g., a homogeneous solution) in water (e.g., tap water or distilled water) or saline comprising an active component, wherein the active component comprises particles (e.g., ionic particles, microparticles, or nanoparticles) or ionic liquid (e.g., a class of non-flammable and non-volatile solvents, which comprises two entities of opposite charge, a cation (e.g., activated molybdenum) and an anion) of at least one activated metal. Anti-pathogen compositions in suspension or solution in water or saline are also found to neutralize pathogens upon contact. Such compositions are sufficiently acidic such that substantially all (e.g., 90% or greater) of pathogens are neutralized within the solution. For example, in some embodiments, an anti-pathogen liquid composition has a pH of about 5.5 or less. In some embodiments, an anti-pathogen liquid composition has a pH of about 4.0 or less. In some embodiments, an anti-pathogen liquid composition has a pH of about 3.5 or less. In some embodiments, an anti-pathogen liquid composition has a pH of about 3.0 or less. In some embodiments, an anti-pathogen liquid composition has a pH of about 2.5 or less. In some embodiments, an anti-pathogen liquid composition has a pH of about 2.0 or less. In some embodiments, an anti-pathogen liquid composition has a pH of about 1.9 or less. In some embodiments, an anti-pathogen suspension has a pH of about 1.85 or less. In some embodiments, an anti-pathogen liquid composition has a pH of about 1.75 or less. In some embodiments, an anti-pathogen liquid composition has a pH of about 1.65 or less. In some embodiments, an anti-pathogen liquid composition has a pH of about 1.5 or less.

In some embodiments, an acid is added to liquid compositions described herein to achieve a desired pH (e.g., a pH described above). In some embodiments, a liquid composition comprises a glacial acetic acid.

In some embodiments, a weight ratio of an activated metal to saline solution in an anti-pathogen liquid composition is from about 1:100 to about 1:1. In some embodiments, the weight ratio of an activated metal to water or saline in an anti-pathogen liquid composition is from about 1:100 to about 1:25. In some embodiments, the weight ratio of an activated metal to saline solution in an anti-pathogen liquid composition is from about 1:100 to about 1:50. In some embodiments, the weight ratio of an activated metal to saline solution in an anti-pathogen liquid composition is from about 1:100 to about 1:75. In some embodiments, the weight ratio of an activated metal to saline solution in an anti-pathogen liquid composition is from about 1:100 to about 1:80. In some embodiments, the weight ratio of an activated metal to saline solution in an anti-pathogen liquid composition is from about 1:100 to about 1:85. In some embodiments, the weight ratio of an activated metal to saline solution in an anti-pathogen liquid composition is from about 1:100 to about 1:90. In some embodiments, the weight ratio of an activated metal to saline solution in an anti-pathogen liquid composition is from about 1:100 to about 1:95.

Anti-pathogen liquid compositions described herein are useful in a variety of sanitization methods, including, for example, as anti-pathogens for solid surfaces (e.g., as an aerosol and/or as a spray delivered from a spray bottle, a mist, a fogger, and the like that can be sprayed or applied to a solid surface). In some embodiments, the present disclosure provides a method for neutralizing microbes or pathogens on a surface, the method comprising a step of contacting the surface with an anti-pathogen liquid composition described herein. In some embodiments, the surface is human skin.

In some embodiments, a microbe or pathogen is selected from a *micrococcus, staphylococcus, bacillus, pseudomonas, legionella, salmonella, listeria, clostridium perfringens, Acinetobacter baumannii, Escherichia coli*, coronaviruses, rhinoviruses, influenza, adenovirus, parainfluenza, respiratory syncytial virus, and enterovirus. In some embodiments, a microbe or pathogen is a *staphylococcus* (including, e.g., methicillin-*staphylococcus aureus* (MRSA)), *legionella*, an influenza, *E. coli*, or a coronavirus (including SARS-CoV-2).

Coatings and Fabrics

In some embodiments, an anti-pathogen liquid composition described herein comprises water and complex of an active component and a polymer. In some embodiments, an anti-pathogen liquid composition comprises water and an active component comprising an activated metal, and a polymer. In some embodiments, a polymer is a copolymer. In some embodiments, a polymer is a tri-block copolymer.

In some embodiments, an anti-pathogen liquid composition is made by coating or adding an active component (e.g., Mo cations) to a polymer. In some embodiments, an anti-pathogen liquid composition is made by activating a component (e.g., Mo powder), followed by adding an active component to a polymer. For example, an anti-pathogen liquid composition is made by placing a sample (e.g., fabrics, plastics, metals, etc.) in a container, followed by covering the sample with an appropriate amount (e.g., 1-1000 μm) of metal powder (e.g. Mo powder), and then adding about 1% to about 35% $H_2O_2$ to activate the metal powder (e.g. Mo powder) directly in the presence of the sample. Without being bound by theory, it is understood that a resultant heat (delta T) induces infiltration and binding of the now activated component (e.g., Mo) onto the surface of the sample.

In some embodiments, a polymer has an average molecular weight of about 1,000,000 or less. In some embodiments, a polymer has an average molecular weight of about 500,000 or less. In some embodiments, a polymer has an average molecular weight of about 100,000 or less. In some embodiments, a polymer has an average molecular weight of about 50,000 or less. In some embodiments, a polymer has an average molecular weight of about 10,000 or less. In some embodiments, a polymer has an average molecular weight of about 5,000 or less. In some embodiments, a polymer has an average molecular weight of about 1,000 or less. In some embodiments, a polymer has an average molecular weight of about 1,000 or less. In some embodiments, a polymer has an average molecular weight of about 500 or less.

As described herein, in some embodiments, the present disclosure provides anti-pathogen liquid compositions for treating (e.g., finishing, drying, etc.) fabric. In some embodiments, the present disclosure provides anti-pathogen liquid compositions for finishing fabric. In some embodiments, the present disclosure provides anti-pathogen liquid compositions for drying fabric. In some embodiments, a fabric is selected from any composition, construction, or type. In some embodiments, a fabric is selected from any composition. In some embodiments, a fabric is selected from any construction. In some embodiments, a fabric is selected from any type. For example, in some embodiments, a fabric is selected from a knit material, a woven material, a non-woven material, or combinations thereof. In some embodiments, a fabric is selected from natural fibers (e.g. fibers produced by plants, animals, or geological processes,) synthetic organic fibers, inorganic fibers, or combinations thereof.

In some embodiments, a natural fiber is or comprises silk, cotton, wool, flax, fur, hair, cellulose, ramie, hemp, linen, wood pulp, or combinations thereof.

In some embodiments, a synthetic organic fiber is derived from polyolefins (e.g., polyethylene, polypropylene, or polybutylene), halogenated polymers (e.g., polyvinyl chloride), polyaramids (e.g., poly-p-phenyleneteraphthalamid or poly-m-phenyleneteraphthalamid), melamine and melamine derivatives, polyesters (e.g., polyethylene terephthalate (PET), polyester/polyethers), polyamides (e.g., nylon 6 or nylon 6-6), polyurethanes, acetates, rayon acrylics, or combinations thereof.

In some embodiments, an inorganic is or comprises fiberglass, boron fibers, rock wool, or combinations thereof.

In preferred embodiments, a fabric is selected from cotton, Nylon 6; Nylon 6-6; polypropylene, polyethylene terephthalate, or combinations thereof.

As described herein, the present disclosure provides methods of treating fabric, comprising treating (i.e., contacting, or coating) a fabric with an anti-pathogen liquid composition described herein, followed by drying the fabric to remove moisture and other volatile components. In some embodiments, drying a fabric is or comprises convection drying, contact drying, radiation drying, or combinations thereof to thereby provide a treated fabric.

In some embodiments, a treated fabric is used in a variety of materials to impart anti-pathogen properties. For example, in some embodiments, a treated fabric is used in apparel, apparel interlining, upholstery, carpeting, padding, ceiling tiles, acoustical tiles, backing, wall coverings, roofing products, house wraps, insulation, bedding, wiping cloths, towels, gloves, rugs, floor mats, drapery, napery, textile bags, awnings, vehicle covers, boat covers, tents, agricultural coverings, geotextiles, automotive headliners, filtration media, dust masks, fiber fill, envelopes, tags, labels, diapers, feminine hygiene products (e.g., sanitary napkins, tampons), laundry aids (e.g., fabric dryer-sheets), wound care products, medical care products (e.g., sterile wraps, caps, gowns, masks, drapings), or combinations thereof.

In some embodiments, the amount of an active component comprising an active metal in a fabric is determined by XRF (X-ray fluorescence) spectroscopy. In some embodiments, a treated fabric is analyzed to determine the homogeneity of a treatment. In some embodiments, the amount of a metal (e.g., silver) in a recovered solution was determined by Inductively Coupled Plasma-Atomic Emission Spectrometry (ICP-AES).

Assessment and/or Characterization

In some embodiments, an activated metal, and/or a composition including it, may be characterized and/or assessed for one or more features as described herein.

For example, in some embodiments, ability to sanitize may be assessed. In some embodiments, ability to sanitize may be or include ability to inhibit proliferation of and/or to kill one or more microbes or pathogens as described herein (e.g., *micrococcus, staphylococcus, bacillus, pseudomonas, legionella, salmonella, listeria, clostridium perfringens, Acinetobacter baumannii, Escherichia coli*, coronaviruses, rhinoviruses, influenza, adenovirus, parainfluenza, respiratory syncytial virus, and enterovirus).

In some embodiments, ability to sanitize may be assessed with respect to direct contact—e.g., ability of an activated metal and/or composition as described herein to reduce proliferation and/or to kill one or more microbes or pathogens when contacted with a sample including such microbe(s) or pathogens. Alternatively or additionally, in some embodiments, ability to sanitize may be assessed over a distance—e.g., ability of an activated metal and/or composition as described herein to reduce proliferation and/or to kill one or more microbes or pathogens in a space or area notwithstanding that the activated metal and/or composition may not be in direct contact with the microbe or pathogen.

For example, as described in Example 9, the present disclosure demonstrates that bringing an item in contact with an activated metal or composition containing it, as described herein, can inhibit proliferation of and/or kill one or more microbes or pathogens even on parts of the item that are not in direct contact with the activated metal or composition.

In some embodiments, the anti-pathogenic effect described herein can extend to at least 1 cm, 2 cm, 3 cm, 4 cm, 5 cm, or 6 cm beyond the activated metal. That is, in some embodiments, pathogens and microbes can be neutralized or killed despite not being in direct contact with the activated metal (e.g., being within a 6 cm or less radius). In some embodiments, a surface, e.g., a medical surface, a food preparation or storage surface, or human skin, can be neutralized through proximal contact (e.g., being within a 6 cm or less radius) of an activated metal.

Exemplary Uses

As described above and herein, the compositions described herein have a variety of uses, such as being able to be formed into a variety of shapes for use as a number of household or medical products. In some embodiments, compositions described herein can be flexibly formed into coatings for surfaces, e.g., tables, railings, handles, and the like.

In some embodiments, a composition described herein can be formed into a pouch for sterilizing water. That is, in some embodiments, the present disclosure provides a water-permeable pouch, comprising an active component, wherein the active component is or comprises particles (e.g., microparticles or nanoparticles) of an activated metal. Such a pouch is useful for the sterilization of microbes or pathogens in water. That is, in some embodiments, the present disclosure provides a method of neutralizing microbes or pathogens in a water sample, the method comprising contacting the water sample with a water-permeable pouch described herein for a period of time sufficient to neutralize or sterilize microbes or pathogens in the water sample. Microbes or pathogens, traveling through the pouch and coming into contact with the active component are neutralized, thereby sterilizing the water. In some embodiments, a water-permeable pouch further comprises a pH indicator. In some embodiments, the pH indicator indicates when the water has a pH that is equal to or less than 7. In some embodiments, the pH indicator indicates when the water has a pH that is equal to or less than 5.5. In some embodiments, the pH indicator indicates when the water has a pH that is equal to or less than 2.0.

In some embodiments, a composition described herein can be formed into a filter useful for incorporation into, for example, a mask. The COVID-19 pandemic has caused a shortage of medical masks for professionals having a sufficiently protective grade to protect wearers from spreading or otherwise inhaling SARS-CoV-2. There is a need for a mask having an optionally replaceable filter that is also able to neutralize pathogens or microbes on contact. In some embodiments, the present disclosure provides a face mask configured to be worn over the mouth of a human, wherein the face mask comprises a filter comprising an active component, and wherein the active component comprises particles (e.g., microparticles or nanoparticles) or ionic liquid of an activated metal.

In some embodiments, the present disclosure provides compositions that can be formed into a medical implant. For example, in some embodiments, the a solid composition described herein can be formed into a suture, a mesh, a temporary and permanent metallic alloy implant, a temporary and permanent ceramic alloy implant, a temporary poly lactic acid based implant, a temporary and permanent synthetic polymer implant (including vascular grafts), or a temporary and permanent natural fiber implant.

In some embodiments, a solid composition of the present disclosure can be formed into one or more of reusable metal surgical instruments, plastic single patient use devices, personal protective equipment, e.g., masks as described above, ventilator tubing and anesthesia circuits, ventilators, cardiopulmonary pumps and extracorporeal membrane oxygenators and components, hemodialysis circuits, PICC lines (percutaneously placed vascular access devices constructed from synthetic polymers), handheld scopes, IV lines and poles, sterilization trays, surgical trocars, product packaging, surgical equipment sterile coverings, surgical disposables containers, surgical monitoring electrodes and devices, presurgical covering, surgical tape, surgical gloves, exam gloves, surgical catheters, surgical drains, surgical tubes, colostomy bags, surgical wound dressings for both surgically closed wounds and for open wound management (with or without negative pressure devices), and external stabilization products.

In some embodiments, solid compositions described herein can be used to form one or more of food containers, food transportation crates, food grocery displays, plastics for use with food (including plastic containers), plastic wraps, plastic gloves, cutlery, dishware, foil wrap, appliance interior plastics, computer peripherals, including keyboards and mice, cell phone cases/screen protectors, bathroom counters/fixtures, restaurant menus, flooring, playground equipment, water sterilization system with pH reversal (as described in more detail above).

In some embodiments, solid composition described herein can be used to form one or more of airline-related materials such as trays and other surfaces, steering wheels and other materials in automobiles, touch screens, and dashboards and the like, including similar uses on other forms of public transit (e.g., trains and community bicycles).

In some embodiments, a solid composition described herein can be used to form material for use in clothing.

In some embodiments, a solid composition described herein can be used to form material for use in agriculture, including, for example, seeding, irrigation, plant/crop management, harvesting equipment, and fertilizers.

In some embodiments, a solid composition described herein can be used to form a material for use in industrial settings, including, for example, machine touch pads, covers/shields, cleaning agents, flooring, conveyer belts, and hazardous waste containers.

In some embodiments, a liquid composition described herein can be used in combination with a nebulizer to form an aerosol spray. In some embodiments, the aerosol spray can be used to neutralize pathogens on solid surfaces.

In some embodiments, a liquid composition described herein can be used as a spray, e.g., to be sprayed onto a solid surface via a spray bottle, a mist, a foggers, and the like.

Activation of Metals

The present disclosure also provides methods for activating a metal, e.g., a transition metal or transition metal oxide, as described herein. In some embodiments a method for activating a transition metal or transition metal oxide comprises treating the transition metal or transition metal oxide with one or more of heating, calcination, washing/oxidizing, charging, UV light exposure, and combinations thereof.

For example, in some embodiments, a transition metal or transition metal oxide is activated by exposing the transition metal or transition metal oxide to a temperature of 100° C.-2400° C. for a period of time, e.g., 1 minute to 24 hours.

In some embodiments, a transition metal or transition metal oxide is activated by exposing the transition metal or transition metal oxide to a wash. In some embodiments, the wash is an aqueous oxidation agent. In some embodiments, the wash fluid is a gaseous oxidation agent. In some embodiments, the wash fluid consists of 1-4 parts $H_2O$, 1-4 parts distilled $H_2O$, 1-35% $H_2O_2$ (peroxide), acetylene, oxyacetylene, or combinations thereof.

In some embodiments, a transition metal or transition metal oxide is activated by exposing the transition metal or transition metal oxide to low voltage. The ideal ranges of the voltage and duration of the charging may vary depending on the individual components and aggregate. This pretreatment causes the components to have a specific charge at their surface to further disable and/or kill pathogens.

In some embodiments, a transition metal or transition metal oxide is activated by exposing the transition metal or transition metal oxide to UV light. In some embodiments, the UV light is selected from UVA, UVB, UVC, and combinations thereof. Increased anti-pathogen efficacy has been observed using UV light for zinc oxide nanoparticles and titanium dioxide doped with molybdenum. This pretreatment results in a photocatalytic effect from the active component. The photocatalytic effect is particularly helpful in aqueous and dark environments. In some embodiments, the photocatalytic effect may be used in the brewing industry.

In some embodiments, a metal is activated after being incorporated into any of the solid compositions or liquid compositions described herein. For example, in some embodiments, a solid composition comprises a transition metal or transition metal oxide, which is then subjected to the activation conditions described herein (e.g., washing/ oxidizing, calcination, heating, charging, UV light exposure, and combinations thereof). In some embodiments, a liquid suspension comprises a transition metal or transition metal oxide, which is then subjected to the activation conditions described herein (e.g., washing/oxidizing, calcination, heating, charging, UV light exposure, and combinations thereof).

In some embodiments, a solid composition comprises an active component, wherein the active component comprises an ionic activated metal. In some embodiments, an ionic activated metal refers to metal atoms having a charge state (i.e., a cationic charge) of +1, +2, +3, +4, +5, or +6. For example, an ionic activated metal is or comprises molybdenum particles (e.g., nanoparticles and the like) that have a cationic charge, (e.g., +1, +2, +3, +4, +5, or +6). In some embodiments, an ionic activated metal is or comprises molybdenum particles (e.g., nanoparticles and the like) that are activated (e.g., by exposure to $H_2O_2$).

In some embodiments, an ionic activated metal can be prepared according to methods provided herein. For example, in some embodiments, a method of activating a metal in an ionic form comprises contacting a metal with an oxidizing agent. In some embodiments, the present disclosure provides a method of activating a metal comprising contacting the metal with hydrogen peroxide. In some embodiments, a metal to be activated is described herein, and includes, for example, Mo, Zn, Cu, Ag, and Au. In some embodiments, a metal to be activated is Mo. In some embodiments, the present disclosure provides a metal is activated by contact with $H_2O_2$.

For example, in some embodiments, the washing process may result in sediment, which may be collected and used to activate saline. In some embodiments, methods of producing at least one active metal in an ionic form may further comprise conducting one or more tests on an activated saline using filters having a size of about 1 μm. In some embodiments, sediment having a size of at least about 1 μm, which may comprise microparticles and/or ionic forms may be trapped in the filters. In some embodiments, sediment having a size of 0 to about 1 μm (e.g., nanoparticles) may pass through the filters.

Exemplary Embodiments

Embodiment 1. An anti-pathogen solid composition comprising an active component, wherein the active component comprises particles of at least one activated metal.

Embodiment 2. The anti-pathogen solid composition of Embodiment 1, wherein the at least one activated metal is a transition metal or a transition metal oxide.

Embodiment 3. The anti-pathogen solid composition of Embodiments 1 or 2, wherein the at least one activated metal is selected from Mo, Zn or an oxide thereof.

Embodiment 4. The anti-pathogen solid composition of Embodiment 3, wherein the at least one activated metal is Mo (IV), Mo(V), or Mo(VI), or an oxide thereof.

Embodiment 5. The anti-pathogen solid composition of Embodiment 3, wherein the at least one activated metal is selected from Mo, $MoO_2$, $MoO_3$, $MoO_5$, $Mo_2O_6$, $H_2MoO_5$, Zn, and ZnO.

Embodiment 6. The anti-pathogen solid composition Embodiment 5, wherein the at least one activated metal is Mo, $MoO_2$, $MoO_3$, $H_2MoO_5$, or $Mo_2O_6$.

Embodiment 7. The anti-pathogen solid composition of any one of Embodiments 1-3, wherein the at least one activated metal is Mo, or an oxide thereof, having a cubic, spherical, monoclinic, hexagonal, orthorhombic, tetragonal, triclinic, or rhombohedral crystal structure.

Embodiment 8. The anti-pathogen solid composition of any one of Embodiments 1-7, wherein the anti-pathogen solid composition comprises about 0.1% to about 99% by weight of the active component.

Embodiment 9. The anti-pathogen solid composition of any one of Embodiment 1-8, wherein the anti-pathogen solid composition comprises about 0.1% to about 50% by weight of the active component.

Embodiment 10. The anti-pathogen solid composition of any one of Embodiment 1-9, wherein the anti-pathogen solid composition comprises about 0.1% to about 15% by weight of the active component.

Embodiment 11. The anti-pathogen solid composition of any one of Embodiments 1-10, wherein the anti-pathogen solid composition comprises about 0.1% to about 5% by weight of the active component.

Embodiment 12. The anti-pathogen solid composition of any one of Embodiments 1-11, wherein the anti-pathogen solid composition comprises about 0.1% to about 3% by weight of the active component.

Embodiment 13. The anti-pathogen solid composition of any one of Embodiments 1-12, wherein the anti-pathogen solid composition comprises about 0.1% to about 2% by weight of the active component.

Embodiment 14. The anti-pathogen solid composition of any one of Embodiments 1-13, wherein the anti-pathogen solid composition comprises about 0.1% to about 1% by weight of the active component.

Embodiment 15. The anti-pathogen solid composition of any one of Embodiments 1-14, wherein the particles of the at least one active metal have a size of about 1 μm to about 100 μm.

Embodiment 16. The anti-pathogen solid composition of any one of Embodiments 1-15, wherein the particles of the at least one active metal have a size of about 10 μm to about 85 μm.

Embodiment 17. The anti-pathogen solid composition of any one of Embodiments 1-16, wherein the particles of the at least one active metal have a size of about 10 μm to about 50 μm.

Embodiment 18. The anti-pathogen solid composition of any one of Embodiments 1-17, wherein the particles of the at least one active metal have a size of about 20 μm to about 50 μm.

Embodiment 19. The anti-pathogen solid composition of any one of Embodiments 1-18, wherein the particles of the at least one active metal have a size of about 30 μm to about 50 μm.

Embodiment 20. The anti-pathogen solid composition of any one of Embodiments 1-19, wherein the particles of the at least one active metal have a size of about 40 μm to about 50 μm.

Embodiment 21. The anti-pathogen solid composition of any one of Embodiments 1-20, wherein the particles of the at least one active metal have a size of about 40 μm to about 45 μm.

Embodiment 22. The anti-pathogen solid composition of any one of Embodiments 1-21, further comprising a second metal or metal oxide.

Embodiment 23. The anti-pathogen solid composition of Embodiment 22, wherein the second metal is selected from Ni, Zn, Mn, and Pd, or oxides thereof.

Embodiment 24. The anti-pathogen solid composition of Embodiments 22 or 23, wherein the second metal is selected from Zn or ZnO.

Embodiment 25. The anti-pathogen solid composition of any one of Embodiments 22-24, wherein the anti-pathogen solid composition comprises about 0.1% to about 99% by weight of the second metal.

Embodiment 26. The anti-pathogen solid composition of any one of Embodiments 22-25, wherein the anti-pathogen solid composition comprises about 0.1% to about 75% by weight of the second metal.

Embodiment 27. The anti-pathogen solid composition of any one of Embodiments 22-26, wherein the anti-pathogen solid composition comprises about 0.1% to about 50% by weight of the second metal.

Embodiment 28. The anti-pathogen solid composition of any one of Embodiments 22-27, wherein the anti-pathogen solid composition comprises about 0.1% to about 15% by weight of the second metal.

Embodiment 29. The anti-pathogen solid composition of any one of Embodiments 22-28, wherein the anti-pathogen solid composition comprises about 0.1% to about 5% by weight of the second metal.

Embodiment 30. The anti-pathogen solid composition of any one of Embodiments 22-29, wherein the anti-pathogen solid composition comprises about 0.1% to about 3% by weight of the second metal.

Embodiment 31. The anti-pathogen solid composition of any one of Embodiments 22-30, wherein the anti-pathogen solid composition comprises about 0.1% to about 1% by weight of the second metal.

Embodiment 32. The anti-pathogen solid composition of any one of Embodiments 1-31, further comprising an antioxidant.

Embodiment 33. The anti-pathogen solid composition of Embodiment 32, wherein the antioxidant is pentaerythritol tetrakis[3-[3,5-di-tert-butyl-4-hydroxyphenyl]propionate (Irganox® 1010) and tris(2,4-di-tert.-butylphenyl)phosphite (Irgafos® 168).

Embodiment 34. The anti-pathogen solid composition of any one of Embodiments 1-33, wherein the anti-pathogen solid composition is or comprises a material selected from polymers, plastics, ceramics, rubbers, paints, ointments, glasses, silicones, papers, fabric, metals, and combinations thereof.

Embodiment 35. The anti-pathogen solid composition of Embodiment 34, wherein the anti-pathogen solid composition is or comprises a polymer.

Embodiment 36. The anti-pathogen solid composition of Embodiment 35, wherein the polymer is selected from polypropylenes, polystyrenes, polyethylenes, polyesters, polycarbonates, polyurethanes, polyvinylchlorides, and combinations thereof.

Embodiment 37. The anti-pathogen solid composition of Embodiments 35 or 36, wherein the polymer is a polypropylene.

Embodiment 38. The anti-pathogen solid composition of any one of Embodiments 1-37, wherein the anti-pathogen solid composition is flexibly formed to cover a surface.

Embodiment 39. An anti-pathogen composition comprising:
  about 0.01% to about 5% by weight of an active component, wherein the active component comprises particles of an activated transition metal or transition metal oxide; and
  about 1% to about 99.99% by weight of a polymer.

Embodiment 40. An anti-pathogen suspension comprising particles of an active component and a water or saline solution, wherein the active component comprises particles of at least one activated metal.

Embodiment 41. The anti-pathogen suspension of Embodiment 40, wherein the pH of the suspension is about 5.5 or less.

Embodiment 42. The anti-pathogen suspension of Embodiment 41, wherein the pH of the suspension is about 4.0 or less.

Embodiment 43. The anti-pathogen suspension of Embodiment 42, wherein the pH of the suspension is about 2.0 or less.

Embodiment 44. The anti-pathogen suspension of Embodiment 43, wherein the pH of the suspension is about 1.5 or less.

Embodiment 45. The anti-pathogen suspension of any one of Embodiments 40-44, wherein the weight ratio of the activated metal to the saline solution is from about 1:100 to about 1:1.

Embodiment 46. The anti-pathogen suspension of Embodiment 45, wherein the weight ratio of the activated metal to the saline solution is from about 1:100 to about 1:25.

Embodiment 47. The anti-pathogen suspension of Embodiment 46, wherein the weight ratio of the activated metal to the saline solution is from about 1:100 to about 1:50.

Embodiment 48. The anti-pathogen suspension of Embodiment 47, wherein the weight ratio of the activated metal to the saline solution is from about 1:100 to about 1:75.

Embodiment 49. The anti-pathogen suspension of Embodiment 48, wherein the weight ratio of the activated metal to the saline solution is about 1:100.

Embodiment 50. The anti-pathogen suspension of any one of Embodiments 40-49, wherein the suspension is a lotion, ointment, gel, paste, or a cream.

Embodiment 51. A method for neutralizing pathogens on a surface, the method comprising a step of contacting the surface with the anti-pathogen suspension of any one of Embodiments 40-50.

Embodiment 52. The method of Embodiment 51, wherein the surface is human skin.

Embodiment 53. The method of Embodiments 51 or 52, wherein the pathogens are selected from Gram positive bacteria, Gram negative bacteria, fungi, viruses, and algae.

Embodiment 54. The method of any one of Embodiments 51-53, wherein the pathogens are selected from *micrococcus, staphylococcus, bacillus, pseudomonas, legionella, salmonella, listeria, clostridium perfringens, Acinetobacter baumannii, Escherichia coli*, coronaviruses, rhinoviruses, influenza, norovirus, adenovirus, parainfluenza, respiratory syncytial virus, and enterovirus.

Embodiment 55. A water-permeable pouch comprising an active component, wherein the active component is or comprises particles of an activated metal.

Embodiment 56. The water-permeable pouch of Embodiment 55, further comprising a pH indicator.

Embodiment 57. The anti-pathogen solid composition of Embodiments 1 or 2, wherein the at least one activated metal is selected from Mo, Zn, Cu, Au, Ag, or an oxide thereof.

Embodiment 58. The anti-pathogen solid composition of Embodiment 3, wherein the at least one activated metal is Mo, Mo(IV), Mo(V), or Mo(VI), or an oxide thereof.

Embodiment 59. The anti-pathogen solid composition of Embodiment 3, wherein the at least one activated metal is selected from Mo, $MoO_2$, $MoO_3$, $MoO_5$, $Mo_2O_6$, $H_2MoO_5$, Zn, ZnO, Cu, $Cu_2O$, CuO, Au, AuO, $Au_2O_3$, Ag, and $Ag_2O$.

Embodiment 60. The anti-pathogen solid composition of Embodiment 22, wherein the second metal is selected from Ni, Zn, Mn, Au, Ag, Cu, and Pd, or oxides thereof.

Embodiment 61. The anti-pathogen solid composition of Embodiment 34, wherein the material is a metal (e.g., a stainless steel).

Embodiment 62. The anti-pathogen solid composition of Embodiment 61, wherein the metal is or comprises a stainless steel.

Embodiment 63. An anti-pathogen composition comprising: about 0.01% to about 5% by weight of an active component, wherein the active component comprises particles of an activated transition metal or transition metal oxide; and about 1% to about 99.99% by weight of a stainless steel.

Embodiment 64. The anti-pathogen solid composition of any one of Embodiments 1-14, wherein the particles of the at least one active metal have a size of about 1 μm to about 1000 μm.

Embodiment 65. A method for neutralizing pathogens in a water sample, the method comprising a step of contacting the water sample with the water-permeable pouch of Embodiments 55 or 56 for a period of time sufficient to neutralize the pathogens in the water sample.

Embodiment 66. The method of Embodiment 65, wherein the method further comprises contacted the water sample with ZnO to neutralize the pH.

Embodiment 67. An anti-pathogen liquid composition comprising particles of an active component and a water or saline solution, wherein the active component comprises at least one activated metal.

Embodiment 68. The anti-pathogen liquid composition of Embodiment 67, wherein the pH of the liquid composition is about 5.5 or less.

Embodiment 69. The anti-pathogen liquid composition of Embodiment 68, wherein the pH of the liquid composition is about 4.0 or less.

Embodiment 70. The anti-pathogen liquid composition of Embodiment 69, wherein the pH of the liquid composition is about 2.0 or less.

Embodiment 71. The anti-pathogen liquid composition of Embodiment 70, wherein the pH of the liquid composition is about 1.5 or less.

Embodiment 72. The anti-pathogen liquid composition of any one of Embodiment 67-71, wherein the weight ratio of the activated metal to the water or saline solution is from about 1:100 to about 1:1.

Embodiment 73. The anti-pathogen liquid composition of Embodiment 72, wherein the weight ratio of the activated metal to the water or saline solution is from about 1:100 to about 1:25.

Embodiment 74. The anti-pathogen liquid composition of Embodiment 73, wherein the weight ratio of the activated metal to the water or saline solution is from about 1:100 to about 1:50.

Embodiment 75. The anti-pathogen liquid composition of Embodiment 74, wherein the weight ratio of the activated metal to the water or saline solution is from about 1:100 to about 1:75.

Embodiment 76. The anti-pathogen liquid composition of Embodiment 75, wherein the weight ratio of the activated metal to the water or saline solution is about 1:100.

Embodiment 77. A fabric treated with the anti-pathogen liquid composition of any one of Embodiments 67-76.

EXEMPLIFICATION

The present teachings include descriptions provided in the Examples that are not intended to limit the scope of any claim. Unless specifically presented in the past tense, inclusion in the Examples is not intended to imply that the experiments were actually performed. The following non-limiting examples are provided to further illustrate the present teachings. Those of skill in the art, in light of the present application, will appreciate that many changes can be made in the specific embodiments that are provided herein and still obtain a like or similar result without departing from the spirit and scope of the present teachings.

Example 1—Activation of Metals and Metal Oxides

Metals described in these examples are activated as described in the present application.

Activation by $H_2O_2$ ("Washing")

Mo particles of having a size of about 40 μm to about 45 μm were submerged in an aqueous solution of about 35% $H_2O_2$. Metal particles started with black/gray coloration and changed to yellow coloration after a period of time. The particles were then filtered and vacuum dried before being used in experiments or further incorporated into polymer materials or suspensions, as described below.

A change in structure of the activated Mo particles was visualized on an OMAX 40X-2500X LED Digital Trinocular Microscope. An image of unactivated Mo particles under microscope is seen in FIGS. 1A and 1B. An image of activated Mo particles under microscope is seen in FIGS. 2A, 2B, and 2C. It is observed that Mo particles, after activation, take on an orthorhombic structure.

Activation by Calcination $MoO_3$ particles having a size of 44 μm were heated at 250° C. for two hours. The resulting particles were allowed to cool and then used in experiments directly or further incorporated into polymer materials or suspensions, as described below.

Example 2—Preparation Of Metal Particles in a Polymer

The present example provides a method for preparing a dry blended $MoO_3$ in a polypropylene composition and an antioxidant blend of Irganox 1010 and Irgafos 168 (primary and secondary polypropylene antioxidants).

2.5 wt % of $MoO_3$, activated by calcination, granular polypropylene, and the antioxidant blend of Irganox 1010 and Irgafos 168 are fed through a hopper into a heating barrel. The materials are heated until molten and injected by a large screw through the gate and into the mold. The molten materials are cooled and then sanded (e.g., sandblasted, hand sanded, for example with 120 grit sandpaper, or bead blasted) to remove light films that prevent an activated Mo from contacting a pathogen.

Example 3—Effectiveness of Mo Metal Plate Against *Listeria Monocytogenes* Strain ATCC 23074

The present example was conducted to determine whether the various metal plates exhibited anti-*Listeria monocytogenes* ATCC 23074 activity over the course of 3 hours and whether one composition may be more active than the others. In particular, the present example illustrates that Mo plates exhibit substantially similar if not improved antipathogen activity over Cu plates.

Metal plates were marked with a lab marker with circles in the design of the experimental template to facilitate placement and retrieval of the bacterial populations at the four time points with 3 equivalently spotted samples [10 μL each] harvested at each time point. These time frames were 0 min, 1 hour, 2 hours, and 3 hours.

Sample Processing. Metal plates were surfaced cleaned, then each plate was aseptically transferred into Corning a glass tray having a cover to avoid spread of the pathogen inoculum over the course of the challenge incubation. The inoculum consisted of a 72 hr culture of *Listeria cytogenes* in Trypticase Soybroth medium with an estimated population density of $1.1\text{-}1.2 \times 10^5$ cells/mL as determined by plate count method. A 10 μL droplet would therefore deliver to the metal surface $1.2 \times 10^3$ cells [1200 cells]. One swab was used to harvest 3 equivalent spots or $3.6 \times 10^3$ cells.

Figure 5A:
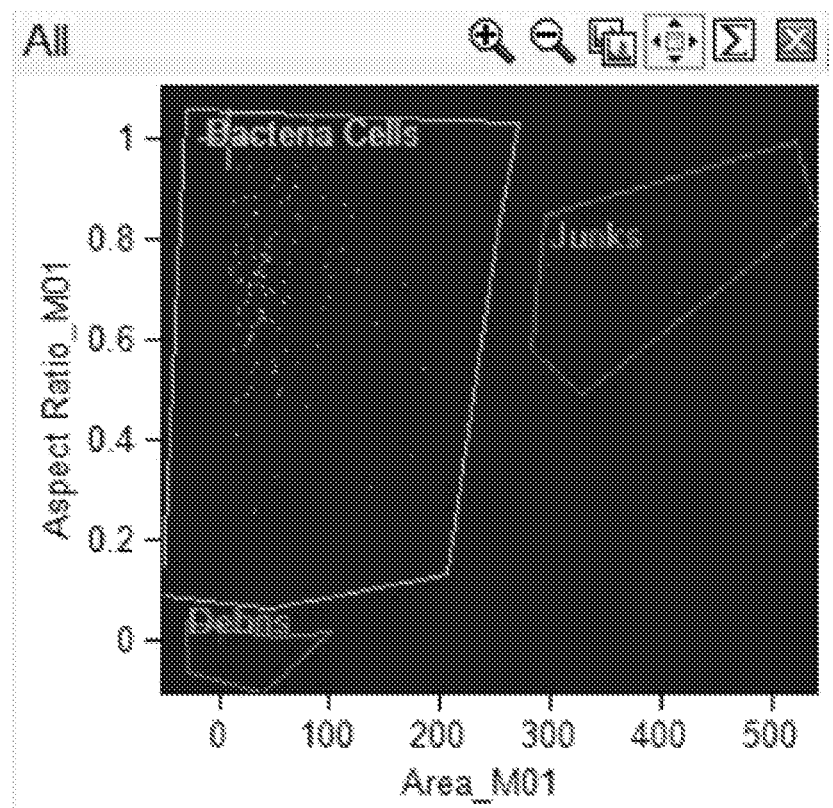
FIG. 5A is a scatter plot illustrating the ratio of bacteria cells to other materials in a copper sample after testing.
Figure 5B:
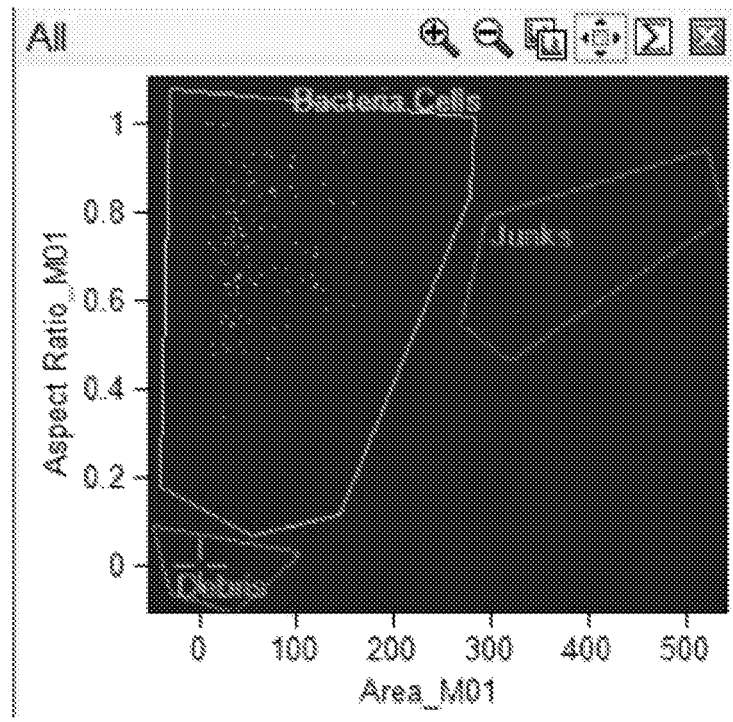
FIG. 5B is a scatter plot illustrating the ratio of bacteria cells to other materials in a molybdenum sample after testing.

Population Determinations were examined by Amnis Imaging Flowcytometer. FIGS. 5A and 5B and the tables below illustrate that the inoculum level was determined to be the mean of these two analyses, [46,146+37,628 /2]=41,887 or $4.189 \times 10^4$ cells/mL.

| Population | Count | % Gated | Objects/mL |
|---|---|---|---|
| All | 1000 | 100 | 82699.44 |
| Bacteria Cells | 558 | 55.8 | 46146.29 |
| Junks | 3 | 0.3 | 248.1 |
| Debris | 439 | 43.9 | 36305.05 |
| All | 1000 | 100 | 72362.01 |
| Bacteria Cells | 520 | 52 | 37628.24 |
| Junks | 3 | 0.3 | 217.09 |
| Debris | 476 | 47.6 | 34444.32 |

Results: Initial Plating of *Listeria monocytogenes* onto the metal plates followed by population determinations using the Tempo Total Viable Count Instrumental method at each time point provided the test results found in appendage files to this report. A simplified summary is presented in the table below:

| Time (hours) | Cu Plate (CFU/mL) | Mo Plate (CFU/mL) |
|---|---|---|
| T = 0 hours | =1200 | >1200 |
| T = 1 hour | =620 | =520 |
| T = 2 hours | <0.25 | <0.25 |
| T = 3 hours | <0.25 | <0.25 |

Conclusions: At relatively low population densities (<2,000 cells), Cu Plate showed significant population reduction of *Listeria monocytogenes* strain ATCC 23074. The Mo Plate also showed significant population reduction.

Example 4—Effectiveness of Metal Particles in a Polypropylene Blend Against Methicillin-Resistant *Staphylococcus aureus* (MRSA)

$MoO_3$ in a polypropylene blend was tested against methicillin-resistant *Staphylococcus aureus* (MRSA). The samples were prepared according to Example 2:

| Sample | Wt % of $MoO_3$ | Additives |
|---|---|---|
| 1 | 0.5% | Irganox 1010 and Irgafos 168 |
| 2 | 1% | Irganox 1010 and Irgafos 168 |
| 3 | 2.5% | Irganox 1010 and Irgafos 168 |

Sample 3 was contacted with MRSA for a period of 12 hours, after which the sample was tested to determine the amount of MRSA remaining on the surface. Testing confirmed that the concentration of MRSA decreased 86.7% after 12 hours as compared to baseline.

Example 5—Effectiveness of Metal Suspension Against MRSA and *Escherichia coli* (*E. coli*)

2.5 g of $MoO_3$ activated by calcination were suspended in a 100 mL saline solution to provide a suspension. MRSA was contacted with the suspension for a period of 3 hours, 6 hours, and 24 hours at 22.3° C., and then recovered for each of duplicate flasks A and B. The results are presented in the table below, illustrating that, within 24 hours, no MRSA was detectable in the suspension.

| | | 3 hours | | | 6 hours | | | 24 hours | | |
|---|---|---|---|---|---|---|---|---|---|---|
| Treatment | Sample | $Log_{10}$ Reduction* | Average $Log_{10}$ Reduction ± SD | Percent Reduction | $Log_{10}$ Reduction* | Average $Log_{10}$ Reduction ± SD | Percent Reduction | $Log_{10}$ Reduction* | Average $Log_{10}$ Reduction ± SD | Percent Reduction |
| Control flasks (PBS) | A | 0.05 | 0.06 ± 0.01 | 12.9 | 0.15 | 0.11 ± 0.06 | 22.4 | 0.33 | 0.41 ± 0.11 | 61.1 |
| | B | 0.06 | | | 0.06 | | | 0.49 | | |
| Test flasks (PBS w/ Additive A) | A | 4.99 | † 4.99 ± 0.00 | 99.9990 | 4.89 | † 5.00 ± 0.16 | 99.9990 | >5.59 | † >5.59 ± 0.00 | >99.9997 |
| | B | 4.99 | | | 5.11 | | | >5.59 | | |

† Reduction was statistically significant (P ≤ 0.05) in comparison to the reductions observed on the control phosphate buffered saline flasks at the same exposure contact time. The value of P is the probability of obtaining results as extreme as observed results of a statistical hypothesis test, assuming that the null hypothesis is correct.

5 g of activated Mo particles, having a size of 40-45 μm were activated by washing and suspended in 100 mL of a saline solution/phosphate buffered saline solution. *E. coli* was then contacted with the suspension for a period of 3 hours, 6 hours, and 24 hours at 21.1° C., and then recovered for each of duplicate flasks A and B. The results are presented in the table below, illustrating that, within 24 hours no *E. coli* was detectable in the suspension.

| Treatment | Sample | 3 hours Log₁₀ Reduction* | 3 hours Average Log₁₀ Reduction ± SD | 3 hours Percent Reduction | 6 hours Log₁₀ Reduction* | 6 hours Average Log₁₀ Reduction ± SD | 6 hours Percent Reduction | 24 hours Log₁₀ Reduction* | 24 hours Average Log₁₀ Reduction ± SD | 24 hours Percent Reduction |
|---|---|---|---|---|---|---|---|---|---|---|
| Control flasks (PBS) | A | 0.07 | 0.04 ± 0.05 | 8.8 | 0.02 | 0.04 ± 0.02 | 8.8 | 0.10 | 0.05 ± 0.07 | 10.9 |
|  | B | 0.00 |  |  | 0.05 |  |  | 0.00 |  |  |
| Test flasks (PBS w/ 10% Mo) | A | >4.80 | † >4.80 ± 0.00 | >99.998 | >4.80 | † >4.80 ± 0.00 | >99.998 | >4.80 | † >4.80 ± 0.00 | >99.998 |
|  | B | >4.80 |  |  | >4.80 |  |  | >4.80 |  |  |

† Reduction was statistically significant ($P \leq 0.05$) in comparison to the reductions observed on the control phosphate buffered saline flasks at the same exposure contact time.

Example 6—Effectiveness of Metal Particles in a Polypropylene Blend Against SARS-CoV-2 and Coronavirus-229E Mo (5% by weight) in a polypropylene blend will be tested against SARS-CoV-2 and Coronavirus-229E. The sample will be prepared according to Example 2. The sample will be contacted with SARS-CoV-2 and Coronavirus-229E for a period of 6 hours at ambient conditions, where the sample will be tested to determine the amount of SARS-CoV-2 and Coronavirus-229E remaining on the surface at each of 1 hour, 3 hours, and 6 hours.

Example 7—Effectiveness of Metal Suspension Against SARS-CoV-2 and Coronavirus 229E A saline solution comprising SARS-CoV-2 or Coronavirus 229E is prepared according to standard methods (Spray 1A and Spray 1B, respectively)). A suspension comprising Mo particles (40-45 μm particle size) activated by washing in saline and SARS-CoV-2 or Coronavirus 229E are prepared (Spray 2A and Spray 2B, respectively).

A polypropylene surface and a surface prepared as described in Example 6 will each be sprayed with each of Sprays 1A-2B. Each surface will be tested to determine the amount of SARS-CoV-2 and Coronavirus-229E remaining on each surface at each of 1 hour, 3 hours, and 6 hours.

Example 8—Stability of Activated Metal Suspensions

Samples of activated Mo and $MoO_3$ in in suspension as well as incorporated into polymer solid compositions were found to be shelf stable for at least six months. The following samples were stored at room temperature under ambient conditions, and exhibited consistent pH range after six months.

| Sample | Metal | Concentration/Ratio | pH |
|---|---|---|---|
| 1 | Activated $MoO_3$ | 2.5 g metal/100 mL saline | 2.2 |
| 2 | Activated Mo | 1 g metal/100 mL saline | 1.95 |
| 3 | Activated Mo | 5 g metal/100 mL saline | 1.4 |
| 4 | Unactivated Mo | 1 g metal/100 mL saline | 4 |

A dry mixture of having a 1:1 ratio by weight of activated Mo to ZnO was stored for six months at room temperature under ambient conditions. After six months, no signs of degradation due to color change were observed.

Example 9—Anti Pathogenic Properties by Proximal Contact

Example 9a

Organic, untreated oranges were placed on the test surfaces (Test Surface 1 and Test Surface 2). Test Surface 1 and Test Surface 2 were kept at least four feet apart to prevent cross-contamination.

Test Surface 1=stainless steel without any additives
Test Surface 2=stainless steel wrapped around molybdenum core, wherein molybdenum core was activated via calcination.

Figure 6A:
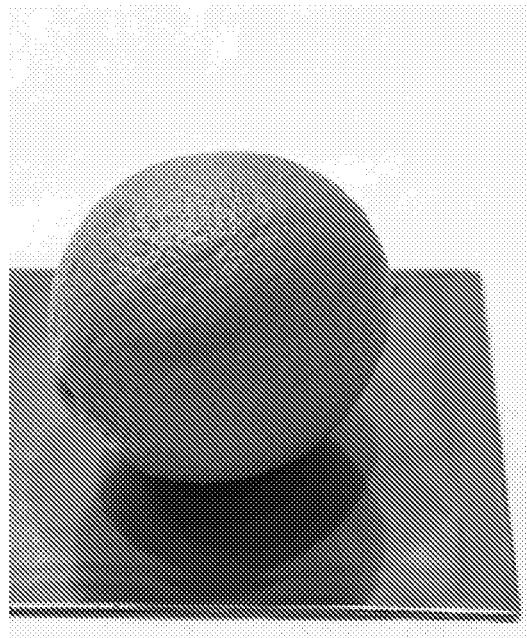
FIGS. 6A-6H are photographs of orange decay over time.
Figure 6B:
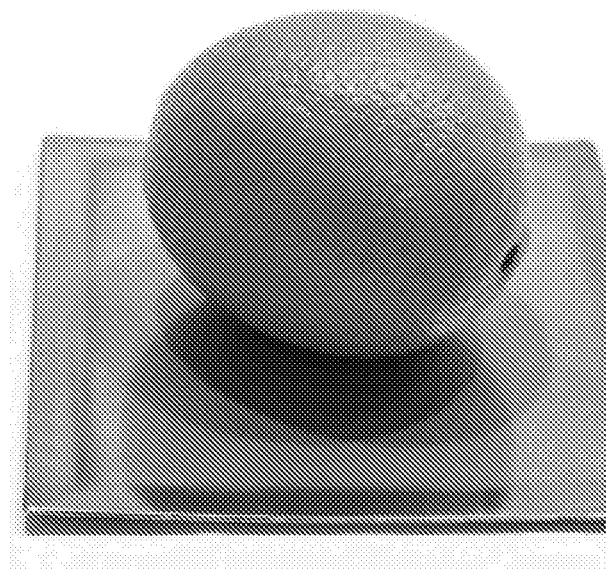
Figure 6C:
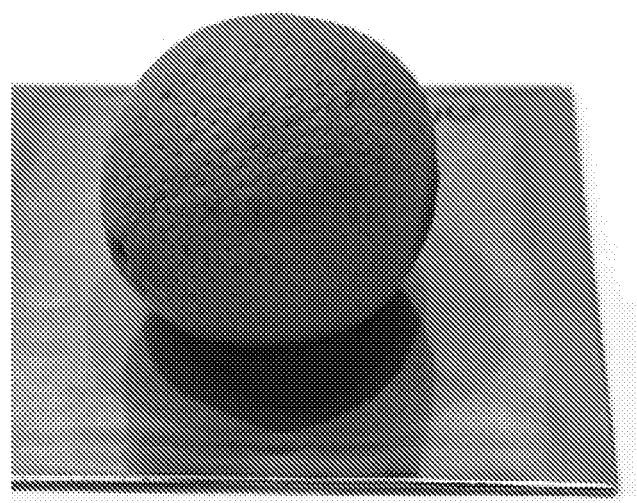
Figure 6D:
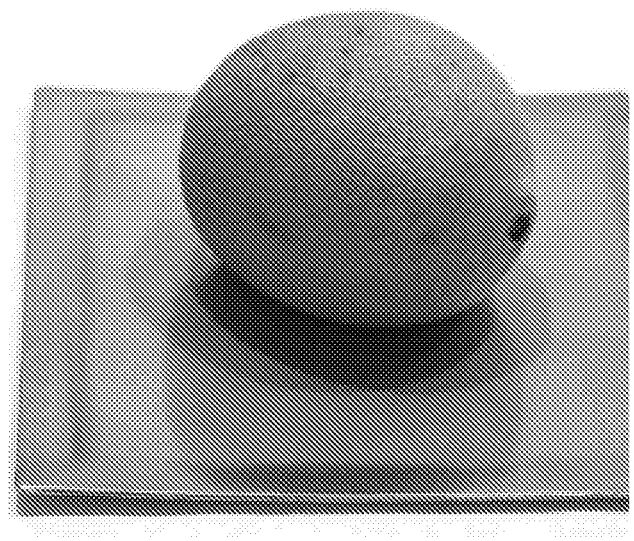
Figure 6E:
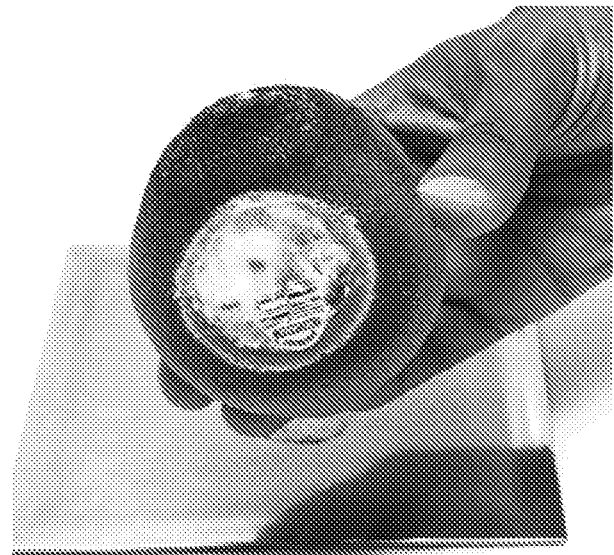
Figure 6F:
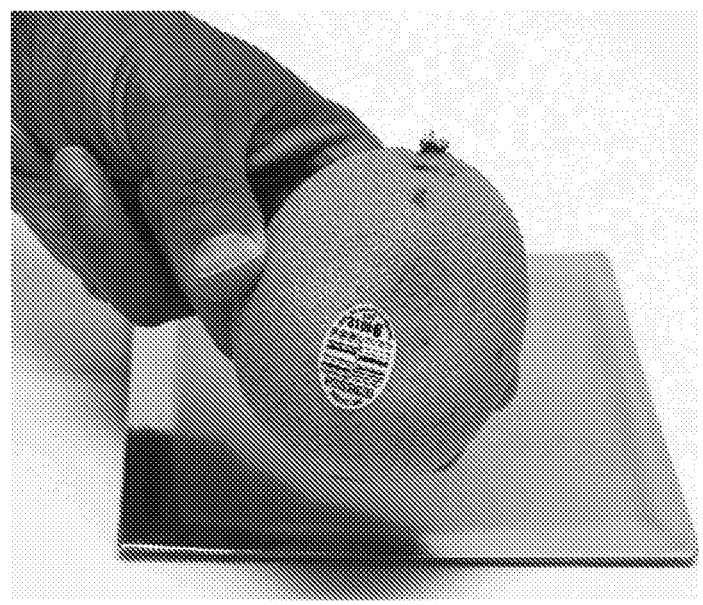
Figure 6G:
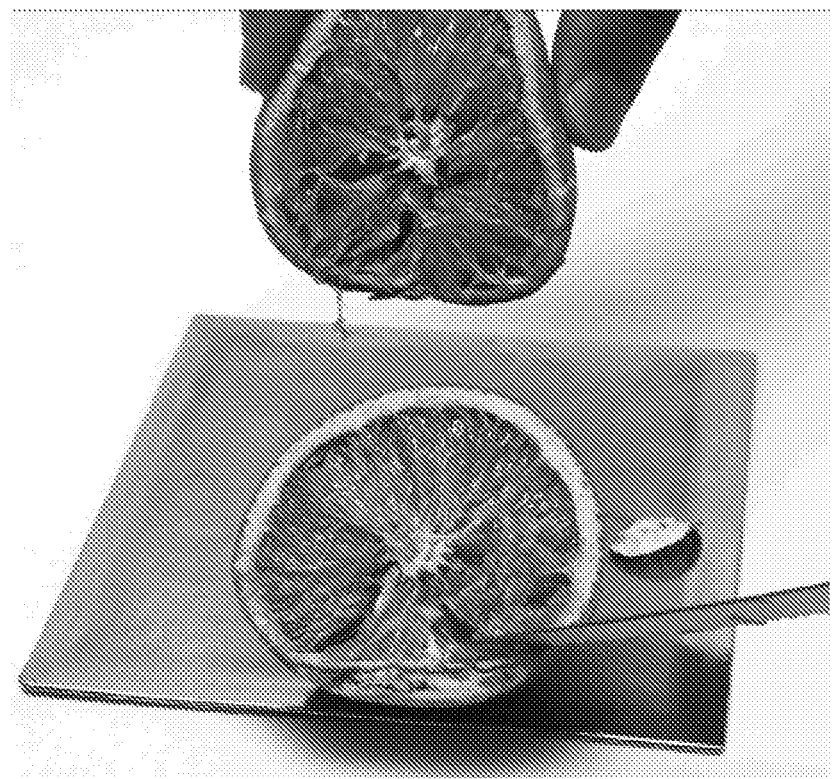
Figure 6H:
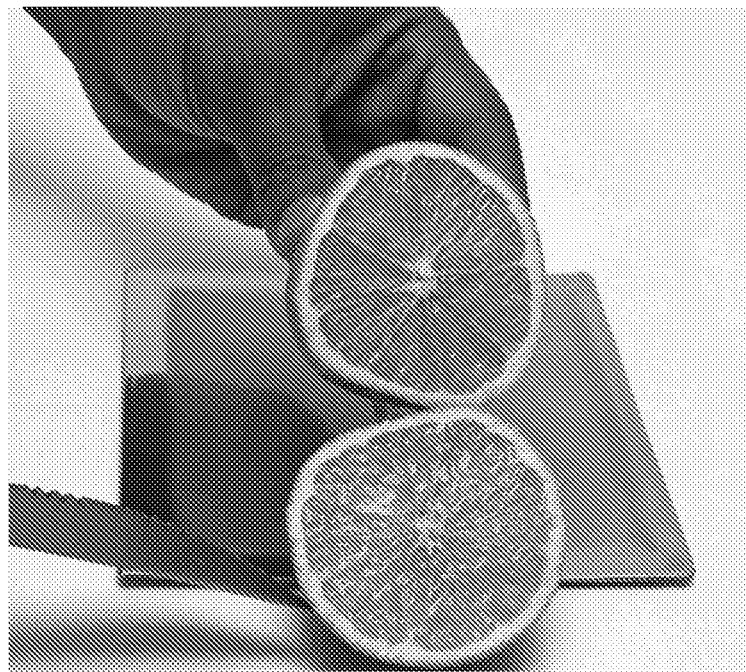

The conditions for the orange storage was room temperature under ambient conditions. Photographs at regular intervals (one for each month) were taken of each orange over the course of fourth months. The results are depicted in FIG. 6A (Test Surface 1, time=0); FIG. 6B (Test Surface 2, time=0 month); FIG. 6C (Test Surface 1, time=4 months); FIG. 6D (Test Surface 2, time=4 months); FIG. 6E (Test Surface 1, time=4 months); FIG. 6F (Test Surface 2, time=4 months); FIG. 6G (Test Surface 1, time=4 months); FIG. 6H (Test Surface 2, time=4 months).

The photographs illustrate that the orange stored on Test Surface 2 exhibited significantly less decay than the orange stored on Test Surface 1. For example, at 4 month, the orange in contact with Test Surface 1 exhibited significant decay and microbe growth (see FIG. 6E for microbe growth and FIG. 6G for internal decay). The orange in contact with Test Surface 2 exhibited significantly less, if not being substantially devoid of, decay and microbe growth (see FIG. 6F as compared to FIG. 6E to illustrate lack of microbe growth and decay, and FIG. 6H to illustrate lack of internal decay as compared to FIG. 6G).

In some embodiments, example embodiments comprising activated molybdenum can increase shelf life of certain food products, e.g., oranges, by at least two months.

Example 9b

Example 9b illustrates that compositions comprising Mo can neutralize pathogens even when not in direct contact. In particular, the present example was conducted to determine whether the various metal plates exhibited anti-*Salmonella typhimurium* ATCC 23555 activity over the course of 3 hours and examination of sample 1 in a "distance test."

Figure 3:
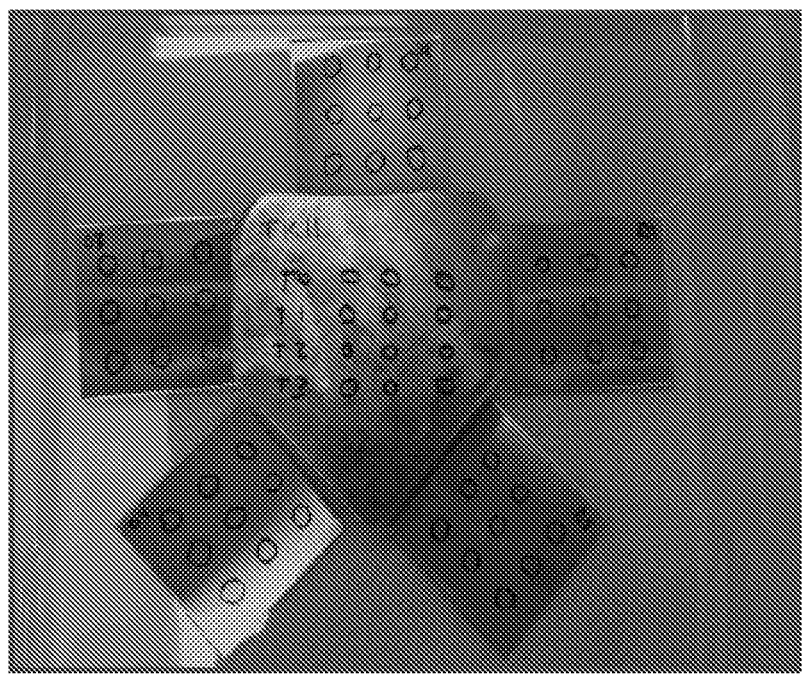
FIG. 3 is a photograph of sample stainless steel coupons comprising Mo just prior to spotting with culture inoculum.

As illustrated in FIG. 3, an image of Sample 1 and 5 stainless steel coupons comprising Mo just prior to spotting with culture inoculum and swab harvest of time point t=0 min. The metal plates were marked with a lab marker with circles in the design of the experimental template to facilitate placement and retrieval of the bacterial populations at the four time points with 3 equivalently spotted samples [10

μL each] harvested at each time point. These time frames were 0 min, 1 hour, 2 hours, and 3 hours. For the distance test a 5$^{th}$ time point was made at t=4 hours from the 5th stainless steel coupon.

Sample Processing

Metal plates were surfaced cleaned, then each plate was aseptically transferred into Corning a glass tray having a cover to avoid spread of the pathogen inoculum over the course of the challenge incubation. The inoculum consisted of a 24 hr culture of *Salmonella typhimurium* ATCC 23555 in Trypticase Soybroth medium with an estimated population density of 2.0×10$^6$ cells/mL as determined by plate count method. A 10 μL droplet delivers to the metal surface approximately 2×10$^4$ cells [20,000 cells]. One swab was used to harvest 3 equivalent spots or theoretically 6×10$^4$ cells if 100% recovery were possible. For the distance test, one stainless steel coupon with spots at a distance of 2.0 cm, 4.0 cm, and 6.0 cm was harvested at each time point.

Figure 4:
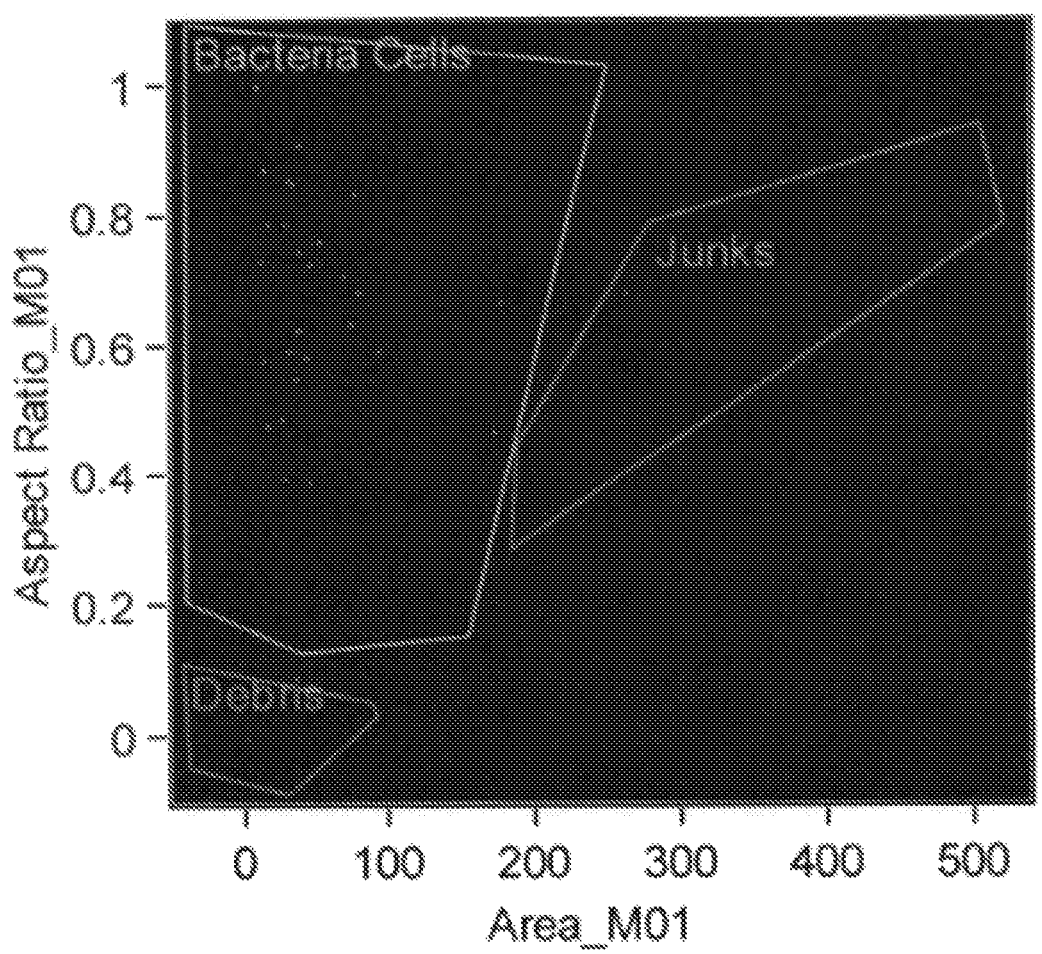
FIG. 4 is a scatter plot illustrating the ratio of bacteria cells to other materials in samples after testing.

Population Determinations:

The initial inoculum was determined using the Amnis Imaging Flowcytometer. FIG. 4 represents this direct determination on the sample and the data in the following table:

| Area_M01, Aspect Ratio_M01 | | | |
|---|---|---|---|
| Population | Count | % Gated | Objects/mL |
| All | 502 | 100 | 27553.08 |
| Bacteria Cells | 241 | 48 | 13227.67 |
| Junks | 1 | 0.2 | 54.89 |
| Debris | 260 | 51.8 | 14270.52 |

By this direct determination method, the inoculum level was determined to be 13,228 cells/mL or 1.32×10$^4$ cells/mL.

Results: Initial Plating of Salmonella typhimurium onto the metal plates followed by population determinations using the Tempo Total Viable Count Instrumental method at each time point provided the test results found in appendage files to this report. A summary is below:

| Simplified Table—Summary Counts Most Probable Number (MPN, expressed at CFU/mL) | | | |
|---|---|---|---|
| Time (Hrs) | Sample 1 TK11 | Sample 2 T11 | Sample 3 T012 |
| T = 0 | =370 | =200 | =740 |
| T = 1 | =230 | =5.7 | =440 |
| T = 2 | =0.82 | <0.25 | =0.26 |
| T = 3 | =0.26 | <0.25 | <0.25 |

Distance Test on Sample 1 [each 316 Stainless Steel Coupon was equal distant from the edge of Sample 1, not in contact with it] from the edge of Sample 1 to the center of each droplet was approximately either 2.0, 4.0 or 6.0 cm.

| Simplified Table—Summary Counts Conts Most Probable Number (MPN, expressed at CFU/mL) | | | | |
|---|---|---|---|---|
| Time (Hrs) | Sample 1 TK11 | Sample 2 T11 | Sample 3 T012 | |
| T = 0 | =370 | =180 | =230 | =230 |
| T = 1 | =230 | =94 | =170 | =200 |
| T = 2 | =0.82 | <0.25 | =0.26 | =0.26 |
| T = 3 | =0.26 | =0.82 | <0.25 | <0.25 |

| Simplified Table—Summary Counts Conts Most Probable Number (MPN, expressed at CFU/mL) | | | | |
|---|---|---|---|---|
| Time (Hrs) | Sample 1 TK11 | Sample 2 T11 | Sample 3 T012 | |
| T = 4 | Not Available | <0.25 | =11 | =0.26 |

Conclusion: At relatively low population densities (<2, 000 cells), sample (no. 2), showed significant population reduction of Salmonella typhimurium strain ATCC 23555. These tests were conducted at a constant 27° C. with no humidification to prevent drying. 3 trays were used, having two trays containing one metal plate each; namely, the first contained sample 2 and the second contained sample 3. Sample 1 was placed into a 14 inch×14 inch plastic box with lid with 316 stainless steel coupons with 5 plates, one on each of its 5 sides. At 1 hour significant populations reductions were obtained with the reduction tapering off with distance but still observable at 6.0 cm from the edge of the large sample 1 metal plate.

Example 10—Additional Exemplary Embodiments

Example 10a

Mo particles (40-45 μm particle size) activated by washing are incorporated into a polypropylene (PP) blend, where the Mo particles are 2.5% by weight of the solid composition. The Mo/PP solid is sanded with 120 grit sand paper and will be contacted with MRSA and *E. coli* for 12 hours. The samples will be tested for the amount of microbe that remains on the sample.

Example 10b

Unactivated Mo particles (40-45 μm particle size) are incorporated into a polypropylene (PP) blend, where the Mo particles are 2.5% by weight of the solid composition. The Mo/PP solid is sanded with 120 grit sand paper, and then subjected to washing conditions. The Mo/PP solid will then be contacted with MRSA and *E. coli* for 12 hours. The samples will be tested for the amount of microbe that remains on the sample.

Example 10c

Mo particles (40-45 μm particle size) activated by washing will be placed into a suspension of saline, such that the ratio of Mo particles to saline solution is between 1:100 and 1:50. *Legionella* will be contacted with the suspension and the amount of bacteria still present in the suspension will be measured at 3 hours, 6 hours, and 24 hours at room temperature (about 25° C.).

Example 11—Stainless Steel Compositions

The present example provides a method for preparing a stainless steel, for example, steps in the manufacturing process of a stainless steel product comprising: 1) melting raw materials that constitute a stainless steel in a furnace for a period of about 8 to about 12 hours, followed by casting a molten steel into a semi-finished form (e.g., slabs, rods, tubes, or other suitable shapes); 2) forming (e.g. hot rolling)

a steel from a semi-finished form into desired form(s) (e.g., plates, strips, sheets, rolls, bars, and/or wires,) shape(s) (e.g., round, square, octagon, hexagon, and/or other shapes,) and/or size(s); 3) heating and/or cooling a steel in controlled environment(s) (e.g., annealing, quenching, and/or other heat treatment) to relieve internal stresses, soften metal(s), and control the strength and toughness of a steel; 4) descaling (e.g. pickling and/or electrocleaning) a steel to remove scales on the surface of a steel; 5) cutting a steel into desired shape(s) using flame cutting and/or mechanical cutting tools (e.g., guillotine knives, circular knives, blanking, nibbling, and/or high speed blades); and 6) surface finishing a steel for a steel to have desired appearance, such as a smooth surface. Furthermore, additional steps and/or quality control may be used or required during manufacturing and fabrication by end user.

Example 12—Stainless Steel Comprising Activated Molybdenum

The present example provides a method for preparing a stainless steel composition comprising activated Mo. Activated Mo is introduced at step of casting or forming (e.g., step 1 or 2 of Example 11). Additionally or alternatively, unactivated Mo is introduced to the stainless steel composition at step of casting or forming (e.g., step 1 or 2 of Example 11). In some embodiments, Mo is activated post-production by at least one of calcination, washing, UV light, and charging methods described herein. In some embodiments, a stainless steel composition is finished via surface preparation (e.g., sanding, polishing, chemical scrubbing, and/or other processes) to enhance surface exposure of Mo.

Example 13—Effectiveness of Stainless Steel Comprising Activated Molybdenum in Saline Against *Acinetobacter baumannii*

A sample of activated Mo (2% by weight) in saline was prepared according to the procedure of Example 5. Acinetobacter baumannii was contacted with the suspension for a period of 3 hours, 6 hours, and 24 hours at 22.3° C. The population of *Acinetobacter baumannii* was reduced in the sample by 99.997% at each time point of 3 hours, 6 hours, and 24 hours.

Example 14—Surface Time-Kill Test of Molybdenum Coupons and Treated Polypropylene Coupons Containing 5% Molybdenum against Human Coronavirus Strain 229E Example 14a—Molybdenum Coupons Materials 1"×1" pure activated molybdenum (>99%) coupons were inoculated with 0.05 ml of human coronavirus strain 229E virus stock solution containing approximately $3.0 \times 10^6$ Median Tissue Culture Infectious Dose $(TCID)_{50}$/ml of human coronavirus strain 229E. The inoculum was spread over the surface of the coupon using a sterile pipet tip. Duplicate coupons were included for each exposure contact time. Duplicate stainless steel coupons were included as controls for each exposure contact time.

Methods

The coupons were placed in sealed Tupperware chambers with moist paper towels and incubated at room temperature (21.6° C.) to prevent drying.

Duplicate samples from the control coupons were collected immediately upon inoculation to determine the baseline viral concentration recovered at t=0 hours. The coupons were sampled with polystyrene swabs to recover the virus particles and the swabs placed into separate 1-ml volumes of Dey-Engley (D/E) neutralizing broth. The samples were vortexed for 30 seconds and then the swabs were removed and discarded. Following this, the sample was diluted 1:2 in cell culture minimal essential medium (MEM) and then the samples were passed through separate syringe filters (0.45 m pore size; pre-wetted with 3% beef extract to prevent virus adsorption to the filters) to remove any contaminants such as bacteria or fungi. This step was necessary since the experiment was not conducted in a sterile environment.

All other control and test coupons were held at room temperature for the remainder of the experiment (21.6° C. at a relative humidity of ~95%). At t=1 and 3 hours, duplicate samples of the remaining control and test coupons were sampled and treated in the manner described previously.

The samples were frozen and stored at −70° C. prior to assay via cell culture.

Virus concentrations for each neutralized sample were quantified using the Reed-Muench method to determine the tissue culture infectious dose that affected 50% of the wells $(TCID_{50})$. The samples were 10-fold serially diluted in MEM. The assay was performed in 96-well cell culture plates containing monolayers of MRC-5 cells (fetal human lung fibroblast). Prior to the assay, the MRC-5 cells were gently rinsed twice with MEM and then the 96-well plates were inoculated with the diluted samples (6 wells inoculated with 50 microliters each per dilution) and the plates were incubated in an atmosphere of 5% $CO_2$ for 1 hour at 35° C. to allow the virus particles to adsorb to the cells.

Each 96-well plate also included at least 6 negative control wells containing cells only (i.e., no antimicrobials or virus) with 50 microliters of MEM added.

Following this incubation period, 150 microliters of MEM containing 2% fetal bovine serum was added to each of the 96 wells and the plates were incubated in an atmosphere of 5% $CO_2$ for 6 days at 35° C.

The cells were observed daily for viral cytopathic effects (CPE) using an inverted microscope. The inoculated cells were compared to the negative control cells in the same 96-well plate to differentiate CPE from un-inoculated cells. Any CPE that was observed within 24 hours of incubation was considered to be caused by cytotoxicity (caused by sensitivity of the cells to the D/E neutralizing buffer or the molybdenum) since CPE caused by coronavirus typically requires 3 days. Wells positive for CPE following 3 days were considered positive for viral growth.

No CPE was observed in any of the negative control wells.

After the incubation period, the $TCID_{50}$/coupon was determined. Six wells per dilution were used to ensure adequate precision of the assay. The greatest dilution in which 50% or higher of the wells were positive was used to determine the virus $TCID_{50}$/coupon following the method described by Payment and Trudel. See Payment P, Trudel M. (1993) Isolation and identification of viruses. In Methods and Techniques in Virology. Payment P, Trudel M (eds.), pp. 32-33. New York: Marcel Dekker Inc.

The data were reported as the logarithmic reduction using the formula $-\log_{10}(N_t/N_0)$, where $N_0$ is the concentration of the recovered coronavirus at time=0 hours and $N_t$ is the concentration of the surviving coronavirus in the sample collected at time=t (i.e., 1 or 3 hours). The percent reduction was also calculated.

A Student's t-test was used to statistically compare the reductions observed on the test coupons with the reductions observed on the control coupons. The reductions were considered to be statistically significant if the resultant P value was <0.05.

Results

Inoculum=$3.0\times10^6$ TCID$_{50}$/coupon
Number of viable virus particles recovered per coupon:
Control Stainless Steel A (0 hours)=$1.6\times10^5$ TCID$_{50}$
Control Stainless Steel B (0 hours)=$7.1\times10^4$ TCID$_{50}$
Control Stainless Steel A (1 hour)=$1.0\times10^5$ TCID$_{50}$
Control Stainless Steel B (1 hour)=$7.1\times10^4$ TCID$_{50}$
Control Stainless Steel A (3 hours)=$8.6\times10^4$ TCID$_{50}$
Control Stainless Steel B (3 hours)=$1.6'10^5$ TCID$_{50}$
T012-Treated Molybdenum A (1 hour)=<$1.6\times10^3$ TCID$_{50}$
T012-Treated Molybdenum B (1 hour)=<$1.6\times10^3$ TCID$_{50}$
T012-Treated Molybdenum A (3 hours)=<$1.6\times10^3$ TCID$_{50}$
T012-Treated Molybdenum B (3 hours)=<$1.6\times10^3$ TCID$_{50}$ Geometric mean number of viable human coronavirus 229E recovered from control stainless steel coupons after one hour=$8.4'10^4$ TCID$_{50}$/coupon.

Geometric mean number of viable human coronavirus 229E recovered from control stainless steel coupons after three hours=$1.2\times10^5$ TCID$_{50}$/coupon.

Geometric mean number of viable human coronavirus 229E recovered from test molybdenum coupons after one hour=<$1.6\times10^3$ TCID$_{50}$/coupon.

Geometric mean number of viable human coronavirus 229E recovered from test molybdenum coupons after three hours=<$1.6\times10^3$ TCID$_{50}$/coupon.

Percent reduction on T012-treated molybdenum coupons after one hour=>98.7%. Percent reduction on T012-treated molybdenum coupons after three hours=>98.7%.

| Organism | Sample | Log$_{10}$ removal* | |
|---|---|---|---|
| | | 1 hour | 3 hours |
| Stainless Steel Control Coupons | Sample 1 | 0.08 | 0.14 |
| | Sample 2 | 0.23 | 0.00 |
| | Average (± SD) | 0.15 ± 0.11 | 0.07 ± 0.10 |
| T012-Treated Molybdenum Coupons | Sample 1 | >1.88 | >1.88 |
| | Sample 2 | >1.88 | >1.88 |
| | Average (± SD) | >1.88 ± 0.00 | >1.88 ± 0.00 |

*Initial concentration of human coronavirus 229E was approximately $3.0 \times 10^6$ TCID$_{50}$/coupon; however, an average of only $1.2 \times 10^5$ TCID$_{50}$ was recovered from the control coupons at t = 0 hours. This value was used to calculate the log10 reductions for the subsequent samples collected.
SD Standard deviation.
>The number of virus particles recovered was below the detection limit of the assay. Toxicity was observed in the cell culture assay in the wells with lower dilutions of the samples. This increased the detection limit of the assay from $1.6 \times 10^2$ TCID$_{50}$/ml to $1.6 \times 10^3$ TCID$_{50}$/ml.

Discussion

A loss of approximately 1.4 log$_{10}$ was observed between the number of virus particles inoculated onto the coupons and the number of particles recovered from the control samples at t=0 hours. Without being bound by theory, it is believed that this is due to three factors: 1) the recovery efficiency of the virus using the swab method, 2) the loss of virus particles during the filtration step, and 3) the loss of virus particles due to freezing/thawing of the samples. In addition, cytotoxicity was observed in the cell culture assay in the wells inoculated with the lowest dilution (i.e., $1\times10^1$, the highest concentration) of the neutralized filtered samples. This effectively increased the detection limit of the assay by 1 log$_{10}$ since the lowest dilution that could be quantified was $1\times10^{-2}$.

T012-treated molybdenum coupons were effective at reducing the numbers of viable human coronavirus 229E particles (>1.88 log$_{10}$) within one hour of contact time. The reductions observed on all molybdenum surfaces was statistically significant (P≤0.05) in relationship to the reductions observed on the control stainless steel coupons (average of 0.11 log$_{10}$).

Example 14b—Polypropylene Coupons Containing 5% Molybdenum

Materials

The experiment was conducted on 1"×2" treated polypropylene coupons containing 5% activated molybdenum (>99% pure; 45 μm particle size) and 2"×2" control polypropylene coupons. The coupons were inoculated with 0.05 ml of virus stock solution containing approximately $3.0\times10^6$ TCID$_{50}$/ml of human coronavirus strain 229E. The inoculum was spread over the central 1"×1" surface of the coupon using a sterile pipet tip. Duplicate coupons were included for each exposure contact time for both the test polypropylene coupons (containing molybdenum) and the polypropylene control coupons.

Methods

The coupons were placed in sealed Tupperware chambers with moist paper towels and incubated at room temperature (21.6° C.) to prevent drying.

Duplicate samples from the control coupons were collected immediately upon inoculation to determine the baseline viral concentration recovered at t=0 hours. The coupons were sampled with polystyrene swabs to recover the virus particles and the swabs placed into separate 1-ml volumes of Dey-Engley (D/E) neutralizing broth. The samples were vortexed for 30 seconds and then the swabs were removed and discarded. Following this, the sample was diluted 1:2 in cell culture minimal essential medium (MEM) and then the samples were passed through separate syringe filters (0.45 m pore size; pre-wetted with 3% beef extract to prevent virus adsorption to the filters) to remove any contaminants such as bacteria or fungi. This step was necessary since the experiment was not conducted in a sterile environment.

All other control and test coupons were held at room temperature for the remainder of the experiment (21.6° C. at a relative humidity of ~95%). At t=1 and 3 hours, duplicate samples of the remaining control and test coupons were sampled and treated in the manner described previously.

The samples were frozen and stored at −70° C. prior to assay via cell culture.

Virus concentrations for each neutralized sample were quantified using the Reed-Muench method to determine the tissue culture infectious dose that affected 50% of the wells (TCID$_{50}$). The samples were 10-fold serially diluted in MEM. The assay was performed in 96-well cell culture plates containing monolayers of MRC-5 cells (fetal human lung fibroblast). Prior to the assay, the MRC-5 cells were gently rinsed twice with MEM and then the 96-well plates were inoculated with the diluted samples (6 wells inoculated with 50 microliters each per dilution) and the plates were incubated in an atmosphere of 5% CO$_2$ for 1 hour at 35° C. to allow the virus particles to adsorb to the cells.

Each 96-well plate also included at least 6 negative control wells containing cells only (i.e., no antimicrobials or virus) with 50 microliters of MEM added.

Following this incubation period, 150 microliters of MEM containing 2% fetal bovine serum was added to each of the 96 wells and the plates were incubated in an atmosphere of 5% $CO_2$ for 6 days at 35° C.

The cells were observed daily for viral cytopathic effects (CPE) using an inverted microscope. The inoculated cells were compared to the negative control cells in the same 96-well plate to differentiate CPE from un-inoculated cells. Any CPE that was observed within 24 hours of incubation was considered to be caused by cytotoxicity (caused by sensitivity of the cells to the D/E neutralizing buffer or the molybdenum) since CPE caused by coronavirus typically requires 3 days. Wells positive for CPE following 3 days were considered positive for viral growth.

No CPE was observed in any of the negative control wells.

After the incubation period, the $TCID_{50}$/coupon was determined. Six wells per dilution were used to ensure adequate precision of the assay. The greatest dilution in which 50% or higher of the wells were positive was used to determine the virus $TCID_{50}$/coupon following the method described by Payment and Trudel. See Payment P, Trudel M. (1993) Isolation and identification of viruses. In Methods and Techniques in Virology. Payment P, Trudel M (eds.), pp. 32-33. New York: Marcel Dekker Inc.

The data were reported as the logarithmic reduction using the formula $-\log_{10}(N_t/N_0)$, where $N_0$ is the concentration of the recovered coronavirus at time=0 hours and $N_t$ is the concentration of the surviving coronavirus in the sample collected at time=t (i.e., 1 or 3 hours). The percent reduction was also calculated.

A Student's t-test was used to statistically compare the reductions observed on the test coupons with the reductions observed on the control coupons. The reductions were considered to be statistically significant if the resultant P value was <0.05.

Results

Inoculum=$3.0\times10^6$ $TCID_{50}$/coupon

Number of viable virus particles recovered per coupon:

Control Polypropylene A (0 hours)=$8.6\times10^4$ $TCID_{50}$

Control Polypropylene B (0 hours)=$4.0\times10^4$ $TCID_{50}$

Control Polypropylene A (1 hour)=$8.6\times10^4$ $TCID_{50}$

Control Polypropylene B (1 hour)=$4.0\times10^4$ $TCID_{50}$

Control Polypropylene A (3 hours)=$4.0\times10^4$ $TCID_{50}$

Control Polypropylene B (3 hours)=$8.6\times10^4$ $TCID_{50}$

Treated Polypropylene Containing Molybdenum A (1 hour)=$8.6\times10^3$ $TCID_{50}$ Treated Polypropylene Containing Molybdenum B (1 hour)=$7.1\times10^3$ $TCID_{50}$ Treated Polypropylene Containing Molybdenum A (3 hours)=$8.6\times10^3$ $TCID_{50}$ Treated Polypropylene Containing Molybdenum B (3 hours)=$4.0\times10^3$ $TCID_{50}$ Geometric mean number of viable human coronavirus 229E recovered from control polypropylene coupons after one hour=$5.9\times10^4$ $TCID_{50}$/coupon.

Geometric mean number of viable human coronavirus 229E recovered from control polypropylene coupons after three hours=$5.9\times10^4$ $TCID_{50}$/coupon.

Geometric mean number of viable human coronavirus 229E recovered from treated polypropylene coupons containing molybdenum after one hour=$7.9\times10^3$ $TCID_{50}$/coupon.

Geometric mean number of viable human coronavirus 229E recovered from treated polypropylene coupons containing molybdenum after three hours=$5.9\times10^3$ $TCID_{50}$/coupon.

Percent reduction on treated polypropylene coupons containing molybdenum after one hour=87.7%.

Percent reduction on treated polypropylene coupons containing molybdenum after three hours=90.7%.

| | | $Log_{10}$ removal* | |
|---|---|---|---|
| Organism | Sample | 1 hour | 3 hours |
| Polypropylene | Sample 1 | 0.00 | 0.20 |
| Control | Sample 2 | 0.20 | 0.00 |
| Coupons | Average (± SD) | 0.10 ± 0.14 | 0.10 ± 0.14 |
| Treated | Sample 1 | 0.87 | 0.87 |
| Polypropylene | Sample 2 | 0.95 | 1.20 |
| Test Coupons | Average (± SD) | 0.91 ± 0.06 | 1.03 ± 0.24 |

*Initial concentration of human coronavirus 229E was approximately $3.0\times10^6$ $TCID_{50}$/coupon; however, an average of only $6.3\times10^4$ $TCID_{50}$ was recovered from the control coupons at t = 0 hours. This value was used to calculate the logio reductions for the subsequent samples collected.
SD Standard deviation.

Number of viable virus particles recovered per coupon ($\log_{10}$ reductions) and antimicrobial efficacy is summarized below. Experiment was conducted with duplicate samples at 21.6° C. at a relative humidity of ~95% (t=0 hours collected immediately following inoculation).

Discussion

A loss of approximately 1.68 $\log_{10}$ was observed between the number of virus particles inoculated onto the coupons and the number of particles recovered from the control samples at t=0 hours. This is likely due to three factors: 1) the recovery efficiency of the virus using the swab method, 2) the loss of virus particles during the filtration step, and 3) the loss of virus particles due to freezing/thawing of the samples. In addition, cytotoxicity was observed in the cell culture assay in the wells inoculated with the lowest dilution (i.e., $1\times10^{-1}$, the highest concentration) of the neutralized filtered samples.

The treated polypropylene coupons containing 5% molybdenum were effective at reducing the numbers of viable human coronavirus 229E particles within one and three hours of contact time (0.91 and 1.03 $\log_{10}$, respectively). The reductions observed on all treated polypropylene surfaces was statistically significant (P≤0.05) in relation to the reductions observed on the control polypropylene coupons (average of 0.10 $\log_{10}$).

Example 15—Surface Time-Kill Test of Stainless Steel Coupons Sprayed with Saline Solution Treated with Molybdenum Against MS-2 Bacteriophage (Virus) and Human Coronavirus Strain 229E Example 15a—MS-2 Bacteriophage (Virus)

MS-2 is a non-enveloped RNA virus and used as a surrogate for a large range of human enteric pathogenic viruses (e.g., enteroviruses, noroviruses, rotaviruses, and hepatitis A and E viruses).

Materials

Prior to experimentation, 25 g of activated molybdenum powder (>99% pure; 45 μm particle size) was added to 250 ml of sterile phosphate buffered saline (PBS; pH 7.4) to create a 10% molybdenum solution (w/v) in a sterile Erlenmeyer flask. This solution was mixed thoroughly and then allowed to settle at room temperature for approximately 90 hours. Following this, the supernatant was carefully removed from the flask by pipetting while ensuring that the settled powder was not disturbed. This supernatant was used as the treated saline solution for the experiment and was stored at room temperature until use.

The experiment was conducted on 2"×2" stainless steel coupons sprayed with the 10% molybdenum solution in PBS. The coupons were inoculated with 0.1 ml of MS-2 stock solution containing approximately $5.0 \times 10^8$ plaque forming units (PFU)/ml of MS-2 bacteriophage. MS-2 is a non-pathogenic virus that infects *E. coli* and other members of the family *Enterobacteriaceae*. It is commonly used as a human enteric virus surrogate because it is similar in size and shape and exhibits comparable resistance to various disinfectants. The virus inoculum was spread over the entire surface of the coupon using a sterile pipet tip. Duplicate coupons were included for each exposure contact time for both the test samples (sprayed with PBS containing molybdenum) and the control samples (sprayed with PBS only).

Immediately following inoculation, the coupons were sprayed once using a spray bottle from a distance of approximately 6 inches with either the molybdenum-treated PBS (test samples) or PBS alone (control samples).

The inoculated and sprayed coupons were placed in sealed Tupperware chambers with moist paper towels and incubated at room temperature (22.1° C.) to prevent drying which would lead to a reduction in viral numbers.

Duplicate samples from the control coupons were collected immediately upon inoculation to determine the baseline viral concentration recovered at t=0 minutes. The coupons were sampled by thorough rinsing with 1 ml of Dey-Engley (D/E) neutralizing broth in a sterile petri dish. The rinse solution was collected and placed into sterile 1.5 ml Eppendorf tubes.

All other control and test samples were held at room temperature for the remainder of the experiment (22.1° C. at a relative humidity of ~95%). At t=1, 5, 15, and 30 minutes, duplicate samples of the remaining control and test coupons were sampled and treated in the manner described previously.

To quantify the numbers of recovered viable MS-2 from each coupon, serial 10-fold dilutions of the neutralized samples were performed in sterile PBS and 0.1-ml volumes of each dilution were assayed using the double-agar overlay technique with duplicate plates for each dilution. In short, approximately 0.5 ml of a log-phase culture (3-4 hours growth in tryptic soy broth medium with agitation at 37° C.) of host *Escherichia coli* bacterium were added to 5 ml of molten tryptic soy agar (containing 1% agar) in a test tube. Next, 0.1 ml of each dilution of the test sample was added to the tube. The tubes were then vortexed gently to mix the cultures and poured onto the surfaces of separate tryptic soy agar plates. The plates were swirled gently to cover the entire surface of the plate with the agar overlay. The overlay was then allowed to solidify at room temperature and then the plates were incubated (inverted) for 18 to 24 hours at 37° C. The surviving MS-2 were enumerated by counting plaques (circular clearings in the bacterial growth on the agar overlays) to determine the number of PFU of virus per milliliter of each sample.

In order to confirm that the antimicrobial solution was sufficiently neutralized by the D/E, a neutralization verification test was performed. A volume of 0.4 ml of the 10% molybdenum in PBS solution was placed into 1 ml of D/E neutralizing broth. The solution was mixed and then MS-2 was added to a final concentration of approximately $5.2 \times 10^7$ PFU. The solution was mixed again and then was allowed to sit for ten minutes at room temperature (22.1° C.). Ten-fold serial dilutions of the neutralized solution were assayed as described previously. If the solution was completely neutralized, it was expected that there would be no reduction in MS-2 numbers in comparison to the controls in PBS alone.

The data were reported as the logarithmic reduction using the formula $-\log_{10}(N_t/N_0)$, where $N_0$ is the concentration of the recovered MS-2 at time=0 minutes and $N_t$ is the concentration of the viable MS-2 in the sample collected at time=t (i.e., 1, 5, 15, or 30 minutes). The percent reduction was also calculated.

A Student's t-test was used to statistically compare the reductions observed with the test spray containing molybdenum with the reductions observed with the control PBS spray. The reductions were considered to be statistically significant if the resultant P value was <0.05.

Results

No reduction in MS-2 was observed during the neutralization verification test, indicating that the D/E was successful in neutralizing the 10% molybdenum in PBS solution.

Inoculum=$5.2 \times 10^7$ PFU/coupon

Number of viable MS-2 virus particles recovered per coupon:

Control Sample A (0 minutes)=$3.65 \times 10^7$ PFU
Control Sample B (0 minutes)=$3.66 \times 10^7$ PFU
Control Sample A (1 minute)=$4.35 \times 10^7$ PFU
Control Sample B (1 minute)=$4.10 \times 10^7$ PFU
Control Sample A (5 minutes)=$2.51 \times 10^7$ PFU
Control Sample B (5 minutes)=$3.90 \times 10^7$ PFU
Control Sample A (15 minutes)=$3.25 \times 107$ PFU
Control Sample B (15 minutes)=$3.75 \times 10^7$ PFU
Control Sample A (30 minutes)=$3.7 \times 10^7$ PFU
Control Sample B (30 minutes)=$4.10 \times 10^7$ PFU
Test Sample A (1 minute)=$2.61 \times 10^7$ PFU
Test Sample B (1 minute)=$9.65 \times 10^6$ PFU
Test Sample A (5 minutes)=$2.29 \times 10^7$ PFU
Test Sample B (5 minutes)=$2.01 \times 10^7$ PFU
Test Sample A (15 minutes)=$2.85 \times 10^6$ PFU
Test Sample B (15 minutes)=$1.77 \times 10^7$ PFU
Test Sample A (30 minutes)=$1.86 \times 10^6$ PFU
Test Sample B (30 minutes)=$4.50 \times 10^6$ PFU Geometric mean number of viable MS-2 bacteriophage recovered from control spray samples after 1 minute=$4.22 \times 10^7$ PFU/coupon.

Geometric mean number of viable MS-2 bacteriophage recovered from control spray samples after 5 minutes=$3.13 \times 10^7$ PFU/coupon.

Geometric mean number of viable MS-2 bacteriophage recovered from control spray samples after 15 minutes=$3.49 \times 10^7$ PFU/coupon.

Geometric mean number of viable MS-2 bacteriophage recovered from control spray samples after 30 minutes=$3.89 \times 10^7$ PFU/coupon.

Geometric mean number of viable MS-2 bacteriophage recovered from test spray samples after 1 minute=$1.59 \times 10^7$ PFU/coupon.

Geometric mean number of viable MS-2 bacteriophage recovered from test spray samples after 5 minutes=$2.15 \times 10^7$ PFU/coupon.

Geometric mean number of viable MS-2 bacteriophage recovered from test spray samples after 15 minutes=$7.10 \times 10^6$ PFU/coupon.

Geometric mean number of viable MS-2 bacteriophage recovered from test spray samples after 30 minutes=$2.89 \times 10^6$ PFU/coupon.

Percent reduction from test spray samples after 1 minute=57.3%.

Percent reduction from test spray samples after 5 minutes=41.1%.

Percent reduction from test spray samples after 15 minutes=80.5%.

Percent reduction from test spray samples after 30 minutes=92.1%.

The table below shows antimicrobial efficacy of test samples sprayed with PBS with or without 10% activated molybdenum (Mo) with a contact time of either 1, 5, 15, or 30 minutes against MS-2 bacteriophage. Experiment was conducted with duplicate samples at 22.1° C. at a relative humidity of ~95% (t =0 minutes collected immediately following inoculation).

| | | Spray Treatment | | | | | |
|---|---|---|---|---|---|---|---|
| | | Control coupons (PBS) | | | Test flasks (PBS w/ 10% Mo) | | |
| Exposure Time (minutes) | Sample | $Log_{10}$ Reduction* | Average $Log_{10}$ Reduction ± SD | Average Percent Reduction | $Log_{10}$ Reduction* | Average $Log_{10}$ Reduction ± SD | Average Percent Reduction |
| 1 | A | 0.00 | 0.00 ± 0.00 | 0.0 | 0.15 | 0.37 ± 0.30 | 57.3 |
| | B | 0.00 | | | 0.58 | | |
| 5 | A | 0.16 | 0.08 ± 0.11 | 16.8 | 0.20 | 0.23 ± 0.04 | 41.1 |
| | B | 0.00 | | | 0.26 | | |
| 15 | A | 0.05 | 0.03 ± 0.04 | 6.7 | 1.11 | 0.71 ± 0.57 | 80.5 |
| | B | 0.00 | | | 0.31 | | |
| 30 | A | 0.00 | 0.00 ± 0.00 | 0.0 | 1.29 | 1.10 ± 0.27 | 92.1 |
| | B | 0.00 | | | 0.91 | | |

*Initial concentration of MS-2 bacteriophage was approximately $5.20 \times 10^7$ PFU/coupon; an average of $3.65 \times 10^7$ PFU was recovered from the control coupons at t = 0 minutes. This value was used to calculate the $log_{10}$ reductions for the subsequent samples collected.
SD Standard deviation Discussion The concentrations of MS-2 recovered from the control samples remained consistent over the entire course of the experiment. In contrast, small reductions in viable MS-2 were observed within 1 minute on the samples treated with the 10% molybdenum spray solution. The reductions observed after 1, 5, and 15 minutes of contact time were not statistically significant in comparison to the control samples ($P \leq 0.05$). However, within 30 minutes of contact time, the reductions in MS-2 recovered (average reduction of 1.10 $log_{10}$) were statistically significant in comparison to the control samples (P=0.029).

Example 15b—Surface Time-Kill Test of Stainless Steel Coupons Sprayed with Saline Solution Treated with Molybdenum Against Human Coronavirus Strain 229E Materials Prior to the experiment, 25 g of activated molybdenum powder (>99% pure; 45 μm particle size) was added to 250 ml of sterile phosphate buffered saline (PBS; pH 7.4) to create a 10% molybdenum solution (w/v) in a sterile Erlenmeyer flask. This solution was mixed thoroughly and then allowed to settle at room temperature for approximately 90 hours. Following this, the supernatant was carefully removed from the flask by pipetting while ensuring that the settled powder was not disturbed. This supernatant was used as the treated saline solution for the experiment and was stored at room temperature until use.

The experiment was conducted on 2"×2" stainless steel coupons sprayed with a 10% molybdenum solution in PBS. The coupons were inoculated with 0.1 ml of virus stock solution containing approximately $1.0 \times 10^6$ $TCID_{50}$/ml of human coronavirus strain 229E (ATCC#VR-740). The inoculum was spread over the entire surface of the coupon using a sterile pipet tip. Duplicate coupons were included for each exposure contact time for both the test samples (sprayed with PBS containing molybdenum) and the control samples (sprayed with PBS only).

Immediately following inoculation, the coupons were sprayed twice using a spray bottle from a distance of approximately 6 inches with either the molybdenum-treated PBS (test samples) or PBS alone (control samples).

The inoculated and sprayed coupons were placed in sealed Tupperware chambers with moist paper towels and incubated at room temperature (22.3° C.) to prevent drying which would lead to a large reduction in viral numbers.

Duplicate samples from the control coupons were collected immediately upon inoculation to determine the baseline viral concentration recovered at t=0 minutes. The coupons were sampled by thorough rinsing with 1 ml of Dey-Engley (D/E) neutralizing broth in a sterile petri dish. The rinse solution was collected and placed into sterile 1.5 ml Eppendorf tubes.

The collected samples were passed through Sephadex gel filtration columns to reduce cytotoxicity in the subsequent cell culture assay. Following this, the samples were passed through separate syringe filters (0.45 m pore size; pre-wetted with 3% beef extract to prevent virus adsorption to the filters) to remove any contaminants such as bacteria or fungi. This step was necessary since the experiment was not conducted in a sterile environment.

All other control and test samples were held at room temperature for the remainder of the experiment (22.3° C. at a relative humidity of ~95%). At t=1, 5, 15, and 30 minutes, duplicate samples of the remaining control and test coupons were sampled and treated in the manner described previously.

Virus concentrations for each neutralized and filtered sample were quantified using the Reed-Muench method to determine the tissue culture infectious dose that affected 50% of the wells ($TCID_{50}$). The samples were 10-fold serially diluted in minimal essential media (MEM). The assay was performed in 96-well cell culture plates containing monolayers of MRC-5 cells (fetal human lung fibroblast. Prior to the assay, the MRC-5 cells were gently rinsed twice with MEM and then the 96-well plates were inoculated with the diluted samples (6 wells inoculated with 50 microliters each per dilution) and the plates were incubated in an atmosphere of 5% $CO_2$ for 1 hour at 35° C. to allow the virus particles to adsorb to the cells.

Each 96-well plate also included at least 6 negative control wells containing cells only (no antimicrobials or virus) with 50 microliters of MEM added.)

Following this incubation period, 150 microliters of MEM containing 2% fetal bovine serum was added to each of the 96 wells and the plates were incubated in an atmosphere of 5% $CO_2$ for 6 days at 35° C.

The cells were observed daily for viral cytopathic effects (CPE) using an inverted microscope. The inoculated cells were compared to the negative control cells in the same 96-well plate to differentiate CPE from un-inoculated cells. Any CPE that was observed within 24 hours of incubation was considered to be caused by cytotoxicity (caused by sensitivity of the cells to the D/E neutralizing buffer or the antimicrobial) since CPE caused by coronavirus typically requires ≥2 days. Wells positive for CPE following 2 or more days were considered positive for viral growth. No CPE was observed in any of the negative control wells.)

After the incubation period, the $TCID_{50}$/coupon was determined. Six wells per dilution were used to ensure adequate precision of the assay. The greatest dilution in which 50% or higher of the wells were positive was used to determine the virus $TCID_{50}$/coupon following the method described by Payment and Trudel.

In order to confirm that the antimicrobial solution was sufficiently neutralized by the D/E, a neutralization verification test was performed. A volume of 0.4 ml of the 10% molybdenum in PBS solution (the estimated volume found in one spray) was placed into 1 ml of D/E neutralizing broth. The solution was mixed and then human coronavirus 229E was added to a final concentration of approximately $1.0 \times 10^6$ $TCID_{50}$. The solution was mixed again and then was allowed to sit for ten minutes at room temperature (22.3° C.). Ten-fold serial dilutions of the neutralized solution were assayed as described previously. If the solution was completely neutralized, it was expected that there would be no reduction in coronavirus 229E numbers in comparison to the controls in PBS alone.

The data were reported as the logarithmic reduction using the formula $-\log_{10}(N_t/N_0)$, where $N_0$ is the concentration of the recovered coronavirus at time=0 minutes and $N_t$ is the concentration of the surviving coronavirus in the sample collected at time=t (i.e., 1, 5, 15, or 30 minutes). The percent reduction was also calculated.

A Student's t-test was used to statistically compare the reductions observed with the test spray containing molybdenum with the reductions observed with the control PBS spray. The reductions were considered to be statistically significant if the resultant P value was ≤0.05.

Results

Inoculum =~$1.0 \times 10^6$ $TCID_{50}$/coupon
Number of viable virus particles recovered per coupon:
Control Sample A (0 minutes)=$3.6 \times 10^5$ $TCID_{50}$
Control Sample B (0 minutes)=$1.1 \times 10^6$ $TCID_{50}$
Control Sample A (1 minute)=$3.6 \times 10^5$ $TCID_{50}$
Control Sample B (1 minute)=$5.0 \times 10^5$ $TCID_{50}$
Control Sample A (5 minutes)=$4.3 \times 10^5$ $TCID_{50}$
Control Sample B (5 minutes)=$9.3 \times 10^5$ $TCID_{50}$
Control Sample A (15 minutes)=$3.6 \times 10^5$ $TCID_{50}$
Control Sample B (15 minutes)=$4.3 \times 10^5$ $TCID_{50}$
Control Sample A (30 minutes)=$4.3 \times 10^5$ $TCID_{50}$
Control Sample B (30 minutes)=$2.0 \times 10^5$ $TCID_{50}$
Test Sample A (1 minute)=$3.6 \times 10^5$ $TCID_{50}$
Test Sample B (1 minute)=$3.6 \times 10^5$ $TCID_{50}$
Test Sample A (5 minutes)=$2.0 \times 10^5$ $TCID_{50}$
Test Sample B (5 minutes)=$4.3 \times 10^4$ $TCID_{50}$
Test Sample A (15 minutes)=$2.0 \times 10^4$ $TCID_{50}$
Test Sample B (15 minutes)=$4.3 \times 10^4$ $TCID_{50}$
Test Sample A (30 minutes)=$1.1 \times 10^4$ $TCID_{50}$
Test Sample B (30 minutes)=$2.0 \times 10^4$ $TCID_{50}$
Geometric mean number of viable human coronavirus 229E recovered from control spray samples after 1 minute=$4.3 \times 10^5$ $TCID_{50}$/coupon
Geometric mean number of viable human coronavirus 229E recovered from control spray samples after 5 minutes=$6.3 \times 10^5$ $TCID_{50}$/coupon
Geometric mean number of viable human coronavirus 229E recovered from control spray samples after 15 minutes=$3.9 \times 10^5$ $TCID_{50}$/coupon
Geometric mean number of viable human coronavirus 229E recovered from control spray samples after 30 minutes=$3.0 \times 10^5$ $TCID_{50}$/coupon
Geometric mean number of viable human coronavirus 229E recovered from test spray samples after 1 minute=$3.6 \times 10^5$ $TCID_{50}$/coupon
Geometric mean number of viable human coronavirus 229E recovered from test spray samples after 5 minutes=$9.3 \times 10^4$ $TCID_{50}$/coupon
Geometric mean number of viable human coronavirus 229E recovered from test spray samples after 15 minutes=$3.0 \times 10^4$ $TCID_{50}$/coupon
Geometric mean number of viable human coronavirus 229E recovered from test spray samples after 30 minutes=$1.5 \times 10^4$ $TCID_{50}$/coupon
Percent reduction from test spray samples after 1 minute=30.8%
Percent reduction from test spray samples after 5 minutes=82.2%
Percent reduction from test spray samples after 15 minutes=94.4%
Percent reduction from test spray samples after 30 minutes=97.1%

The table below shows antimicrobial efficacy of test samples sprayed with PBS with or without 10% activated molybdenum (Mo) with a contact time of either 1, 5, 15, or 30 minutes against human coronavirus strain 229E (ATCC#VR-740). Experiment was conducted with duplicate samples at 22.3° C. at a relative humidity of ~95% (t=0 hours collected immediately following inoculation).

| Treatment | Sample | Log₁₀ removal* | | | |
|---|---|---|---|---|---|
| | | 1 min | 5 min | 15 min | 30 min |
| Control Spray | Sample 1 | 0.16 | 0.08 | 0.16 | 0.08 |
| (PBS) | Sample 2 | 0.01 | 0.00 | 0.08 | 0.41 |
| | Average (± SD) | 0.09 ± 0.11 | 0.04 ± 0.06 | 0.12 ± 0.06 | 0.25 ± 0.24 |
| Test Spray | Sample 1 | 016 | 041 | 141 | 1,66 |
| (PBS w/ 10% Mo) | Sample 2 | 016 | 108 | 108 | 1.41 |
| | Average (± SD) | 0.16 ± 0.00 | 0.75 ± 0.47 | †1.25 ± 0.24 | †1.54 ± 0.18 |

*Initial concentration of human coronavirus 229E was approximately $1.0 \times 10^6$ TCID50/coupon; an average of $5.1 \times 10^5$ TCID$_{50}$ was recovered from the control coupons at t = 0 minutes. This value was used to calculate the logio reductions for the subsequent samples collected.
SD Standard deviation.
†Reduction was statistically significant ($P \leq 0.05$) in comparison to the reductions observed on the control stainless steel coupons at the same exposure contact time.

Discussion

A loss of approximately 0.29 $\log_{10}$ was observed between the number of virus particles inoculated onto the coupons and the number of particles recovered from the control samples at t=0 minutes.

No reductions in human coronavirus 229E were observed during the neutralization verification test, indicating that the D/E was successful in neutralizing the 10% molybdenum in PBS solution.

The PBS solution containing 10% activated molybdenum was effective at reducing the numbers of viable human coronavirus 229E particles after 15 and 30 minutes of contact time (1.25 and 1.54 $\log_{10}$, respectively). The observed reductions were statistically significant in comparison to the reductions observed in the control samples after 15 and 30 minutes (P=0.023 and 0.025, respectively), but not after 1 and 5 minutes of contact time (P=0.42 and 0.17, respectively).

Example 16—Surface Time-Kill Test of Treated Polypropylene Test Coupons Comprising Molybdenum Against Methicillin Resistant *Staphylococcus aureus* and *Escherichia coli*

Example 16a—Surface Time-Kill Test of Treated Polypropylene Test Coupons Comprising Molybdenum against Methicillin Resistant *Staphylococcus aureus*

Materials

The experiment was conducted on 2"×2" treated polypropylene coupons containing 5% activated molybdenum (>99% pure; 45 μm particle size) and 2"×2" control polypropylene coupons (no added molybdenum).

A culture of methicillin resistant *Staphylococcus aureus* was prepared on the day before testing by inoculating one colony of the test organism into 100 ml of tryptic soy broth (TSB) with incubation overnight at 37° C. with agitation (250 rμm on an orbital shaker).

On the test date, the bacterial cells were washed by pelleting the cells via centrifugation. The supernatant was discarded and the pellet was re-suspended in sterile phosphate-buffered saline (PBS; pH 7.4). Three washing steps were performed in total.

The coupons were inoculated with 0.1 ml of the solution containing approximately 1.0×106 colony forming units (CFU) of the washed MRSA cells. The inoculum was spread over the surface of the coupon using a sterile pipet tip. Duplicate coupons were included for each exposure contact time for both the test polypropylene coupons (containing molybdenum) and the polypropylene control coupons.

The coupons were placed in sealed Tupperware chambers with moist paper towels and incubated at room temperature (21.6° C.) to prevent drying.

Duplicate samples from the control coupons were collected immediately upon inoculation to determine the baseline MRSA concentration recovered at t=0 hours. The coupons were sampled with sterile cotton swabs to recover the bacteria and the swabs placed into separate 1-ml volumes of Dey-Engley (D/E) neutralizing broth. The samples were vortexed for 30 seconds and then the swabs were removed and discarded. The samples were then 10-fold serially diluted in PBS. The various dilutions were inoculated onto mannitol salt agar (MSA) plates using the spread plate method. The plates were incubated for 24 to 48 hours at 37° C. and the colonies enumerated.

All other control and test coupons were held at room temperature for the remainder of the experiment (21.6° C. at a relative humidity of ~95%). At t=4 and 24 hours, duplicate samples of the remaining control and test coupons were sampled and assayed on MSA plates in the manner described previously.

Colonies were counted, and the levels of surviving MRSA CFU per coupon determined. The data were reported as the logarithmic reduction using the formula $-\log_{10} (N_t/N_0)$, where $N_0$ is the concentration of the recovered MRSA at time=0 hours and $N_t$ is the concentration of the surviving MRSA in the sample collected at time=t (i.e., 4 or 24 hours). The percent reduction was also calculated.

A Student's t-test was used to statistically compare the reductions observed on the test coupons with the reductions observed on the control coupons. The reductions were considered to be statistically significant if the resultant P value was ≤0.05.

Results

Inoculum=3.8×106 CFU/coupon
Number of MRSA recovered per coupon:
Control Polypropylene A (0 hours)=2.3×10⁶ CFU
Control Polypropylene B (0 hours)=2.7×10⁶ CFU
Control Polypropylene A (4 hours)=1.7×10⁶ CFU
Control Polypropylene B (4 hours)=1.8×10⁶ CFU
Control Polypropylene A (24 hours)=2.1×10⁶ CFU
Control Polypropylene B (24 hours)=1.9×10⁶ CFU
Treated Polypropylene Containing Molybdenum A (4 hours)=6.3×10⁴ CFU
Treated Polypropylene Containing Molybdenum B (4 hours)=1.7×10⁵ CFU Treated Polypropylene Containing Molybdenum A (24 hours)=5 CFU Treated Polypropylene Containing Molybdenum B (24 hours)=5 CFU Geometric mean number of MRSA recovered from control polypropylene coupons after 4 hours=$1.8 \times 10^6$ CFU/coupon Geometric mean number of MRSA recovered from control polypropylene coupons after 24 hours=$2.0 \times 10^6$ CFU/coupon Geometric mean number of MRSA recovered from treated polypropylene coupons containing 5% molybdenum after 4 hours=$1.0 \times 10^5$ CFU/coupon Geometric mean number of MRSA recovered from treated polypropylene coupons containing 5% molybdenum after 24 hours=5 CFU/coupon Percent reduction of MRSA on treated polypropylene coupons containing 5% molybdenum after 4 hours=95.9%

Percent reduction of MRSA on treated polypropylene coupons containing 5% molybdenum after 24 hours=99.9998%

The table below shows antimicrobial efficacy of treated polypropylene coupons containing 5% molybdenum against methicillin resistant *Staphylococcus aureus*. The experiment was conducted with duplicate samples at 21.6° C. at a relative humidity of ~95% (t=0 hours collected immediately following inoculation).

|  |  | Control polypropylene coupons |  | Test polypropylene coupons w/5% Mo |  | Average |
|---|---|---|---|---|---|---|
| Exposure (hours) Time | Sample | $Log_{10}$ Reduction* | Average $Log_{10}$ Reduction ± SD | $Log_{10}$ Reduction* | Average $Log_{10}$ Reduction ± SD | Percent Reduction |
| 4 | A | 0.17 | 0.15 ± 0.03 | 1.60 | †1.39 ± 0.3 | 95.9 |
|  | B | 0.13 |  | 1.18 |  |  |
| 24 | A | 0.07 | 0.10 ± 0.04 | 5.70 | †5.70 ± 0.00 | 99.9998 |
|  | B | 0.13 |  | 5.70 |  |  |

*Initial concentration of MRSA recovered from the control coupons at t = 0 hours was approximately $2.5 \times 10^6$ CFU per coupon. This value was used to calculate the $log_{10}$ reductions for the subsequent samples collected.
SD Standard deviation.
†Reduction was statistically significant ($P \leq 0.05$) in comparison to the reductions observed on the control polypropylene coupons at the same exposure contact time.

Discussion

Small reductions were observed in the numbers of MRSA recovered from the control polypropylene coupons at both exposure contact times (average of 0.13 $log_{10}$). In contrast, significant reductions in the numbers of MRSA recovered from the test polypropylene coupons containing 5% molybdenum were observed after both 4 hours (average of 1.39 $log_{10}$) and 24 hours (average of 5.70 $log_{10}$) of exposure. These reductions were statistically significant in comparison to the control polypropylene coupons sampled at the same time (P=0.028 and P=0.000029, respectively).

Example 16b—Surface Time-Kill Test of Treated Polypropylene Test Coupons Comprising Molybdenum Against *Escherichia coli*

Materials

The experiment was conducted on 2"×2" treated polypropylene coupons containing 5% activated molybdenum (>99% pure; 45 μm particle size) and 2"×2" control polypropylene coupons (no added molybdenum). The coupons were soaked in 3% hydrogen peroxide for 24 hours and then dried for an additional 48 hours prior to the start of the experiment.

A culture of Escherichia coli was prepared on the day before testing by inoculating one colony of the test organism into 100 ml of tryptic soy broth (TSB) with incubation overnight at 37° C. with agitation (250 rpm on an orbital shaker).

On the test date, the bacterial cells were washed by pelleting the cells via centrifugation. The supernatant was discarded and the pellet was re-suspended in sterile phosphate-buffered saline (PBS; pH 7.4). Three washing steps were performed in total.

The coupons were inoculated with 0.1 ml of the solution containing approximately $1.0 \times 10^6$ colony forming units (CFU) of the washed *E. coli* cells. The inoculum was spread over the surface of the coupon using a sterile pipet tip. Duplicate coupons were included for each exposure contact time for both the test polypropylene coupons (containing molybdenum) and the polypropylene control coupons.

The coupons were placed in sealed Tupperware chambers with moist paper towels and incubated at room temperature (21.8° C.) to prevent drying.

Duplicate samples from the control coupons were collected immediately upon inoculation to determine the baseline *E. coli* concentration recovered at t=0 hours. The coupons were sampled with sterile cotton swabs to recover the bacteria and the swabs placed into separate 1-ml volumes of Dey-Engley (D/E) neutralizing broth. The samples were vortexed for 30 seconds and then the swabs were removed and discarded. The samples were then 10-fold serially diluted in PBS. The various dilutions were inoculated onto eosin methylene blue (EMB) agar plates using the spread plate method. The plates were incubated for 24 hours at 37° C. and the colonies enumerated.

All other control and test coupons were held at room temperature for the remainder of the experiment (21.8° C. at a relative humidity of ~95%). At t=4 and 24 hours, duplicate samples of the remaining control and test coupons were sampled and assayed on EMB plates in the manner described previously.

Colonies were counted, and the levels of surviving *E. coli* CFU per coupon determined. The data were reported as the logarithmic reduction using the formula $-log_{10}(Nt/N0)$, where N0 is the concentration of the recovered *E. coli* at time=0 hours and Nt is the concentration of the surviving *E. coli* in the sample collected at time=t (i.e., 4 or 24 hours). The percent reduction was also calculated.

A Student's t-test was used to statistically compare the reductions observed on the test coupons with the reductions observed on the control coupons. The reductions were considered to be statistically significant if the resultant P value was ≤0.05.

Results

Inoculum=2.12×10⁶ CFU/coupon
Number of *E. coli* recovered per coupon:
Control Polypropylene A (0 hours)=2.04×10⁶ CFU
Control Polypropylene B (0 hours)=2.20×10⁶ CFU
Control Polypropylene A (4 hours)=1.95×10⁶ CFU
Control Polypropylene B (4 hours)=2.21×10⁶ CFU
Control Polypropylene A (24 hours)=1.59×10⁶ CFU
Control Polypropylene B (24 hours)=1.28×10⁶ CFU
Treated Polypropylene Containing Molybdenum A (4 hours)=1.50×10¹ CFU
Treated Polypropylene Containing Molybdenum B (4 hours)=3.00×10¹ CFU
Treated Polypropylene Containing Molybdenum A (24 hours)=6.00×10¹ CFU
Treated Polypropylene Containing Molybdenum B (24 hours)=<5.00×10¹ CFU
Geometric mean number of *E. coli* recovered from control polypropylene coupons after 4 hours=2.07×10⁶ CFU/coupon
Geometric mean number of *E. coli* recovered from control polypropylene coupons after 24 hours=1.42×10⁶ CFU/coupon
Geometric mean number of *E. coli* recovered from treated polypropylene coupons containing 5% molybdenum after 4 hours=2.12×10¹ CFU/coupon
Geometric mean number of *E. coli* recovered from treated polypropylene coupons containing 5% molybdenum after 24 hours=1.73×10¹ CFU/coupon
Percent reduction of *E. coli* on treated polypropylene coupons containing 5% molybdenum after 4 hours=99.999%
Percent reduction of *E. coli* on treated polypropylene coupons containing 5% molybdenum after 24 hours=>99.9992%

The table below shows antimicrobial efficacy of treated polypropylene coupons containing 5% molybdenum against Escherichia coli. The experiment was conducted with duplicate samples at 21.2° C. at a relative humidity of ~95% (t=0 hours collected immediately following inoculation).

Discussion

Small reductions were observed in the numbers of *E. coli* recovered from the control polypropylene coupons at both exposure contact times (average of 0.13 $\log_{10}$). In contrast, significant reductions in the numbers of *E. coli* recovered from the test polypropylene coupons containing 5% molybdenum were observed after both 4 hours (average of 5.00 $\log_{10}$) and 24 hours (average of >5.09 $\log_{10}$) of exposure. These reductions were statistically significant in comparison to the control polypropylene coupons sampled at the same time (P=0.0009 and P=0.012, respectively).

Example 17—Suspension Time-Kill Test of Molybdenum Powder Suspended in Phosphate Buffered Saline Against *Acinetobacter baumannii* and *Candida albicans*

Example 17a—Suspension Time-Kill Test of Molybdenum Powder Suspended in Phosphate Buffered Saline against *Acinetobacter baumannii*

Methods

1. A culture of *Acinetobacter baumannii* was prepared on the day before testing by inoculating one colony of the test organism into 100 ml of tryptic soy broth (TSB) and incubation overnight at 37° C.

On the test date, the bacterial cells were washed by pelleting the cells via centrifugation. The supernatant was discarded and the pellet was re-suspended in 0.01 M phosphate-buffered saline (PBS; pH 7.4). Three washing steps were performed in total.

The cell suspension was diluted in 100 ml of sterile PBS in 250-ml screw cap Erlenmeyer flasks to obtain a density of ~1×10⁵ colony-forming units (CFU) per ml. Six flasks were included in the experiment (3 control flasks, 3 test flasks).

Samples from the three control flasks were collected immediately upon inoculation/mixing to determine the baseline bacterial concentration at t=0 hours. A volume of 0.1 ml was removed from each and placed into separate 0.9-ml volumes of Dey-Engley (D/E) neutralizing broth. The samples were vortexed for 10 seconds and then 10-fold serially diluted in PBS. The various dilutions were inoculated onto tryptic soy agar (TSA) plates using the spread plate method. The plates were incubated for 24 to 48 hours at 37° C. and the colonies enumerated.

Also at t=0, 2 grams of pure molybdenum powder was added to each of the test flasks and the solution mixed

| Exposure Time (hours) | Sample | Control polypropylene coupons | | Test polypropylene coupons w/ 5% Mo | | Average Percent Reduction |
|---|---|---|---|---|---|---|
| | | $\log_{10}$ Reduction* | Average $\log_{10}$ Reduction ± SD | $\log_{10}$ Reduction* | Average $\log_{10}$ Reduction ± SD | |
| 4 | A | 0.04 | 0.02 ± 0.03 | 5.15 | †5.00 ± 0.21 | 99.9990 |
| | B | 0.00 | | 4.85 | | |
| 24 | A | 0.13 | 0.18 ± 0.06 | 4.55 | >†5.09 ± 0.76 | >99.9992 |
| | B | 0.22 | | >5.63 | | |

*Initial concentration of *E. coli* recovered from the control coupons at t = 0 hours was approximately 2.12 × 10⁶ CFU per coupon. This value was used to calculate the $\log_{10}$ reductions for the subsequent samples collected. SD Standard deviation.
†Reduction was statistically significant (P ≤ 0.05) in comparison to the reductions observed on the control polypropylene coupons at the same exposure contact time.

thoroughly to result in a 2% Mo solution (wt/vol). All six flasks were placed on an orbital shaker at room temperature 20.8° C. with agitation (250 rpm).

All control and test flasks were sampled in the manner described previously at t=3, 6, and 24 hours and assayed on TSA plates as before.

In order to confirm that the antimicrobial solution was sufficiently neutralized by the D/E, a neutralization verification test was performed. A volume of 0.1 ml of the 2% molybdenum in PBS solution was placed into 0.9 ml of D/E neutralizing broth. The solution was mixed and then *A. baumannii* was added to a final concentration of approximately $1.0 \times 10^5$ CFU/ml. The solution was mixed again and then was allowed to sit for ten minutes at room temperature (20.8° C.). Ten-fold serial dilutions of the neutralized solution were assayed as described previously.

Colonies were counted, and the levels of surviving *A. baumannii* CFU per ml in each flask determined. The data were reported as the logarithmic reduction using the formula $-\log_{10}(N_t/N_0)$, where $N_0$ was the concentration of surviving *A. baumannii* at time=0 hours and $N_t$ was the concentration of *A. baumannii* in the sample collected at time=t (e.g., 3, 6, or 24 hours).

A Student's t-test was used to statistically compare the reductions observed in the test flasks with the reductions observed in the control flasks (assuming unequal variances). The reductions in the test flasks were considered to be statistically significant if the resultant P value was ≤0.05.

Results

The neutralization verification test results showed that the D/E neutralizing buffer was able to completely neutralize the antimicrobial effects of the 2% molybdenum solution. No differences were observed between the samples neutralized with the D/E for 10 minutes prior to inoculation with *A. baumannii* and the control samples with *A. baumannii* inoculated into sterile PBS.

The results are shown in the table below. Small reductions were observed in the numbers of *A. baumannii* recovered from the control flasks at all of the exposure contact times (average of 0.55 $\log_{10}$). In contrast, no *A. baumannii* were recovered from the test flasks amended with 2% molybdenum powder after 3, 6, or 24 hours of exposure. The bacterial numbers had fallen to below the detection limit of the assay (<5.0 CFU/ml); therefore, these reductions corresponded to a >4.61 $\log_{10}$ reduction (>99.9975% reduction) and were highly statistically significant in comparison to the control flasks sampled at the same time (P=0.000013, P=0.00018, and P=0.0011, respectively).

The table below shows survival of *Acinetobacter baumannii* in phosphate buffered saline containing 2% pure molybdenum (wt/vol) after 3, 6, and 24 hours at 20.8° C.

| | | Control (PBS) | | PBS with 2% Mo | | |
|---|---|---|---|---|---|---|
| Exposure Time (hours) | Sample | $\log_{10}$ Reduction* | Average $\log_{10}$ Reduction ± SD | $\log_{10}$ Reduction* | Average $\log_{10}$ Reduction ± SD | Average Percent Reduction |
| 3 | A | 0.55 | 0.57 ± 0.03 | > 4.61 | > 4.61† ± 0.00 | > 99.9975 |
|   | B | 0.60 |             | > 4.61 |                  |           |
|   | C | 0.57 |             | > 4.61 |                  |           |
| 6 | A | 0.58 | 0.66 ± 0.09 | > 4.61 | > 4.61† ± 0.00 | > 99.9975 |
|   | B | 0.76 |             | > 4.61 |                  |           |
|   | C | 0.65 |             | > 4.61 |                  |           |
| 24 | A | 0.17 | 0.43 ± 0.24 | > 4.61 | > 4.61† ± 0.00 | > 99.9975 |
|   | B | 0.64 |             | > 4.61 |                  |           |
|   | C | 0.47 |             | > 4.61 |                  |           |

*Initial Concentration = $2.03 \times 10^5$ CFU/ml (t = 0 hours)
SD = standard deviation
> = the bacteria had fallen to below the detection limit of the assay (<5.0 CFU per milliliter or a 4.61 $\log_{10}$ reduction); therefore, the reduction was > 4.61 $\log_{10}$ reduction (i.e., >99.9975% reduction).
†Reduction was statistically significant (P ≤ 0.05) in comparison to the reductions observed on the control phosphate buffered saline flasks at the same exposure contact time.

Example 17b—Suspension Time-Kill Test of Molybdenum Powder Suspended in Phosphate Buffered Saline Against *Candida albicans*

Methods

A culture of *Candida albicans* (ATCC #10231) was prepared on the day before testing by inoculating one colony of the test organism into 100 ml of tryptic soy broth (TSB) and incubation overnight at 37° C.

On the test date, the yeast cells were washed by pelleting the cells via centrifugation. The supernatant was discarded and the pellet was re-suspended in 0.01 M phosphate-buffered saline (PBS; pH 7.4). Three washing steps were performed in total.

The cell suspension was diluted in 100 ml of sterile PBS in 250-ml screw cap Erlenmeyer flasks to obtain a density of ~$1 \times 10^5$ colony-forming units (CFU) per ml. Six flasks were included in the experiment (3 control flasks, 3 test flasks). Test flasks contained 100 ml of PBS with 2 grams of pure molybdenum powder (2% Mo wt/vol solution). All six flasks were placed on an orbital shaker at room temperature 21.9° C. with agitation (200 rpm).

Samples from the three control flasks were collected immediately upon inoculation/mixing to determine the baseline yeast concentration at t=0 hours. A volume of 0.1 ml was removed from each and placed into separate 0.9-ml volumes of Dey-Engley (D/E) neutralizing broth. The samples were vortexed for 10 seconds and then 10-fold serially diluted in PBS. The various dilutions were inoculated onto potato dextrose agar (PDA) plates using the spread plate method. The plates were incubated for 48 hours at 37° C. and the colonies enumerated.

All control and test flasks were sampled in the manner described previously at t=3, 6, and 24 hours and assayed on PDA plates as before.

In order to confirm that the antimicrobial solution was sufficiently neutralized by the D/E, a neutralization verification test was performed. A volume of 0.1 ml of the 2% molybdenum in PBS solution was placed into 0.9 ml of D/E neutralizing broth. The solution was mixed and then *C. albicans* was added to a final concentration of approximately $1.0 \times 10^5$ CFU/ml. The solution was mixed again and then was allowed to sit for 10 minutes at room temperature (21.9° C.). Ten-fold serial dilutions of the neutralized solution were assayed as described previously. If the solution was completely neutralized, it was expected that there would be no reduction in *C. albicans* numbers in comparison to the controls in PBS alone.

Colonies were counted, and the levels of surviving *C. albicans* CFU per ml in each flask determined. The data were reported as the logarithmic reduction using the formula $-\log_{10}(N_t/N_0)$, where $N_0$ was the concentration of surviving *C. albicans* at time=0 hours and $N_t$ was the concentration of *C. albicans* in the sample collected at time=t (i.e., 3, 6, or 24 hours).

A Student's t-test was used to statistically compare the reductions observed in the test flasks with the reductions observed in the control flasks. The reductions in the test flasks were considered to be statistically significant if the resultant P value was ≤0.05.

Results

The neutralization verification test results showed that the D/E neutralizing buffer was able to completely neutralize the antimicrobial effects of the 2% molybdenum solution. No differences were observed between the samples neutralized with the D/E for 10 minutes prior to inoculation with *C. albicans* and the control samples with *C. albicans* inoculated into sterile PBS. Therefore, the reductions observed during the subsequent exposure tests may be considered accurate.

The results are shown in table below. Small reductions were observed in the numbers of *C. albicans* recovered from the control flasks at all of the exposure contact times (average of 0.09 $\log_{10}$). In contrast, no *C. albicans* were recovered from the test flasks amended with 2% molybdenum powder after 3, 6, or 24 hours of exposure. The yeast numbers fell to below the detection limit of the assay (<5.0 CFU/ml); therefore, these reductions corresponded to a >4.15 $\log_{10}$ reduction (>99.993% reduction) and were highly statistically significant in comparison to the control flasks sampled at the same time (P=$6.4 \times 10^{-8}$, P=$7.0 \times 10^{-8}$, and P=$1.1 \times 10^{-7}$, respectively).

The table below shows survival of *Candida albicans* (ATCC #10231) in phosphate buffered saline containing 2% pure molybdenum (wt/vol) after 3, 6, and 24 hours at 21.9° C.

| Exposure Time (hours) | Sample | Control (PBS) | | PBS with 2% Mo | | |
|---|---|---|---|---|---|---|
| | | $\log_{10}$ Reduction* | Average $\log_{10}$ Reduction ± SD | $\log_{10}$ Reduction* | Average $\log_{10}$ Reduction ± SD | Average Percent Reduction |
| 3 | A | 0.00 | 0.04 ± 0.06 | > 4.15 | > 4.15† ± 0.00 | > 99.993 |
|   | B | 0.11 |             | > 4.15 | | |
|   | C | 0.02 |             | > 4.15 | | |
| 6 | A | 0.00 | 0.06 ± 0.07 | > 4.15 | > 4.15† ± 0.00 | > 99.993 |
|   | B | 0.03 |             | > 4.15 | | |
|   | C | 0.14 |             | > 4.15 | | |
| 24 | A | 0.12 | 0.18 ± 0.08 | > 4.15 | > 4.15† ± 0.00 | > 99.993 |
|    | B | 0.27 |             | > 4.15 | | |
|    | C | 0.15 |             | > 4.15 | | |

*Initial Concentration = $7.00 \times 10^4$ CFU/ml (t = 0 hours)
SD = standard deviation
> = the viable yeast had fallen to below the detection limit of the assay (<5.0 CFU per milliliter or a 4.15 $\log_{10}$ reduction); therefore, the reduction was >4.15 $\log_{10}$ reduction (i.e., >99.993% reduction).
†Reduction was statistically significant (P ≤ 0.05) in comparison to the reductions observed on the control phosphate buffered saline flasks at the same exposure contact time.

Example 18—X-Ray Diffraction Analysis Report

Purpose

The present example provides an X-ray diffraction (XRD) analysis to determine certain crystalline phases present in a sample of molybdenum that has been activated using hydrogen peroxide (as reported herein in Examples above).

Results

The sample was placed into a bulk sample holder and pressed flat with a glass slide for analysis. XRD data was collected by a coupled Theta:2-Theta scan on a Rigaku Ultima-III diffractometer equipped with Copper x-ray tube, Ni beta filter, parafocusing optics, computer-controlled slits, and D/tex Ultra 1D strip detector.

Figure 7:
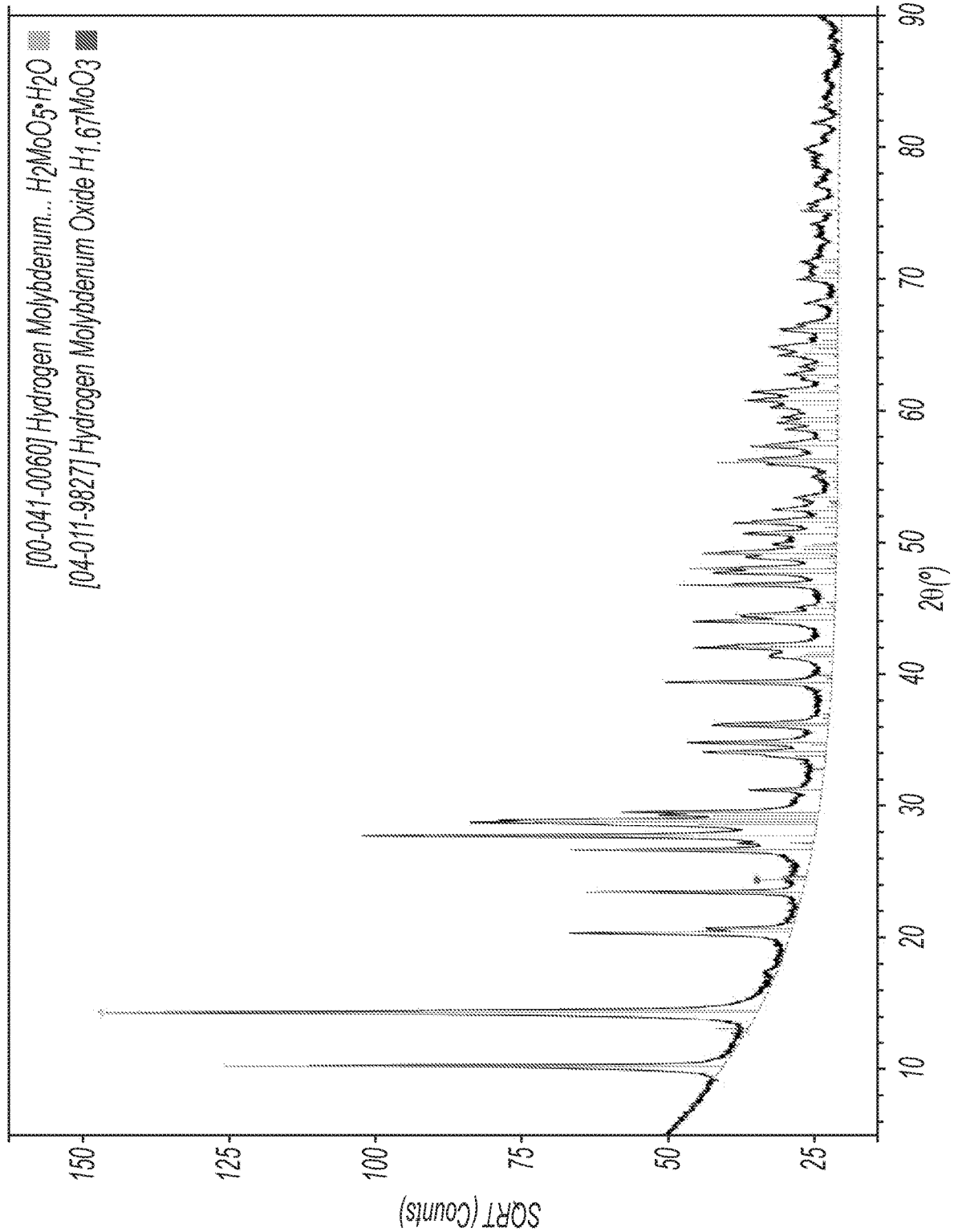
FIG. 7 is a XRD analysis of molybdenum activated with $H_2O_2$.

FIG. 7 shows the phase identification results for the sample obtained by comparing the background-subtracted experimental data to the ICDD/ICSD diffraction database. Intensity was plotted using square root (counts) to emphasize the weaker peaks. Monoclinic hydrogen molybdenum oxide hydrate ($H_2MoO_5 \cdot H_2O$) was the primary phase observed in the sample with trace amounts of hydrogen molybdenum oxide ($H_{1.67}MoO_3$).

Semiquantitative analysis was performed using WPF (that is, whole pattern fitting), which is a subset of Rietveld Refinement that accounts for all intensity above the background curve. This technique requires that either the structure factors and atomic locations or the reference intensity ratio (a way of comparing the diffracting power of different phases) are known for all phases identified. In this case, quantitative analysis by XRD was not attempted for this sample because the reference intensity ratio (RIR), which is needed to account for the relative diffraction intensity from different crystal structures, is not available for the major phase and because the peak near 17 degrees remains unidentified.

The invention claimed is:

1. An anti-pathogen solid composition comprising about 0.01% to about 5% by weight of an active component, wherein the active component comprises particles of an activated transition metal oxide; and
   about 1% to about 99.99% by weight of a polymer, wherein:
   the activated transition metal oxide comprises $MoO_2$, $MoO_3$, $H_2MoO_5$, $MoO_6$, or a hydrate thereof;
   the particles of the activated transition metal oxide have a cubic, spherical, monoclinic, hexagonal, orthorhombic, tetragonal, triclinic, or rhombohedral crystal structure;
   the particles of the activated transition metal oxide have a size of between larger than 100 nm and smaller than 100 μm; and
   the polymer is polypropylene.

2. The anti-pathogen solid composition of claim 1, wherein the activated transition metal oxide is or comprises $MoO_3$.

3. The anti-pathogen solid composition of claim 1, wherein the anti-pathogen solid composition comprises about 0.1% to about 3% by weight of the active component.

4. The anti-pathogen solid composition of claim 1, wherein the particles of the activated transition metal or transition metal oxide have a size of about 1 nm to about 1000 nm.

5. The anti-pathogen solid composition of claim 1, wherein the particles of the activated transition metal or transition metal oxide have a size of about 40 μm to about 50 μm.

6. The anti-pathogen solid composition of claim 1, further comprising a second metal or metal oxide, selected from Ni, Zn, Mn, Au, Ag, Cu, and Pd, or oxides thereof.

7. The anti-pathogen solid composition of claim 1, further comprising an antioxidant.

8. The anti-pathogen solid composition of claim 1, wherein the anti-pathogen solid composition is flexibly formed to cover a surface.

* * * * *

UNITED STATES PATENT AND TRADEMARK OFFICE
CERTIFICATE OF CORRECTION

| | |
|---|---|
| PATENT NO. | : 12,201,115 B2 |
| APPLICATION NO. | : 17/638368 |
| DATED | : January 21, 2025 |
| INVENTOR(S) | : Jeffery L. Dudding et al. |

Page 1 of 1

It is certified that error appears in the above-identified patent and that said Letters Patent is hereby corrected as shown below:

In the Claims

In Claim 1, Column 55, Line number 9, please delete:
"$MoO_3$, $H_2MoO_5$, $MoO_6$, or a hydrate thereof;"

And insert:
-- $MoO_3$, $H_2MoO_5$, or $Mo_2O_6$; --

Signed and Sealed this
Twenty-ninth Day of April, 2025

Coke Morgan Stewart
*Acting Director of the United States Patent and Trademark Office*